US008067390B2

(12) United States Patent
Merritt et al.

(10) Patent No.: US 8,067,390 B2
(45) Date of Patent: Nov. 29, 2011

(54) THERAPEUTIC TARGETING OF INTERLEUKINS USING SIRNA IN NEUTRAL LIPOSOMES

(75) Inventors: William M. Merritt, Houston, TX (US); Anil K. Sood, Pearland, TX (US); Menashe Bar-Eli, Houston, TX (US); Gabriel Lopez-Berestein, Bellaire, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

(21) Appl. No.: 12/527,684

(22) PCT Filed: Feb. 29, 2008

(86) PCT No.: PCT/US2008/055486
§ 371 (c)(1),
(2), (4) Date: Mar. 8, 2010

(87) PCT Pub. No.: WO2008/109432
PCT Pub. Date: Sep. 12, 2008

(65) Prior Publication Data
US 2010/0172962 A1  Jul. 8, 2010

Related U.S. Application Data

(60) Provisional application No. 60/892,772, filed on Mar. 2, 2007.

(51) Int. Cl.
*A01N 43/04* (2006.01)
*A61K 31/70* (2006.01)

(52) U.S. Cl. .................................................. 514/44 A

(58) Field of Classification Search .................. 514/44 A
See application file for complete search history.

(56) References Cited

U.S. PATENT DOCUMENTS

| 5,030,453 | A | 7/1991 | Lenk et al. | 424/450 |
|---|---|---|---|---|
| 5,962,016 | A | 10/1999 | Willis | 424/450 |
| 6,506,559 | B1 | 1/2003 | Driver et al. | 435/6 |
| 6,573,099 | B2 | 6/2003 | Graham | 435/455 |
| 6,673,611 | B2 | 1/2004 | Thompson et al. | 435/455 |
| 6,680,068 | B2 | 1/2004 | Jain et al. | 424/450 |
| 6,953,838 | B2 | 10/2005 | Vale, Jr. et al. | 530/350 |
| 2002/0168707 | A1 | 11/2002 | Graham | 435/69.1 |
| 2003/0012812 | A1 | 1/2003 | Tormo et al. | 424/450 |
| 2003/0051263 | A1 | 3/2003 | Fire et al. | 800/13 |
| 2003/0055020 | A1 | 3/2003 | Fire et al. | 514/44 A |
| 2003/0159161 | A1 | 8/2003 | Graham et al. | 800/8 |
| 2004/0019001 | A1 | 1/2004 | McSwiggen | 514/44 A |
| 2004/0064842 | A1 | 4/2004 | Graham et al. | 800/8 |
| 2004/0204377 | A1 | 10/2004 | Rana | 514/44 A |
| 2004/0208921 | A1 | 10/2004 | Ho et al. | 424/450 |
| 2004/0265839 | A1 | 12/2004 | Mello et al. | 435/6 |
| 2005/0107325 | A1* | 5/2005 | Manoharan et al. | 514/44 |
| 2005/0267027 | A1 | 12/2005 | Lounsbury et al. | 514/12 |
| 2006/0134221 | A1* | 6/2006 | Geall | 424/489 |
| 2006/0240093 | A1 | 10/2006 | MacLachlan et al. | 514/44 |
| 2007/0135370 | A1 | 6/2007 | MacLachlan et al. | 514/44 A |
| 2008/0317811 | A1* | 12/2008 | Andre et al. | 424/423 |
| 2009/0012021 | A1 | 1/2009 | Sood et al. | 514/44 R |

FOREIGN PATENT DOCUMENTS

| WO | WO 02/100435 | 12/2002 |
|---|---|---|
| WO | WO 03/015757 | 2/2003 |
| WO | WO 03/027327 | 4/2003 |
| WO | WO 2004/002453 | 1/2004 |
| WO | WO 2006/113679 | 10/2006 |
| WO | WO 2007/001943 | 1/2007 |

OTHER PUBLICATIONS

Bailey and Sullivan, "Efficient encapsulation of DNA plasmids in small neutral liposomes induced by ethanol and calcium," *Biochimica. Biophys. Acts.*, 1468:239-252, 2000.
Bangham et al., "The action of steroids and streptolysin S on the permeability of phospholipid structures to cations," *J. Mol. Biol.*, 13:253-259, 1965.
Deamer and Uster, In: Liposome Preparation: Methods and Mechanisms, Ostro (Ed.), Liposomes, 1983.
Dokka et al., "Oxygen radical-mediated pulmonary toxicity induced by some cationic liposomes," *Pharm. Res.*, 17:521-25, 2000.
Donze and Picard, "RNA interference in mammalian cells using siRNAs synthesized with T7 RNA polymerase," *Nucleic Acids Res.*, 30:e46, 2002.
Duxbury et al., "EphA2: a determinant of malignant cellular behavior and a potential therapeutic target in pancreatic adenocarcinoma," *Oncogene*, 23:1448-1456, 2004.
Elbashir et al., "Duplexes of 21-nucleotide RNAs mediate RNA interference in cultured mammalian cells," *Nature*, 411:494-498, 2001.
Elmén et al., "Locked nucleic acid (LNA) mediated improvements in siRNA stability and functionality," *Nucleic Acids Res.*, 33:439-47, 2005.
Farhood et al., "The role of dioleoyl phosphatidylethanolamine in cationic liposome mediated gene transfer," *Biochim. Biophys. Act.*, 1235:289-95, 1995.
Fire et al., "Potent and specific genetic interference by double-stranded RNA in *Caenorhabditis elegans*," *Nature*, 391:806-811, 1998.
Ghosh and Bachawat, In: *Liver Diseases, Targeted Diagnosis and Therapy Using Specific Receptors and Ligands*, Wu et al. (Eds.) Marcel Dekker, NY, 87-104, 1991.
Gutierrez-Puente et al., "Safety, pharmacokinetics, and tissue distribution of liposomal P-ethoxy antisense oligonucleotides targeted to Bcl-2," *J. Pharmacol. Exp. Ther.*, 291:865-869, 1999.*
Halder et al., "Focal adhesion kinase silencing augments docetaxel-mediated apoptosis in ovarian cancer cells," *Clin. Cancer Res.*, 11(24 Pt. 1):8829-36, 2005.

(Continued)

*Primary Examiner* — Brian Whiteman
(74) *Attorney, Agent, or Firm* — Fulbright & Jaworski L.L.P.

(57) ABSTRACT

The present invention relates to the fields of molecular biology and drug delivery. In certain embodiments, the present invention provides compositions that include an siRNA targeted to an interleukin and a neutral lipid, and methods of treating a human subject with cancer involving administering to the subject a pharmaceutically effective amount of an interleukin-8 antagonist or a composition as set forth herein.

20 Claims, 15 Drawing Sheets

OTHER PUBLICATIONS

Halder et al., "Focal adhesion kinase targeting using in vivo short interfering RNA delivery in neutral liposomes for ovarian carcinoma therapy," *Clin. Cancer Res.*, 12:4916-4924, 2006.

Huang et al., "Fluorescence characteristics of site-specific and stereochemically distinct benzo[a]pyrene diol epoxide-DNA adducts as probes of adduct conformation," *Chem. Res. Toxicol.*, 15:118-126, 2002.

Judge et al., "Sequence-dependent stimulation of the mammalian innate immune response by synthetic siRNA," *Nat. Biotechnol.*, 23:457-62, 2005.

Kamat et al., "The role of relaxin in endometrial cancer," *Cancer Biol. Ther.*, 5:71-7, 2006.

Kaneda et al., "Increased expression of DNA cointroduced with nuclear protein in adult rat liver," *J. Mol. Med.*, 73:289-297, 1995.

Karashima et al., "Nuclear factor-kappaB mediates angiogenesis and metastasis of human bladder cancer through the regulation of interleukin-8," *Clin. Cancer Res.*, 9:2786-2797, 2003.

Kassim et al., "Vascular endothelial growth factor and interleukin-8 are associated with poor prognosis in epithelial ovarian cancer patients," *Clin. Biochem.*, 37:363-369, 2004.

Kato et al., "Expression of hepatitis B virus surface antigen in adult rat liver. Co-introduction of DNa and nuclear protein by a simplified liposome method," *J. Biol. Chem.*, 266:3361-3364, 1991.

Kim et al., "Expression of interleukin-8 correlates with angiogenesis, tumorigenicity, and metastasis of human prostate cancer cells implanted orthotopically in nude mice," *Neoplasia*, 3:33-42, 2001.

Koch et al., "Interleukin-8 as a macrophage-derived mediator of angiogenesis," *Science*, 258:1798-1801, 1992.

Kostarelos et al., "Binding and interstitial penetration of liposomes within avascular tumor spheroids," *Int. J. Cancer*, 112:713-21, 2004.

Krasnici et al., "Effect of the surface charge of liposomes on their uptake by angiogenic tumor vessels," *Int. J. Cancer*, 105:561-7, 2003.

Landen et al., "EphA2 as a target for ovarian cancer therapy," *Expert. Opin. Ther. Targets*, 9:1179-87, 2005.

Landen et al., "Intraperitoneal delivery of liposomal siRNA for therapy of advanced ovarian cancer," *Cancer Biol. Ther.*, 5:1708-1713, 2006.

Landen et al., "Therapeutic EphA2 gene targeting in vivo using neutral liposomal small interfering RNA delivery," *Cancer Res.*, 65:6910-18, 2005.

Lee et al., "Taxol-dependent transcriptional activation of IL-8 expression in a subset of human ovarian cancer," *Cancer Res.*, 56:1303-1308, 1996.

Leung and Whittaker, "RNA interference: from gene silencing to gene-specific therapeutics," *Pharmacol. Ther.*, 107:222-239, 2005.

Li et al., "Autocrine role of interleukin-8 in induction of endothelial cell proliferation, survival, migration and MMP-2 production and angiogenesis," *Angiogenesis*, 8:63-71, 2005.

Lokshin et al., "Circulating IL-8 and anti-IL-8 autoantibody in patients with ovarian cancer," *Gynecol. Oncol.*, 102:244-251, 2006.

Lu et al., "Gene alterations identified by expression profiling in tumor-associated endothelial cells from invasive ovarian carcinoma," *Cancer Res.*, 67:1757-68, 2007.

Luca et al., "Expression of interleukin-8 by human melanoma cells up-regulates MMP-2 activity and increases tumor growth and metastasis," *Am. J. Pathol.*, 151:1105-1113, 1997.

Matsushima and Oppenheim, "Interleukin 8 and MCAF: novel inflammatory cytokines inducible by IL 1 and TNF," *Cytokine*, 1:2-13, 1989.

Mian et al., "Fully human anti-interleukin 8 antibody inhibits tumor growth in orthotopic bladder cancer xenografts via down-regulation of matrix metalloproteases and nuclear factor-kappaB," *Clin. Cancer Res.*, 9:3167-3175, 2003.

Miller et al., "Liposome-cell interactions in vitro: effect of liposome surface charge on the binding and endocytosis of conventional and sterically stabilized liposomes," *Biochemistry*, 37:12875-83, 1998.

Murdoch et al., "Cxc chemokine receptor expression on human endothelial cells," *Cytokine*, 11:704-12, 1999.

Nicolau et al., "Liposomes as carriers for in vivo gene transfer and expression," *Methods Enzymol.*, 149:157-176, 1987.

Roebuck, "Regulation of interleukin-8 gene expression," *J. Interferon Cytokine Res.*, 19:429-438, 1999.

Schröder and Christophers, "Identification of C5ades arg and an anionic neutrophil-activating peptide (ANAP) in psoriatic scales," *J. Invest. Dermatol.*, 87:53-58, 1986.

Sioud and Sorensen, "Cationic liposome-mediated delivery of siRNAs in adult mice," *Biochem. Biophys. Res. Comm.*, 312:1220-1225, 2003.

Siwak et al., "The potential of drug-carrying immunoliposomes as anticancer agents," *Clin. Cancer Res.*, 8:955-56, 2002.

Sood et al., "Fluorescent temporin B derivative and its binding to liposomes," *J. Fluorec.*, 17:223-34, 2007.

Sood et al., "Interaction of kidney (Na + -K + )-ATPase with phospholipid model membrane systems," *Biochim. Biophys. Acta.*, 282:429-34, 1972.

Soutschek et al., "Therapeutic silencing of an endogenous gene by systemic administration of modified siRNAs," *Nature*, 432:173-178, 2004.

Szoka and Papahadjopoulos, "Procedure for preparation of liposomes with large internal aqueous space and high capture by reverse-phase evaporation," *Proc. Natl. Acad. Sci. USA*, 75:4194-4198, 1978.

Thurston et al., "Cationic liposomes target angiogenic endothelial cells in tumors and chronic inflammation in mice," *J. Clin. Invest.*, 101:1401-13, 1998.

Trevino et al., "Src activation of Stat3 is an independent requirement from NF-kappaB activation for constitutive IL-8 expression in human pancreatic adenocarcinoma cells," *Angiogenesis*, 9:101-110, 2006.

Wadhwa et al., "Vectors for RNA interference," *Curr. Opin. Mol. Ther.*, 6:367-72, 2004.

Walz et al., "Purification and amino acid sequencing of NAF, a novel neutrophil-activating factor produced by monocytes," *Biochem. Biophys. Res. Commun.*, 149:755-61, 1987.

Wong et al., "Appearance of beta-lactamase activity in animal cells upon liposome-mediated gene transfer," *Gene*, 10:87-94, 1980.

Xie et al., "Breast cancer. Cyr61 is overexpressed, estrogen-inducible, and associated with more advanced disease," *J. Biol. Chem.*, 276:14187-14194, 2001.

Xu and Fidler, "Interleukin 8: an autocrine growth factor for human ovarian cancer," *Oncol. Res.*, 12:97-106, 2000.

Xu et al., "Hypoxia-induced elevation in interleukin-8 expression by human ovarian carcinoma cells," *Cancer Res.*, 59:5822-5829, 1999.

Zhao et al., "Interaction of the antimicrobial peptide pheromone Plantaricin A with model membranes: implications for a novel mechanism of action," *Biochim. Biophys. Acta.*, 1758:1461-74, 2006.

Zimmerman et al., "RNAi-mediated gene silencing in non-human primates," *Nature*, 441:111-4, 2006.

International Preliminary Report on Patentability, issued in Int. App. No. PCT/US2008/055486, mailed Sep. 8, 2009.

* cited by examiner

*p<0.001 vs. other groups

|  |  | IL-8 expression | | p value |
|---|---|---|---|---|
|  |  | Low | High |  |
| Stage | I/II | 10 | 1 | 0.019 |
|  | III/IV | 49 | 42 |  |
| Grade | Low | 6 | 0 | 0.031 |
|  | High | 53 | 43 |  |
| Histology | Serous | 54 | 42 | 0.19 |
|  | Other | 5 | 1 |  |
| Ascites | Present | 34 | 29 | 0.24 |
|  | Absent | 25 | 13 |  |
| Cytoreduction | Optimal | 36 | 17 | 0.054 |
|  | Suboptimal | 23 | 24 |  |

FIG. 10

| Variable | HR (95% CI) | p value |
|---|---|---|
| High Stage | 2.35 (1.24–4.46) | 0.009 |
| High-Grade | 1.02 (0.49–2.09) | 0.96 |
| Serous Histology | 1.72 (0.94–3.14) | 0.08 |
| Ascites | 2.32 (1.12–4.50) | 0.02 |
| Optimal Cytoreduction | 0.61 (0.34–1.12) | 0.12 |
| High II-8 | 3.7 (2–6.8) | 0.001 |

FIG.12

THERAPEUTIC TARGETING OF INTERLEUKINS USING SIRNA IN NEUTRAL LIPOSOMES

This application is a national phase application under 35 U.S.C. §371 of International Application No. PCT/US2008/055486, filed Feb. 29, 2008, which claims the benefit of priority to U.S. provisional patent application Ser. No. 60/892,772, filed Mar. 2, 2007, the entire contents of each of which are hereby incorporated by reference herein in their entirety.

This invention was made with government support under CA083639 awarded by The National Institutes of Health. The government has certain rights in the invention.

BACKGROUND OF THE INVENTION

I. Field of the Invention

The present invention relates generally to the fields of molecular biology, RNA interference, and oncology. More particularly, the invention concerns compositions comprising an siRNA (or nucleic acid encoding an siRNA) and a lipid component, wherein the siRNA is targeted to a nucleic acid encoding an interleukin. The invention also generally pertains to methods of treating cancer in a subject involving administering to the subject an IL-8 antagonist.

II. Description of Related Art

Ovarian cancer remains a significant cause of death among women in the United States. Recurrence of cancer following treatment of primary disease with surgery and chemotherapy is common. Thus, there is the need for new therapeutic agents in order to improve survival rates and eventually cure patients from this deadly disease.

Interleukin-8 (IL-8) is a potent pro-angiogenic cytokine that is known to be overexpressed in human cancers, including ovarian carcinoma (Lokshin et al., 2006; Xie, 2001; Kassim et al., 2004, and Koch et al., 1992). IL-8 is a small (8 kDa) molecule secreted by multiple sources including monocytes, neutrophils, endothelial and mesothelial cells and is predominantly responsible for recruitment of neutrophils, T-cells, and basophils during immune system activation (Walz et al., 1987; Schroder and Christophers, 1986; Matsushima and Oppenheim, 1989). Activators of IL-8 include tumor necrosis factor-alpha (TNF-α) and interleukin-1β (IL-1β) (Matsushima and Oppenheim, 1989), acute infections (Roebuck, 1999), and external factors, such as chemicals, chemotherapeutic agents, UV light, and stressful environments resulting in hypoxia and acidosis (Xie, 2001; Roebuck, 1999; Xu et al., 1999; Xu and Fidler, 2000; Lee et al., 1996). The induction of IL-8 expression is mediated by factors including nuclear transcription factor, NF-κB; however, recent studies have shown that IL-8 expression can increase following activation of the Src/STAT3 pathway, independent of NF-κB involvement (Trevino et al., 2006).

IL-8 acts by binding to the seven-transmembrane, G-protein coupled receptors, CXCR1 and CXCR2. Both of these receptors are expressed on a majority of tumor cell types as well as human endothelial cells (Murdoch, 1999; Xu and Fidler, 2000). Previous studies have shown that increased IL-8 expression in vivo leads to enhanced tumor growth, angiogenesis, and metastases (Xu and Fidler, 2000; Karashima et al., 2003; Luca et al., 1997; Kim et al., 2001). In addition, IL-8 increased human endothelial cell proliferation, tubule formation, and survival (Li et al., 2005). Further, blocking IL-8 activity has been shown to lead to decreased tumor growth, microvessel density, and distant metastases (Huang et al., 2002; Mian et al., 2003). Ovarian cancer expresses high levels of IL-8 which has been shown to be associated with poor clinical outcome (Kassim et al., 2004).

Since its initial description in *C. elegans* (Fire, 1998) and mammalian cells (Elbashir et al., 2001), use of short interfering RNA (siRNA) as a method of gene silencing has rapidly become a powerful tool in protein function delineation, gene discovery, and drug development (Hannon, 2004).

Liposomes have been used previously for drug delivery (e.g., delivery of a chemotherapeutic). Liposomes (e.g., cationic liposomes) are described in PCT publications WO02/100435A1, WO03/015757A1, and WO04029213A2; U.S. Pat. Nos. 5,962,016, 5,030,453, and 6,680,068; and U.S. Patent Application 2004/0208921, all of which are hereby incorporated by reference in their entirety without disclaimer. A process of making liposomes is also described in WO04/002453A1. Furthermore, neutral lipids have been incorporated into cationic liposomes (e.g., Farhood et al., 1995).

Cationic liposomes have been used to deliver siRNA to various cell types (Sioud and Sorensen, 2003; U.S. Patent Application 2004/0204377; Duxbury et al., 2004; Donze and Picard, 2002). However, it is not clear if or to what degree neutral liposomes may be used deliver siRNA to a cell.

Neutral liposomes have been tested to a limited degree. Miller et al. (1998) evaluated the uptake of neutral unilamellar liposomes; however, this work observed that cationic liposomes are taken up by cells more efficiently than neutral liposomes, thus teaching away from the idea that neutral liposomes may be more effective than cationic liposomes. Neutral liposomes were used to deliver therapeutic antisense oligonucleotides in U.S. Patent Application 2003/0012812 and siRNA in WO 2006/113679.

SUMMARY OF THE INVENTION

The present invention concerns the inventors' identification of certain compositions that include an nucleic acid and a lipid component that can be applied in the treatment of disease. In some embodiments, the invention concerns methods of treating cancer that involve administering to a subject an antagonist of IL-8. For example, the inventors have discovered that siRNA targeted to the gene encoding IL-8 is an effective therapy of ovarian cancer.

The present invention generally concerns compositions that includes: (1) an inhibitory nucleic acid (e.g., siNA), wherein the nucleic acid inhibits the expression of a gene encoding an interleukin or encodes a nucleic acid that inhibits the expression of a gene encoding an interleukin; and (2) a lipid component that includes one or more phospholipids, wherein the lipid component has an essentially neutral charge.

In some embodiments, the inhibitory nucleic acid is a siRNA, or a nucleic acid encoding a siRNA. The interleukin can be any interleukin. For example, the interleukin may be IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17α, IL-17β, IL-18, IL-19, IL-20, IL-21, IL-22, IL-23, IL-24, IL-25, IL-26, IL-27, IL-28A, IL-28B, IL-29, IL-30, IL-31, or IL-32. In particular embodiments, the interleukin is IL-6, IL-12, or IL-8. In more particular embodiments, the interleukin is IL-8.

Inhibitory nucleic acids or "siNA", as used herein, is defined as a short interfering nucleic acid. An inhibitory nucleic acid includes a siRNA, a nucleic acid encoding a siRNA, or shRNA (short hairpin RNA), a ribozyme, or an antisense nucleic acid molecule that specifically hybridize to a nucleic acid molecule encoding a target protein or regulating the expression of the target protein. "Specific hybridization" means that the siRNA, shRNA, ribozyme or antisense nucleic acid molecule hybridizes to the targeted nucleic acid molecule and regulates its expression. Preferably, "specific hybridization" also means that no other genes or transcripts are affected. Examples of siNA include but are not limited to RNAi, double-stranded RNA, and siRNA. A siNA can inhibit the transcription or translation of a gene in a cell. A siNA may be from 16 to 1000 or more nucleotides long, and in certain embodiments from 18 to 100 nucleotides long. In certain embodiments, the siNA may be 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 200, 300, 500, or more nucleotides long. The siNA may comprise a nucleic acid and/or a nucleic acid analog. Typically, a siNA will inhibit the translation of a single gene within a cell; however, in certain embodiments, a siNA will inhibit the translation of more than one gene within a cell. In particular aspects, the double stranded nucleic acid can comprise 18 to 30, 19 to 25, 20 to 23, or 21 contiguous nucleobases or nucleobase pairs.

The siNA component comprises a single species of siRNA or more than one species of siRNA. In other embodiments, the siNA component comprises a 2, 3, 4 or more species of siRNA that target 1, 2, 3, 4, or more genes. In further embodiments, the nucleic acid component is encapsulated within the liposome or lipid component.

In some aspects the lipid component may be in the form of a liposome. The siNA (e.g., a siRNA) may be encapsulated in the liposome or lipid component, but need not be. Encapsulate refers to the lipid or liposome forming an impediment to free difussion into solution by an association with or around an agent of interest, e.g., a liposome may encapsulate an agent within a lipid layer or within an aqueous compartement inside or between lipid layers. In certain embodiments, the composition is comprised in a pharmaceutically acceptable carrier. The pharmaceutically acceptable carrier may be formulated for administration to a human subject or patient.

In certain embodiments, the lipid component has an essentially neutral charge because it comprises a neutral phospholipid or a net neutral charge. In certain aspects a neutral phospholipid may be a phosphatidylcholine, such as DOPC, egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, or dilinoleoylphosphatidylcholine. In other aspects the neutral phospholipid can be a phosphatidylethanolamine, such as dioleoylphosphatidylethanolamine ("DOPE"), distearoylphophatidylethanolamine ("DSPC"), dimyristoyl phosphatidylethanolamine ("DMPE"), dipalmitoyl phosphatidylethanolamine ("DPPE"), palmitoyloeoyl phosphatidylethanolamine ("POPE"), or lysophosphatidylethanolamine. In certain embodiments, the phospholipid component can comprise 1, 2, 3, 4, 5, 6, 7, 8, or more kinds or types of neutral phospholipid. In other embodiments, a phospholipid component can comprise 2, 3, 4, 5, 6 or more kinds or type of neutral phospholipids.

In certain embodiments, a lipid component can have an essentially neutral charge because it comprises a positively charged lipid and a negatively charged lipid. The lipid component may further comprise a neutrally charged lipid(s) or phospholipid(s). The positively charged lipid may be a positively charged phospholipid. The negatively charged lipid may be a negatively charged phospholipid. The negatively charged phospholipid may be a phosphatidylserine, such as dimyristoyl phosphatidylserine ("DMPS"), dipalmitoyl phosphatidylserine ("DPPS"), or brain phosphatidylserine ("BPS"). The negatively charged phospholipid may be a phosphatidylglycerol, such as dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), or dioleoylphosphatidylglycerol ("DOPG"). In certain embodiments, the composition further comprises cholesterol or polyethyleneglycol (PEG). In certain embodiments, a phospholipid is a naturally-occurring phospholipid. In other embodiments, a phospholipid is a synthetic phospholipid.

The composition may further comprise a chemotherapeutic or other anti-cancer agent, which may or may not be encasulated in a lipid component or liposome of the invention. For example, the chemotherapeutic agent may be docetaxel, paclitaxel, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristine, vinblastin, methotrexate, or combinations thereof. In particular embodiments, the chemotherapeutic agent is docetaxel.

The present invention also generally concerns a method of treating a human subject with cancer involving administering to the subject a pharmaceutically effective amount of an IL-8 antagonist. As used herein, an "IL-8 antagonist" refers to any agent that can reduce the expression of IL-8 or inhibit the function of IL-8. The cancer can be any type of cancer, such as breast cancer, lung cancer, prostate cancer, ovarian cancer, brain cancer, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. In particular embodiments, the cancer is ovarian cancer.

The IL-8 antagonist can be any type of molecule. For example, it can be a nucleic acid, a small molecule, a peptide, a polypeptide, or an antibody. The nucleic acid may be a DNA or an RNA. It may be an inhibitor nucleic acid (siNA), as discussed above. It may be single stranded or double stranded. In particular embodiments, the IL-8 antagonist is a RNA. In more particular embodiments, the RNA is a siRNA targeted to a gene that encodes an IL-8 polypeptide. In further embodiments, the IL-8 antagonist is a DNA. For example, the DNA may encoding a siRNA. In particular embodiments, the sense strand of the siRNA comprises SEQ ID NO:39, SEQ ID NO:41, SEQ ID NO:43, or SEQ ID NO:45. The siNA may be administered in any of the neutral lipid compositions as set forth above.

The present invention also generally pertains to methods of treating a subject with cancer involving administering to the subject a pharmaceutically effective amount of an IL-8 antagonist, wherein the IL-8 antagonist is a siNA. The siNA can be any of those nucleic acids discussed above. In particular embodiments, the sense strand of the siRNA comprises SEQ ID NO:39, SEQ NO:41, SEQ ID NO:43, or SEQ ID NO:45.

The present invention also generally pertains to methods of treating a subject with a disease involving administering to the subject a pharmaceutically effective amount of a composition comprising an inhibitory nucleic acid, wherein the nucleic acid inhibits the expression of a gene encoding an interleukin or encodes a nucleic acid that inhibits the expression of a gene encoding an interleukin; and (2) a lipid component. The disease can be any disease process that is known or suspected to be associated with increased expression or function of an interleukin. In some embodiments, the disease is a hyperproliferative disease, such as cancer. In some embodiments, the interleukin is IL-6, IL-8, or IL-12, and the disease is ovarian cancer. In more particular embodiments, the interleukin is IL-8 and the disease is ovarian cancer. In further embodiments, the interleukin is IL-1, IL-2, IL-2, IL-4, IL-5, IL-7, IL-9, IL-17, or IL-18, and disease is an inflammatory disease. For example, the inflammatory disease may be arthritis, allergic disease, a collagen vascular disease, or an infectious disease. Examples of collagen vascular disease include rheumatoid arthritis and systemic lupus erythematosus.

The infectious disease may be a bacterial infection, a viral infection, a fungal infection, or a parasitic infection. In some embodiments, the viral infection is due to HIV. In some embodiments, the method further includes identifying a subject in need of treatment. Such identification can be by any method known to those of ordinary skill in the art, such as based on clinical examination, based on identification of a particular stage or grade of tumor, and so forth.

In certain embodiments, the methods of the invention further comprise administering an additional therapy to the subject. The additional therapy may comprise administering a chemotherapeutic (e.g., paclitaxel or docetaxel), a surgery, a radiation therapy, an immunotherapy, and/or a gene therapy. In certain aspects the chemotherapy is docetaxel, paclitaxel, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin, methotrexate, or combinations thereof. In certain embodiments the chemotherapy is a taxane such as docetaxal or paclitaxel. The chemotherapy can be delivered before, during, after, or combinations thereof relative to a neutral lipid composition of the invention. A chemotherapy can be delivered within 0, 1, 5, 10, 12, 20, 24, 30, 48, or 72 hours or more of the neutral lipid composition. The neutral lipid composition, the second anti-cancer therapy, or both the neutral lipid composition and the anti-cancer therapy can be administered intratumorally, intravenously, intraperitoneally, orally or by various combinations thereof.

The therapeutic agents and compositions set forth herein can be administered to the patient using any technique known to those of ordinary skill in the art. For example, administration may be intravenously, intraperitoneally, intratracheally, intratumorally, intramuscularly, endoscopically, intralesionally, percutaneously, subcutaneously, regionally, or by direct injection or perfusion.

In particular embodiments, the method is a method of treating a subject with ovarian cancer comprising administering to the subject a pharmaceutically effective amount of an siRNA, wherein the siRNA is targeted to a gene that encodes an IL-8 polypeptide. In more particular embodiments, the method further involves administering a chemotherapeutic agent to the subject. The chemotherapeutic agent may be administered prior to the siRNA, concurrently with the siRNA, or following administration of the siRNA. The chemotherapeutic agent can be any of those agents discussed above and elsewhere in this specification. In particular embodiments, the chemotherapeutic agent is docetaxel.

The present invention also concerns a method of inhibiting angiogenesis in a subject comprising administering to the subject a pharmaceutically effective amount of a composition that includes a siRNA component and lipid component as set forth above, wherein the siRNA inhibits the expression of IL-8 in the subject.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A—SiRNA targeting IL-8 significantly decreased IL-8 mRNA expression in HeyA8 and SKOV3ip1 ovarian cancer cell lines using RT-PCR; FIG. 1B—ELISA analysis illustrating that secreted IL-8 protein levels were reduced by 80% following siRNA transfection in both HeyA8 and SKOV3ip1 cell lines; FIG. 1C—In vivo dose-response experiment demonstrated a significant reduction in IL-8 expression 48 hours following intraperitoneal IL-8 siRNA-DOPC treatment in HeyA8 tumors.

FIG. 2A—Enzyme-linked immunosorbent assay of circulating serum IL-8 levels during IL-8 siRNA- DOPC therapy in the HeyA8 model. Forty-eight hours after siRNA-DOPC injection, whole blood samples (from 4 mice per treatment group) were obtained from tail veins and pooled for analysis. Values represent mean serum IL-8 levels; error bars correspond to 95% CIs. FIG. 2B—Immunohistochemical analysis of IL-8 expression in HeyA8 tumors harvested at completion of IL-8 siRNA-DOPC therapy with or without docetaxel. Immunohistochemical staining represents cell nuclei and IL-8 in photoimages.

FIG. 4A—IL-8 siRNA-DOPC in combination with docetaxel therapy significantly reduced tumor burden (represented by average number of tumor nodules/mouse) in HeyA8 and SKOV3ip1 cell lines; FIG. 4B—IL-8 siRNA-DOPC reduced tumor burden in taxane resistant model.

FIG. 10. IL-8 expression relates to clinical outcome. Univariate analysis of IL-8 expression with clinical outcome variables in ovarian cancer.

FIG. 11A—Representative images of human ovarian tumors with low and high immunohistochemical staining for IL-8. Negative control represents a sample of ovarian cancer tissue used in the current study processed for immunohistochemistry with the secondary antibody alone. Immunohistochemistry staining of cell nuclei (blue) and IL-8 (brown) are represented in photoimages. FIG. 11B—Kaplan-Meier curves of disease-specific survival for patients whose ovarian tumors expressed high and low levels of IL-8. The log-rank test (two-sided) was used compare differences between groups. Survival probabilities and 95% CIs at 2 and 4 year analyses for the low IL-8 (2 years: 86.35%; CI=75.65% to 94.31%; 4 years: 43.76%; CI=24.14% to 64.46%) and high IL-8 (2 years: 43.45%; CI=28.49% to 59.04%; 4 years: 13.37%; CI=3.93% to 27.25%) groups.

FIG. 12. Table summarizing results of multivariate analysis discussed in Example 2.

DESCRIPTION OF ILLUSTRATIVE EMBODIMENTS

Figure 1A:
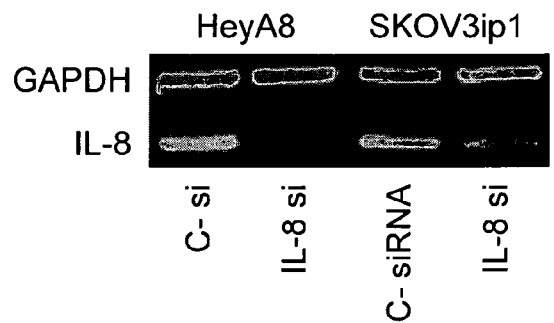
FIG. 1A, 1B, 1C. Silencing of IL-8 expression with siRNA in vitro.

The present invention provides compositions that include (1) an inhibitory nucleic acid, and (2) a lipid component comprising one or more phospholipids, wherein the lipid component has an essentially neutral charge. In certain embodiments the lipid component includes non-charged liposomes. The present invention also provides methods of treating a subject with cancer comprising administering to the subject a pharmaceutically effective amount of an IL-8 antagonist. The IL-8 antagonist may be an agent that reduces expression of IL-8 or reduces function or activity of IL-8. For example, the IL-8 antagonist may be an siRNA that is targeted to the gene that encodes IL-8.

The inventors have found that targeting IL-8 with siRNA-DOPC was effective in reducing the expression of IL-8 in an orthotopic ovarian cancer model. Furthermore, combination therapy with IL-8 siRNA-DOPC and docetaxel was highly effective in reducing tumor growth in chemotherapy-sensitive and resistant cell models. Reduction in MVD and tumor cell proliferation following IL-8 siRNA-DOPC therapy indicates that reduced IL-8 expression significantly affects the ability of tumors to develop a vascular network that supports tumor progression and spread. The inventors have developed additional gene silencing compositions and methods for use as an in vivo therapeutic, particularly with respect to using inhibitory nucleic acids such as short interfering RNA (siRNA).

III. Interleukins

Interleukins are the cytokines that act specifically as mediators between leucocytes. Table 1 lists interleukins, and includes GenBank Accession numbers of mRNA sequences from *homo sapiens*.

TABLE 1

| Interleukin | GenBank Accession No. | Sequence Identifier |
|---|---|---|
| IL-1α | NM 000575 | SEQ ID NO: 2 |
| IL-1β | NM 000576 | SEQ ID NO: 3 |
| IL-2 | NM 000584 | SEQ ID NO: 4 |
| IL-3 | NM 000588 | SEQ ID NO: 5 |
| IL-4 | BC 066278 | SEQ ID NO: 6 |
| IL-5 | NM 000879 | SEQ ID NO: 7 |
| IL-6 | NM 000600 | SEQ ID NO: 8 |
| IL-7 | NM 002185 | SEQ ID NO: 9 |
| IL-8 | NM 000584 | SEQ ID NO: 10 |
| IL-9 | NM 000590 | SEQ ID NO: 11 |
| IL-10 | NM 000572 | SEQ ID NO: 12 |
| IL-11 | NM 000641 | SEQ ID NO: 13 |
| IL-12 | EF 173865 | SEQ ID NO: 14 |
| IL-13 | NM 002188 | SEQ ID NO: 15 |
| IL-14 | NM 175852 | SEQ ID NO: 16 |
| IL-15 | NM 172174, | SEQ ID NO: 17 |
|  | NM 000585, | SEQ ID NO: 18 |
|  | NM 172200 | SEQ ID NO: 19 |
| IL-16 | NM 004513 | SEQ ID NO: 20 |
| IL-17α | NM 002190 | SEQ ID NO: 21 |
| IL-17β | NM 014443 | SEQ ID NO: 22 |
| IL-18 | NM 001562 | SEQ ID NO: 23 |
| IL-19 | NM 153758 | SEQ ID NO: 24 |
| IL-20 | NM 018724 | SEQ ID NO: 25 |
| IL-21 | BC 069124 | SEQ ID NO: 26 |
| IL-22 | NM 020525 | SEQ ID NO: 27 |
| IL-23 | NM 016584 | SEQ ID NO: 28 |
| IL-24 | NM 006850 | SEQ ID NO: 29 |
| IL-25 | NM 172314 | SEQ ID NO: 30 |
| IL-26 | NM 018402 | SEQ ID NO: 31 |
| IL-27 | NM 145659 | SEQ ID NO: 32 |
| IL-28A | NM 172138 | SEQ ID NO: 33 |
| IL-28B | NM 172139 | SEQ ID NO: 34 |
| IL-29 | NM 172140 | SEQ ID NO: 35 |
| IL-30 | BC 132998 | SEQ ID NO: 36 |
| IL-31 | NM 001012718 | SEQ ID NO: 37 |
| IL-32 | NM 033439 | SEQ ID NO: 38 |

Table 2 lists major source of particular interleukins, and lists major effects

| | Major source | Major effects |
|---|---|---|
| IL-1 | Macrophages | Stimulation of T cells and antigen-presenting cells. B-cell growth and anibody production. Promotes hematopoiesis (blood cell formation). |
| IL-2 | Activated T cells | Proliferation of activated T cells. |
| IL-3 | T lymphocytes | Growth of blood cell precursors. |
| IL-4 | T cells and mast cells | B-cell proliferation. IgE production. |
| IL-5 | T cells and mast cells | Eosinophil growth. |
| IL-6 | Activated T cells | Synergistic effects with IL-1 or TNFα. |
| IL-7 | thymus and bone marrow stromal cells | Development of T cell and B cell precursors. |
| IL-8 | Macrophages | Chemoattracts neutrophils. |
| IL-9 | Activated T cells | Promotes growth of T cells and mast cells. |
| IL-10 | Activated T cells, B cells and monocytes | Inhibits inflammatory and immune responses. |
| IL-11 | Stromal cells | Synergistic effects on hematopoiesis. |
| IL-12 | Macrophages, B cells | Promotes $T_H1$ cells while suppressing $T_H2$ functions |
| IL-13 | $T_H2$ cells | Similar to IL-4 effects |
| IL-15 | Epithelial cells and monocytes | Similar to IL-2 effects. |
| IL-16 | CD8 T cells | Chemoattracts CD4 T cells. |
| IL-17 | Activated memory T cells | Promotes T cell proliferation. |
| IL-18 | Macrophages | Induces IFNγ production. |

IV. IL-8 Antagonists

As discussed above, an "IL-8 antagonist" refers to any agent that can reduce the expression of IL-8 or inhibit the function of IL-8.

For example, "IL-8 antagonist" includes agents that can bind IL-8 such as anti-IL-8 antibodies. Also included as IL-8 antagonists are receptor molecules which bind specifically to IL-8. IL-8 antagonists also includes agents that can prevent or inhibit IL-8 synthesis. Other examples of IL-8 antagonists include agents that can prevent or inhibit IL-8 receptor signalling.

Particular IL-8 antagonists for inclusion in the methods set forth herein include inhibitory nucleic acids, such as siRNA, as discussed in greater detail in the specification below.

In particular embodiments, the IL-8 antagonist is an antibody. The term "antibody" is defined herein to include polyclonal antibodies, monoclonal antibodies (mAbs), chimeric antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques.

V. Therapeutic Gene Silencing

Since the discovery of RNAi by Fire and colleagues in 1981, the biochemical mechanisms have been rapidly characterized. Long double stranded RNA (dsRNA) is cleaved by Dicer, which is an RNAaseIII family ribonuclease. This process yields siRNAs of ~21 nucleotides in length. These siRNAs are incorporated into a multiprotein RNA-induced silencing complex (RISC) that is guided to target mRNA. RISC cleaves the target mRNA in the middle of the complementary region. In mammalian cells, the related microRNAs (miRNAs) are found that are short RNA fragments (~22 nucleotides). mRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

A. Delivery of siRNA or a Nucleic Acid Encoding Same

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004). While many of these approaches are successful for in vitro studies, in vivo delivery poses additional challenges based on the complexity of the tumor microenvironment.

Liposomes are a form of nanoparticles that are attractive carriers for delivering a variety of drugs into the diseased tissue. Optimal liposome size depends on the tumor target. In tumor tissue, the vasculature is discontinuous, and pore sizes vary from 100 to 780 nm (Siwak et al., 2002). By comparison, pore size in normal vascular endothelium is <2 nm in most tissues, and 6 nm in post-capillary venules. Most liposomes are 65-125 nm in diameter. Negatively charged liposomes were believed to be more rapidly removed from circulation than neutral or positively charged liposomes; however, recent studies have indicated that the type of negatively charged lipid affects the rate of liposome uptake by the reticuloendothelial system (RES). For example, liposomes containing negatively charged lipids that are not sterically shielded (phosphatidylserine, phosphatidic acid, and phosphatidylglycerol) are cleared more rapidly than neutral liposomes. Interestingly, cationic liposomes (1,2-dioleoyl-3-trimethylammonium-propane [DOTAP]) and cationic-liposome-DNA complexes are more avidly bound and internalized by endothelial cells of angiogenic blood vessels via endocytosis than anionic, neutral, or sterically stabilized neutral liposomes (Thurston et al., 1998; Krasnici et al., 2003). Cationic liposomes may not be ideal delivery vehicles for tumor cells because surface interactions with the tumor cells create an electrostatically derived binding-site barrier effect, inhibiting further association of the delivery systems with tumor spheroids (Kostarelos et al., 2004). However, neutral liposomes appear to have better intratumoral penetration. Toxicity with specific liposomal preparations has also been a concern. Cationic liposomes elicit dose-dependent toxicity and pulmonary inflammation by promoting release of reactive oxygen intermediates, and this effect is more pronounced with multivalent cationic liposomes than monovalent cationic liposomes such as DOTAP (Dokka et al., 2000). Neutral and negative liposomes do not appear to exhibit lung toxicity (Guitierrez-Puente et al., 1999). Cationic liposomes, while efficiently taking up nucleic acids, have had limited success for in vivo gene downregulation, perhaps because of their stable intracellular nature and resultant failure to release siRNA contents.

The inventors have selected lipids with neutral or lipid compositions with a neutalized charge, e.g., 1,2-dioleoyl-sn-glycero-3-phosphatidylcholine (DOPC), because of the neutral properties and success in delivering antisense oligonucleotides in vivo. Highly-efficient and efficacious in vivo siRNA delivery using neutral liposomes in an orthotopic model of advanced ovarian cancer has been described (Landen et al., 2005, which is incorporated herein by reference in its entirety). For example, intravenous injection of the DOPC-siRNA complex allowed a significantly greater degree of siRNA deposition into the tumor parenchyma than either delivery with cationic (positively charged) liposomes (DOTAP) or unpackaged "naked" siRNA. While the DOPC formulation delivered siRNA to over 30% of cells in the tumor parenchyma, naked siRNA was delivered only to about 3% of cells, and DOTAP delivered siRNA only to tumor cells immediately adjacent to the vasculature.

Although siRNA appears to be more stable than antisense molecules, serum nucleases can degrade siRNAs (Leung and Whittaker, 2005). Thus, several research groups have developed modifications such as chemically stabilized siRNAs with partial phosphorothioate backbone and 2'-O-methyl sugar modifications or boranophosphate siRNAs (Leung and Whittaker, 2005). Elmen and colleagues modified siRNAs with the synthetic RNA-like high affinity nucleotide analogue, Locked Nucleic Acid (LNA), which significantly enhanced the serum half-life of siRNA and stabilized the structure without affecting the gene-silencing capability (Elmen et al., 2005). Alternative approaches including chemical modification (conjugation of cholesterol to the 3' end of the sense strand of siRNA by means of a pyrrolidine linker) may also allow systemic delivery without affecting function (Soutschek et al., 2004). Aspects of the present invention can use each of these modification strategies in combination with the compositions and methods described.

VI. Lipid Preparations

The present invention provides methods and compositions for associating an inhibitory nucleic acid that inhibits the expression of an interleukin, such as a siNA (e.g., a siRNA) with a lipid and/or liposome. The siNA may be encapsulated in the aqueous interior of a liposome, interspersed within the lipid bilayer of a liposome, attached to a liposome via a linking molecule that is associated with both the liposome and the polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The liposome or liposome/siNA associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine (DOPC).

"Liposome" is a generic term encompassing a variety of unilamellar, multilamellar, and multivesicular lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as non-uniform aggregates of lipid molecules. Also contemplated are lipofectamine-nucleic acid complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemaglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer of a polynucleotide in vitro and in vivo, then they are applicable for the present invention.

A. Neutral Liposomes

"Neutral liposomes or lipid composition" or "non-charged liposomes or lipid composition," as used herein, are defined as liposomes or lipid compositions having one or more lipids that yield an essentially-neutral, net charge (substantially non-charged). By "essentially neutral" or "essentially non-charged", it is meant that few, if any, lipids within a given population (e.g., a population of liposomes) include a charge that is not canceled by an opposite charge of another component (e.g., fewer than 10% of components include a non-canceled charge, more preferably fewer than 5%, and most preferably fewer than 1%). In certain embodiments of the present invention, a composition may be prepared wherein the lipid component of the composition is essentially neutral but is not in the form of liposomes.

In certain embodiments, neutral liposomes or lipid compositions may include mostly lipids and/or phospholipids that are themselves neutral. In certain embodiments, amphipathic lipids may be incorporated into or used to generate neutral liposomes or lipid compositions. For example, a neutral liposome may be generated by combining positively and negatively charged lipids so that those charges substantially cancel one another. For such a liposome, few, if any, charged lipids are present whose charge is not canceled by an oppositely-charged lipid (e.g., fewer than 10% of charged lipids have a charge that is not canceled, more preferably fewer than 5%, and most preferably fewer than 1%). It is also recognized that the above approach may be used to generate a neutral lipid composition wherein the lipid component of the composition is not in the form of liposomes.

In certain embodiments, a neutral liposome may be used to deliver a siRNA. The neutral liposome may contain a siRNA directed to the suppression of translation of a single gene, or the neutral liposome may contain multiple siRNA that are directed to the suppression of translation of multiple genes. Further, the neutral liposome may also contain a chemotherapeutic in addition to the siRNA; thus, in certain embodiments, chemotherapeutic and a siRNA may be delivered to a cell (e.g., a cancerous cell in a human subject) in the same or separate compositions. An advantage to using neutral liposomes is that, in contrast to the toxicity that has been observed in response to cationic liposomes, little to no toxicity has yet been observed as a result of neutral liposomes.

B. Phospholipids

Lipid compositions of the present invention may comprise phospholipids. In certain embodiments, a single kind or type of phospholipid may be used in the creation of lipid compositions such as liposomes (e.g., DOPC used to generate neutral liposomes). In other embodiments, more than one kind or type of phospholipid may be used.

Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes or lipid compositions. In certain embodiments, a lipid that is not a phospholipid (e.g., a cholesterol) can also be used Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidylethanolamine are not used in certain embodiments as the primary phosphatide (i.e., constituting 50% or more of the total phosphatide composition) because this may result in instability and leakiness of the resulting liposomes.

C. Production of Liposomes

Liposomes and lipid compositions of the present invention can be made by different methods. For example, a nucleotide (e.g., siRNA) may be encapsulated in a neutral liposome using a method involving ethanol and calcium (Bailey and Sullivan, 2000). The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Lipids suitable for use according to the present invention can be obtained from commercial sources. For example, dimyristyl phosphatidylcholine ("DMPC") can be obtained from Sigma Chemical Co., dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol.

Liposomes within the scope of the present invention can be prepared in accordance with known laboratory techniques. In certain embodiments, liposomes are prepared by mixing liposomal lipids, in a solvent in a container (e.g., a glass, pear-shaped flask). The container will typically have a volume ten-times greater than the volume of the expected suspension of liposomes. Using a rotary evaporator, the solvent may be removed at approximately 40° C. under negative pressure. The solvent may be removed within about 5 minutes to 2 hours, depending on the desired volume of the liposomes. The composition can be dried further in a desiccator under vacuum. Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

Liposomes can also be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

Dried lipids or lyophilized liposomes may be dehydrated and reconstituted in a solution of inhibitory peptide and diluted to an appropriate concentration with a suitable solvent (e.g., DPBS). The mixture may then be vigorously shaken in a vortex mixer. Unencapsulated nucleic acid may be removed by centrifugation at 29,000 g and the liposomal pellets washed. The washed liposomes may be resuspended at an appropriate total phospholipid concentration (e.g., about 50-200 mM). The amount of nucleic acid encapsulated can be determined in accordance with standard methods. After determination of the amount of nucleic acid encapsulated in the liposome preparation, the liposomes may be diluted to appropriate concentrations and stored at 4° C. until use.

VII. Inhibition of Gene Expression siNA (e.g., siRNA) are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Within a siNA, the components of a nucleic acid need not be of the same type or homogenous throughout (e.g., a siNA may comprise a nucleotide and a nucleic acid or nucleotide analog). Typically, siNA form a double-stranded structure; the double-stranded structure may result from two separate nucleic acids that are partially or completely complementary. In certain embodiments of the present invention, the siNA may comprise only a single nucleic acid (polynucleotide) or nucleic acid analog and form a double-stranded structure by complementing with itself (e.g., forming a hairpin loop). The double-stranded structure of the siNA may comprise 16, 20, 25, 30, 35, 40, 45, 50, 60, 65, 70, 75, 80, 85, 90 to 100, 150, 200, 250, 300, 350, 400, 450, 500 or more contiguous nucleobases, including all ranges therebetween. The siNA may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

A. RNA Interference

Agents of the present invention useful for practicing the methods of the present invention include, but are not limited to siRNAs. Typically, introduction of double-stranded RNA (dsRNA), which may alternatively be referred to herein as small interfering RNA (siRNA), induces potent and specific gene silencing, a phenomena called RNA interference or RNAi. This phenomenon has been extensively documented in the nematode *C. elegans* (Fire et al., 1998), but is widespread in other organisms, ranging from trypanosomes to mouse. Depending on the organism being discussed, RNA interference has been referred to as "cosuppression," "post-transcriptional gene silencing," "sense suppression," and "quelling." RNAi is an attractive biotechnological tool because it provides a means for knocking out the activity of specific genes.

In designing RNAi there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80, 85, 90, 95, 98,% or even 100% identity between the sequence of the siRNA and the gene to be inhibited. Sequences less than about 80% identical to the target gene are substantially less effective. Thus, the greater homology between the siRNA and the interleukin gene to be inhibited, the less likely expression of unrelated genes will be affected.

In addition, the size of the siRNA is an important consideration. In some embodiments, the present invention relates to siRNA molecules that include at least about 19-25 nucleotides, and are able to modulate the gene expression an interleukin such as IL-8. In the context of the present invention, the siRNA is preferably less than 500, 200, 100, 50 or 25 nucleotides in length. More preferably, the siRNA is from about 19 nucleotides to about 25 nucleotides in length.

siRNA can be obtained from commercial sources, natural sources, or can be synthesized using any of a number of techniques well-known to those of ordinary skill in the art. For example, one commercial source of predesigned siRNA is Ambion®, Austin, Tex.

In one aspect, the invention generally features an isolated siRNA molecule of at least 19 nucleotides, having at least one strand that is substantially complementary to at least ten but no more than thirty consecutive nucleotides an interleukin, and that reduces the expression of the interleukin. In a preferred embodiment of the present invention, the siRNA molecule has at least one strand that is substantially complementary to at least ten but no more than thirty consecutive nucleotides of the mRNA for human IL-8 (GenBank accession no. NM 000584; herein SEQ ID NO:10). Each Genbank accession is incorporated herein by reference in its entirety. In certain embodiments of the present invention, the sense strand of the siRNA nucleic acid sequence targets to IL-8 and comprises SEQ ID NO:39 and the antisense strand comprises SEQ ID NO:40. In further embodiments, the sense strand of the siRNA that targets IL-8 comprises SEQ ID NO:41 and the antisense strand comprises SEQ ID NO:42. In further embodiments, the sense strand of the siRNA that targets IL-8 comprises SEQ ID NO:43 and the antisense strand comprises SEQ ID NO:44. In still further embodiments, the sense strand of the siRNA that targets IL-8 comprises SEQ ID NO:45 and the antisense strand comprises SEQ ID NO:46.

In another preferred embodiment, the siRNA molecule is at least 75, 80, 85, or 90% homologous, preferably 95%, 99%, or 100% homologous, to at least 10 contiguous nucleotides of the nucleic acid sequences shown in SEQ ID NO:10 or SEQ ID NO:1. Without undue experimentation and using the disclosure of this invention, it is understood that additional siRNAs can be designed and used to practice the methods of the invention.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Application Publication 20040019001 and U.S. Pat. No. 6,673,611 (each of which is incorporated by reference in its entirety). Collectively, all such altered nucleic acids or RNAs described above are referred to as modified siRNAs.

Preferably, RNAi is capable of decreasing the expression of an interleukin, such as IL-8, by at least 10%, 20%, 30%, or 40%, more preferably by at least 50%, 60%, or 70%, and most preferably by at least 75%, 80%, 90%, 95% or more.

Certain embodiments of the present invention pertain to methods of inhibiting expression of a gene encoding an interleukin in a cell. Introduction of siRNA into cells can be achieved by methods known in the art, including for example, microinjection, electroporation, or transfection of a vector comprising a nucleic acid from which the siRNA can be transcribed. Alternatively, a siRNA can be directly introduced into a cell in a form that is capable of binding to target mRNA transcripts. To increase durability and membrane-permeability the siRNA may be combined or modified with liposomes, poly-L-lysine, lipids, cholesterol, lipofectine or derivatives thereof. In certain aspects cholesterol-conjugated siRNA can be used (see, Song et al., 2003).

VIII. Nucleic Acids

The present invention provides methods and compositions for the delivery of siNA via neutral liposomes. Because a siNA is composed of a nucleic acid, methods relating to nucleic acids (e.g., production of a nucleic acid, modification of a nucleic acid, etc.) may also be used with regard to a siNA.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double stranded nucleic acids are formed by fully complementary binding, although in some embodiments a double stranded nucleic acid may formed by partial or substantial complementary binding. Thus, a nucleic acid may encompass a double-stranded molecule that comprises one or more complementary strand(s) or "complement(s)" of a particular sequence, typically comprising a molecule. As used herein, a single stranded nucleic acid may be denoted by the prefix "ss" and a double stranded nucleic acid by the prefix "ds".

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446, 137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moeity that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR™, to reduce false positives and discriminate between single base mutants, as described in U.S. Pat. No. 5,891,625. Other modifications and uses of nucleic acid analogs are known in the art, and it is anticipated that these techniques and types of nucleic acid analogs may be used with the present invention. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. Application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

A nucleic acid may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

G. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suit a particular application.

IX. Cancer

The present invention may be used to treat a disease, such as cancer. For example, a siRNA may be delivered via a non-charged liposome to treat a cancer. The cancer may be a solid tumor, metastatic cancer, or non-metastatic cancer. In certain embodiments, the cancer may originate in the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In certain embodiments, the cancer is human ovarian cancer. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia;

basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, and/or a neurodegenerative disease).

X. Pharmaceutical Preparations

Where clinical application of non-charged lipid component (e.g., in the form of a liposome) containing a siNA is undertaken, it will generally be beneficial to prepare the lipid complex as a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The phrases "pharmaceutical or pharmacologically acceptable" refers to molecular entities and compositions that do not produce an adverse, allergic or other untoward reaction when administered to an animal, such as a human, as appropriate. The preparation of a pharmaceutical composition that contains at least one non-charged lipid component comprising a siNA or additional active ingredient will be known to those of skill in the art in light of the present disclosure, as exemplified by Remington: The Science and Practice of Pharmacy, 21st, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 μg/kg/body weight to about 100 mg/kg/body weight, about 5 microgram/kg/body weight to about 500 milligram/kg/body weight, etc., can be administered.

A gene expression inhibitor may be administered in a dose of 1, 2, 3, 4, 5, 6, 7, 8, 9, 10, 15, 20, 25, 30, 40, 50, 60, 70, 80, 90, 100 or more μg of nucleic acid per dose. Each dose may be in a volume of 1, 10, 50, 100, 200, 500, 1000 or more μl or ml.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

XI. Combination Treatments

In certain embodiments, the compositions and methods of the present invention involve an inhibitor of gene expression, or construct capable of expressing an inhibitor of gene expression, in combination with a second or additional therapy. The methods and compositions including combination therapies enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an inhibitor of gene expression and a second therapy. A tissue, tumor, or cell can be contacted with one or more compositions or pharmacological formulation(s) including one or more of the agents (i.e., inhibitor of gene expression or an anti-cancer agent), or by contacting the tissue, tumor, and/or cell with two or more distinct compositions or formulations, wherein one composition provides 1) an inhibitor of gene expression; 2) an anti-cancer agent, or 3) both an inhibitor of gene expression and an anti-cancer agent. Also, it is contemplated that such a combination therapy can be used in conjunction with a chemotherapy, radiotherapy, surgical therapy, or immunotherapy.

An inhibitor of gene expression may be administered before, during, after or in various combinations relative to an anti-cancer treatment. The administrations may be in intervals ranging from concurrently to minutes to days to weeks. In embodiments where the inhibitor of gene expression is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the inhibitor of gene expression therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For the example below an inhibitor of gene expression therapy is "A" and an anti-cancer therapy is "B":

```
A/B/A  B/A/B  B/B/A  A/A/B  A/B/B  B/A/A  A/B/B/B
B/A/B/B  B/B/B/A  B/B/A/B  A/A/B/B  A/B/A/B  A/B/B/A
B/B/A/A  B/A/B/A  B/A/A/B  A/A/A/B  B/A/A/A  A/B/A/A
A/A/B/A
```

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

A. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

C. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gen silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

D. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

XII. Kits and Diagnostics

In various aspects of the invention, a kit is envisioned containing therapeutic agents and/or other therapeutic and delivery agents. In some embodiments, the present invention contemplates a kit for preparing and/or administering a therapy of the invention. The kit may comprise reagents capable of use in administering an active or effective agent(s) of the invention. Reagents of the kit may include at least one inhibitor of gene expression, one or more lipid component, one or more anti-cancer component of a combination therapy, as well as reagents to prepare, formulate, and/or administer the components of the invention or perform one or more steps of the inventive methods.

In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods, and will follow substantially the same procedures as described herein or are known to those of ordinary skill.

XIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effects of IL-8 Targeted Therapy with Liposome Incorporated siRNA on Ovarian Cancer Growth Methods Cell lines and cultures. The derivation and source of the epithelial ovarian cancer cell lines HeyA8 and SKOV3ip1 have been previously described (Halder et al., 2006; Landen et al., 2005). The taxane-resistant cell line, SKOV3ip2.TR (a gift from Dr. Isaiah J. Fidler, M.D. Anderson Cancer Center [MDACC], Houston, Tex.), was derived from the SKOV3ip1 cells following serial passages in media containing paclitaxel. All cell lines were maintained and propagated in RPMI-1640 media supplemented with 15% fetal bovine serum and 0.1% gentamicin sulfate (Gemini Bioproducts, Calabasas, Calif.). SKOV3ip2.TR media also contained 100-150 ng/ml paclitaxel. All experiments were performed at 60-80% confluency and cell lines routinely tested for *Mycoplasma*. For in vivo experiments, cells were trypsinized, centrifuged at 1000 rpm at 4° C. for 7 minutes, washed twice with HBSS, and resuspended at a concentration of $1.25 \times 10^6$ cells/ml (HeyA8) and $5 \times 10^6$ cells/ml (SKOV3ip1 and SKOV3ip2.TR).

SiRNA and in vitro transfections. IL-8 targeting siRNA purchased from Dharmacon (Lafayette, Colo.) was used to silence IL-8 expression in ovarian cancer cell lines (target sequence: GCCAAGGAGUGCUAAAGAA—SEQ ID NO:1). The sequence of the sense strand of the IL-8 siRNA is GCCAAGGAGUGCUAAAGAAUU (SEQ ID NO:39) and the sequence of the antisense strand of the IL-8 siRNA is UUCUUUAGCACUCCUUGGCUU (SEQ ID NO:40). Control siRNA (target sequence: UUCUCCGAACGUGUCACGU—SEQ ID NO:47; confirmed to demonstrated no sequence homology with any known human mRNA by BLAST analysis) was used as controls for all experiments. For in vitro transfections, $2 \times 10^5$ cells/well were plated into 6-well plates. The following day, cells were washed with PBS and incubated with 5 μg siRNA (IL-8 or control) with 30 μl of RNAiFect transfection reagent (Qiagen, Valencia, Calif.) in serum-containing media overnight at 37° C. Media was changed 24 hours after transfection and replaced with appropriate media.

Preparation of liposomal siRNA for in vivo delivery. For all in vivo experiments, siRNA constructs were incorporated into neutral liposomes (DOPC: 1,2-dioleoyl-sn-glycero-3-phosphatidylcholine), lyophilized, and stored at −20° C. (Landen et al., 2005). Prior to in vivo delivery, siRNA-DOPC preparations were resuspended with PBS to appropriate concentrations.

IL-8 siRNA therapy in an orthotopic murine ovarian cancer model. Female athymic nude mice were purchased from the National Cancer Institute-Frederick Cancer Research and Development Center (Frederick, Md.) and housed in specific pathogen-free conditions. They were cared for in accordance with the guidelines set forth by the American Association for Accreditation for Laboratory Animal Care and the U.S. Public Health Service Policy on Human Care and Use of Laboratory Animals, and all studies were approved and supervised by the MDACC Institutional Animal Care and Use Committee.

Development and characterization of the orthotopic murine model of advanced ovarian cancer used in these experiments has been previously described (Halder et al., 2006; Landen et al., 2005). Prior to initiating therapy trials, an in vivo dose-response experiment was performed to determine the optimal dose of IL-8 siRNA in DOPC (IL-8 siRNA-DOPC) needed to efficiently reduce IL-8 expression in the murine ovarian cancer model. Approximately 14 days after intraperitoneal (i.p.) HeyA8 cell line injection (when tumors were palpable) mice were injected i.p. with a single dose of either 3.5 or 5.0 μg/mouse (200 μl injection) of IL-8 siRNA-DOPC. Mice were sacrificed 48, 96, and 144 hours after siRNA-DOPC delivery and tumors were fixed in formalin for paraffin embedding or snap frozen in optimal cutting medium (OCT; Miles, Inc., Elkhart, Ind.) for frozen slide preparation. Immunohistochemical analysis of IL-8 expression after IL-8 siRNA-DOPC injection was performed to determine the timing and duration of IL-8 silencing. Next, therapy trials were designed to test the effects of IL-8 siRNA-DOPC alone and in combination with docetaxel. One week after cell line injection (HeyA8, SKOV3ip1, or SKOV3ip2.TR) mice were randomized into 5 groups (10 mice/group) and treated accordingly: empty liposomes, control siRNA-DOCP, IL-8 siRNA-DOPC, control siRNA-DOPC plus 50 μg of docetaxel (ip; 35 μg for SKOV3ip1 and SKOV3ip2.TR models), and IL-8 siRNA-DOPC plus docetaxel. Mice were monitored daily for signs of adverse effects and sacrificed when moribund. Tumor weights, number of tumor nodules, pattern of disease spread, presence and amount of ascites, and mouse weights were recorded at necropsy. Excised tumors were stored as described above.

mRNA and protein IL-8 expression analysis for in vitro transfections. The expression of IL-8 in vitro was determined with RT-PCR and ELISA 36-48 hours after siRNA transfection. For RT-PCR analysis, RNA was isolated according to manufacturer's protocol (Ambion RNAqueous Kit, Ambion, Austin, Tex.), transcribed into cDNA, and amplified: 94° C.×2 min, 94° C.×30 sec, 61° C.×30 sec, 72° C. 2 min, repeated for 21 cycles, and 72° C.×7 min (Primers: IL-8 sense CTTCTAGGACAAGAGCCAGGAAGAAACCAC (SEQ ID NO:48); IL-8 anti-sense GTCCAGACAGAGCTGTCT-TCCATCAGAAAG (SEQ ID NO:49); GAPDH sense GAGCCACATCGCTCAGAC (SEQ ID NO:50); GAPDH anti-sense CTTCTCATGGTTCACACCC (SEQ ID NO:51)). For ELISA, cells were treated with serum-free media day prior to analysis and IL-8 protein levels were quantified using a commercially available ELISA kit (R&D Systems, Minneapolis, Minn.). All experiments were performed in duplicate and control siRNA was used for comparison.

Analysis of IL-8 expression for in vivo experiments. The expression of IL-8 in circulating plasma was determined two weeks into IL-8 siRNA-DOPC therapy (ELISA) and in tumor tissue at the completion of each therapy experiment by immunohistochemistry (IHC). For plasma analysis, whole blood was obtained from mice (4/group) via tail vein, centrifuged at 9000 rpm at 4° C. for 2 min, and plasma aliquots were analyzed by ELISA according to manufacturer's protocol. IHC analysis of tumors was performed on 8-micron thick paraffin embedded slides. Slides were deparaffinized (xylene) and hydrated (alcohol) to PBS. Antigen retrieval was performed with pepsin (Biomeda, Foster City, Calif.) incubation at 37° C. for 20 minutes. Following PBS wash, slides were blocked for endogenous peroxidases with 3% $H_2O_2$, washed with PBS, blocked with 5% normal horse serum (NHS) and 1% normal goat serum (NGS) for 20 minutes at room temperature (RT), and incubated with a rabbit polyclonal anti-human IL-8 primary antibody (1:25; Biosource Int., Camarillo, Calif.) at 4° C. overnight. The following day, slides were incubated with appropriate horseradish peroxidase (HRP) secondary antibody for 1 hour at RT, detected with 3,3'-diaminobenzidine (DAB; Phoenix Biotechnologies, Huntsville, Ala.) for 8 minutes, and counterstained with Gill No. 3 hematoxylin (Sigma, ST. Louis, Mo.) for 20-30 seconds.

Analysis of tumor microvessel density (CD31) and proliferation (PCNA). Microvessel density analysis was performed by immunostaining for CD31 antigen in orthotopic tumors as previously described (Halder et al., 2006). Briefly, frozen slides were rehydrated in acetone, blocked for endogenous peroxidases with $H_2O_2$ in methanol, and incubated overnight at 4° C. with rat anti-mouse m-CD31 antibodies (1:800; BD Bioscience, Pharmingen, San Jose, Calif.). The following day, slides were incubated with appropriate secondary antibody and detected with DAB substrate. Proliferation was assessed by staining for PCNA on paraffin slides as previously reported (Halder et al., 2006). After deparaffinization and rehydration, slides were heated in microwave at 98° C. for 10 min in 0.1M citrate buffer (pH 6.0) for antigen retrieval, blocked for endogenous peroxidases, and then incubated with fragment blocker (1:10; Jackson Immunoresearch Lab., West Grove, Pa.) overnight at 4° C. to reduce murine antigen interference. Following day, slides were incubated with primary antibody (1:50; anti-PCNA, PC-10, mouse IgG, Dako, Carpinteria, Calif.) for 4 hours at RT, washed with PBS, and re-incubated for 1 hour at RT with appropriate secondary. Detection was performed with DAB substrate. Quantification of MVD and proliferation was performed as previously described (Halder et al., 2006).

Statistics. Mouse and tumor weights for each group were compared using the Student's t test for comparing two groups and by ANOVA for multiple group comparisons. For values that were not normally distributed, the Mann-Whitney rank sum test was used. A p-value of less than 0.05 was considered statistically significant.

Results

Figure 1B:
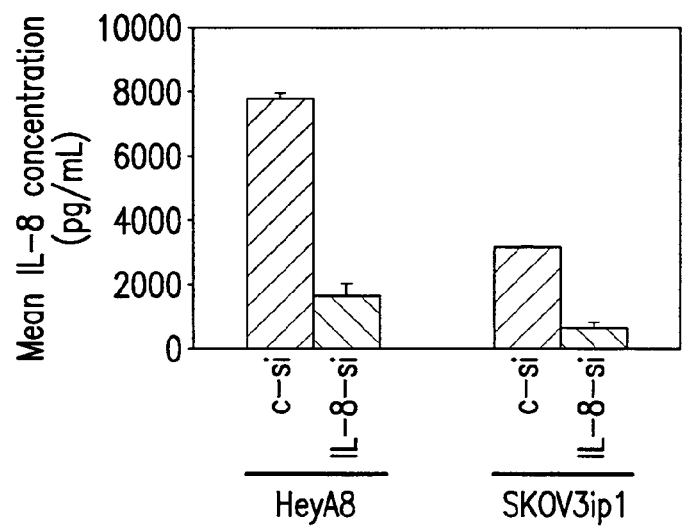
Figure 1C:
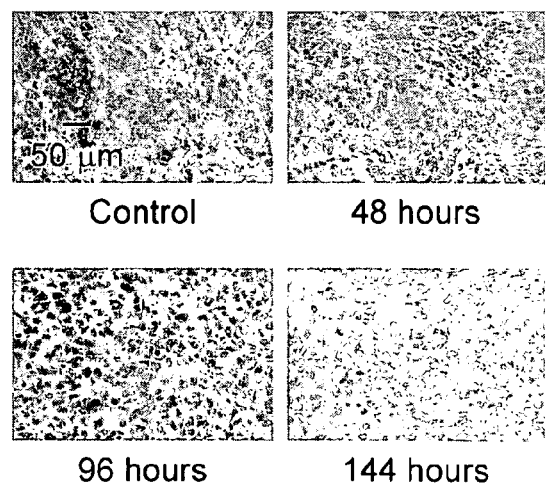

In vitro and in vivo reduction of IL-8 expression with siRNA. Prior to performing in vivo experiments targeting IL-8, the efficacy of silencing IL-8 in vitro was performed using HeyA8 and SKOV3ip1 ovarian cancer cell lines. Approximately 36-48 hours after siRNA transfection, appropriate samples were collected for RT-PCR and ELISA analyses to confirm IL-8 silencing. Compared to control siRNA, IL-8 mRNA expression was significantly reduced in both HeyA8 and SKOV3ip1 cancer cell lines (FIG. 1A). Furthermore, IL-8 protein levels were reduced by 79% and 81% in HeyA8 and SKOVip1, respectively (FIG. 1B). To test the duration of IL-8 siRNA silencing in vitro, media was collected at various time points following siRNA transfection of HeyA8 cells. Maximum down regulation of IL-8 was demonstrated at 48 hours after transfection before returning to baseline by 96 hours (FIG. 1C).

Figure 2A:
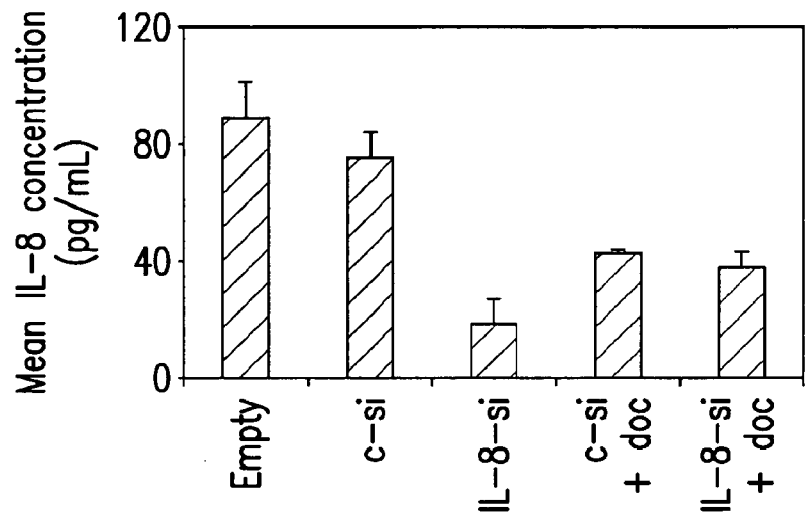
FIG. 2A, 2B.
Figure 2B:
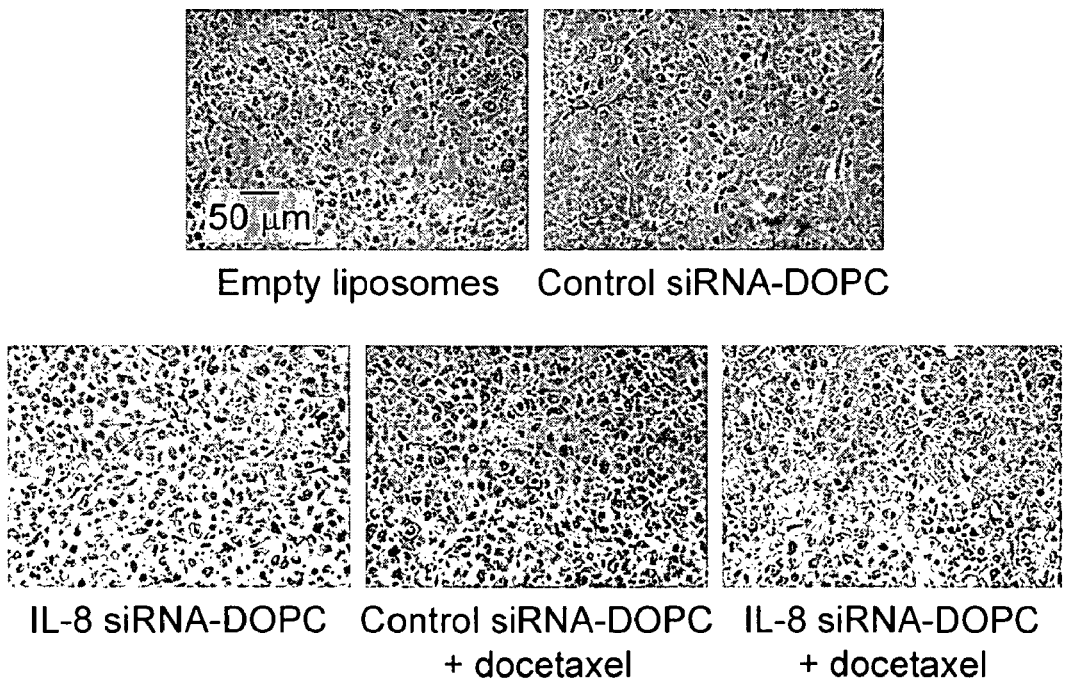

To determine whether the IL-8 siRNA constructs effectively reduced IL-8 expression in an orthotopic murine ovarian cancer model, dose-response experiments with IL-8 siRNA-DOPC treatments were performed. Compared to controls, 3.5 μg and 5.0 μg of IL-8 siRNA-DOPC significantly reduced IL-8 expression 48 hours after injection before returning to baseline at 6 days following injection (FIG. 1C). Therefore, based on these observations a twice weekly dosing of 3.5 μg IL-8 siRNA-DOPC regimen was used for future therapy experiments. To confirm downregulation of IL-8 during therapy experiments, circulating IL-8 levels were measured 48 hours after siRNA injections and tumor tissue IL-8 expression was measured at the completion of therapy experiments. Compared to control arms, IL-8 siRNA-DOPC significantly reduced plasma IL-8 levels by 80% in mice bearing HeyA8 tumors (FIG. 2A, 2B). In the both docetaxel treated arms, IL-8 levels were reduced compared to controls, however, increased compared to the IL-8 siRNA-DOPC alone arm. Compared to orthotopic tumors from control mice, IL-8 expression was reduced in the IL-8 siRNA-DOCP arm as well as the combination treatment of IL-8 siRNA-DOPC plus docetaxel arm.

Figure 3A:
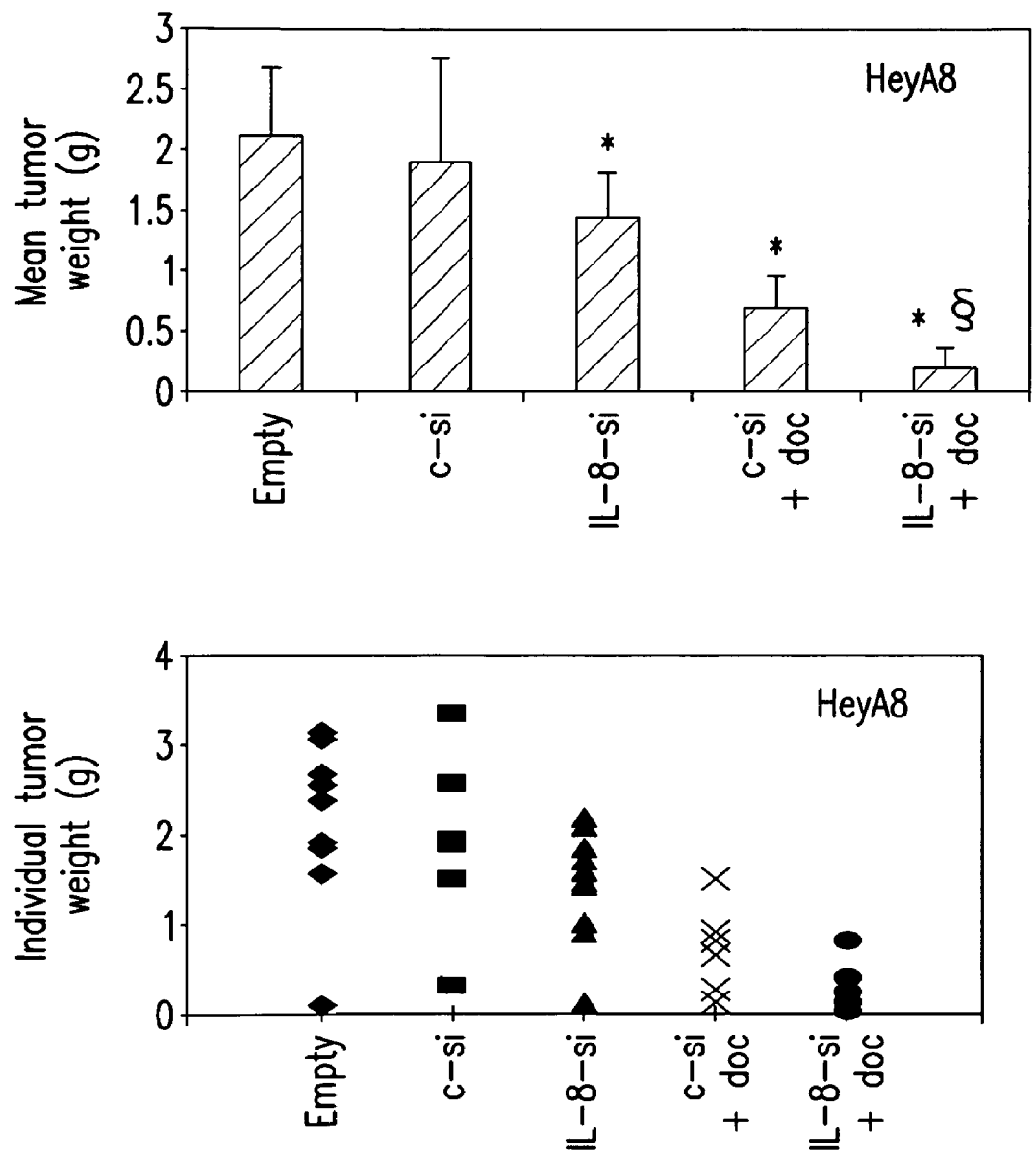
FIG. 3A, 3B, 3C—Effects of IL-8 siRNA-DOPC on tumor growth. IL-8 siRNA-DOPC plus docetaxel was highly effective in reducing tumor growth in HeyA8 (FIG. 3A), SKOV3ip1 (FIG. 3B), and the taxane-resistant ovarian cancer cell line SKOV3ip2.TR (FIG. 3C). Error bars represent SEM.
Figure 3B:
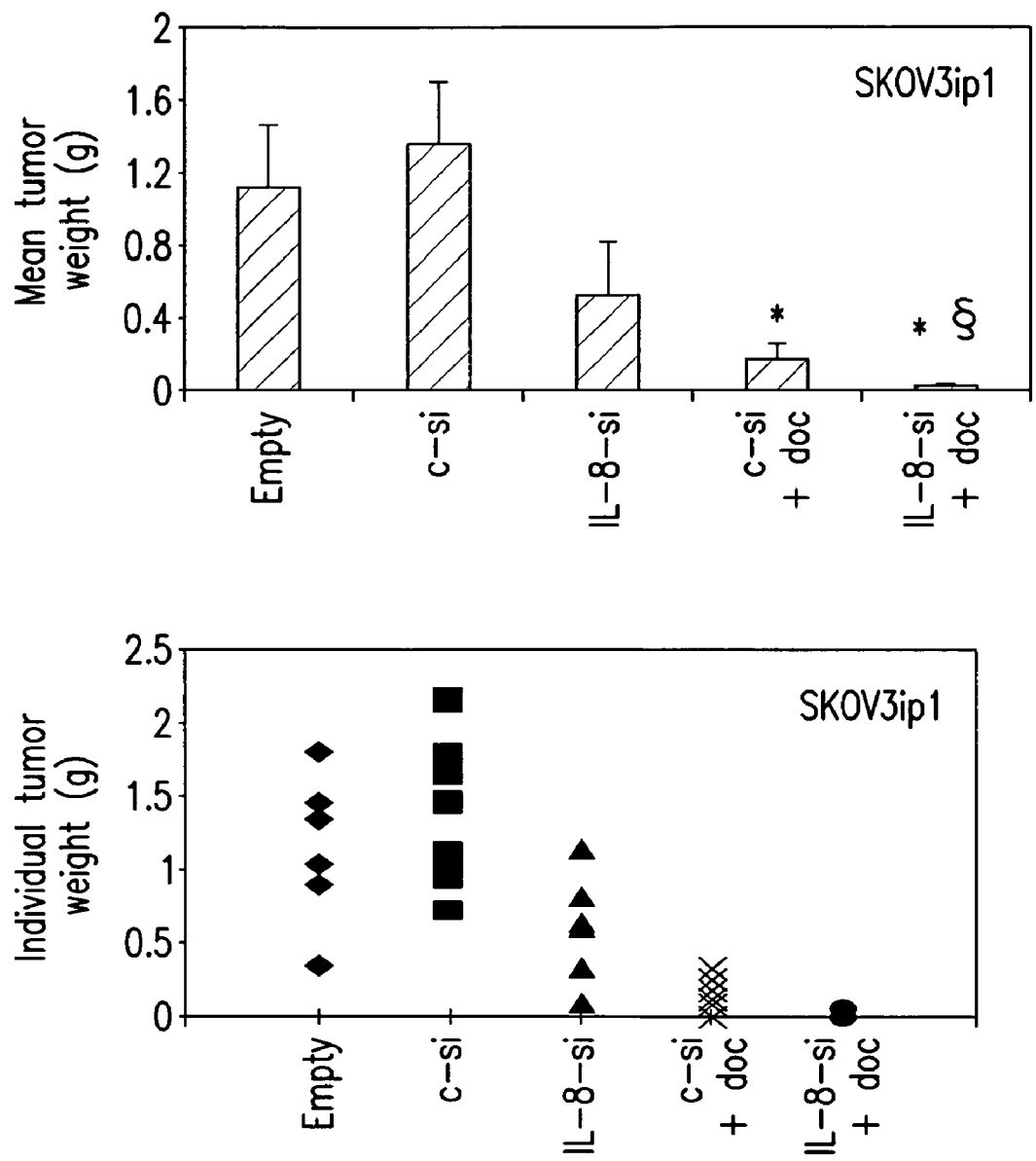
Figure 3C:
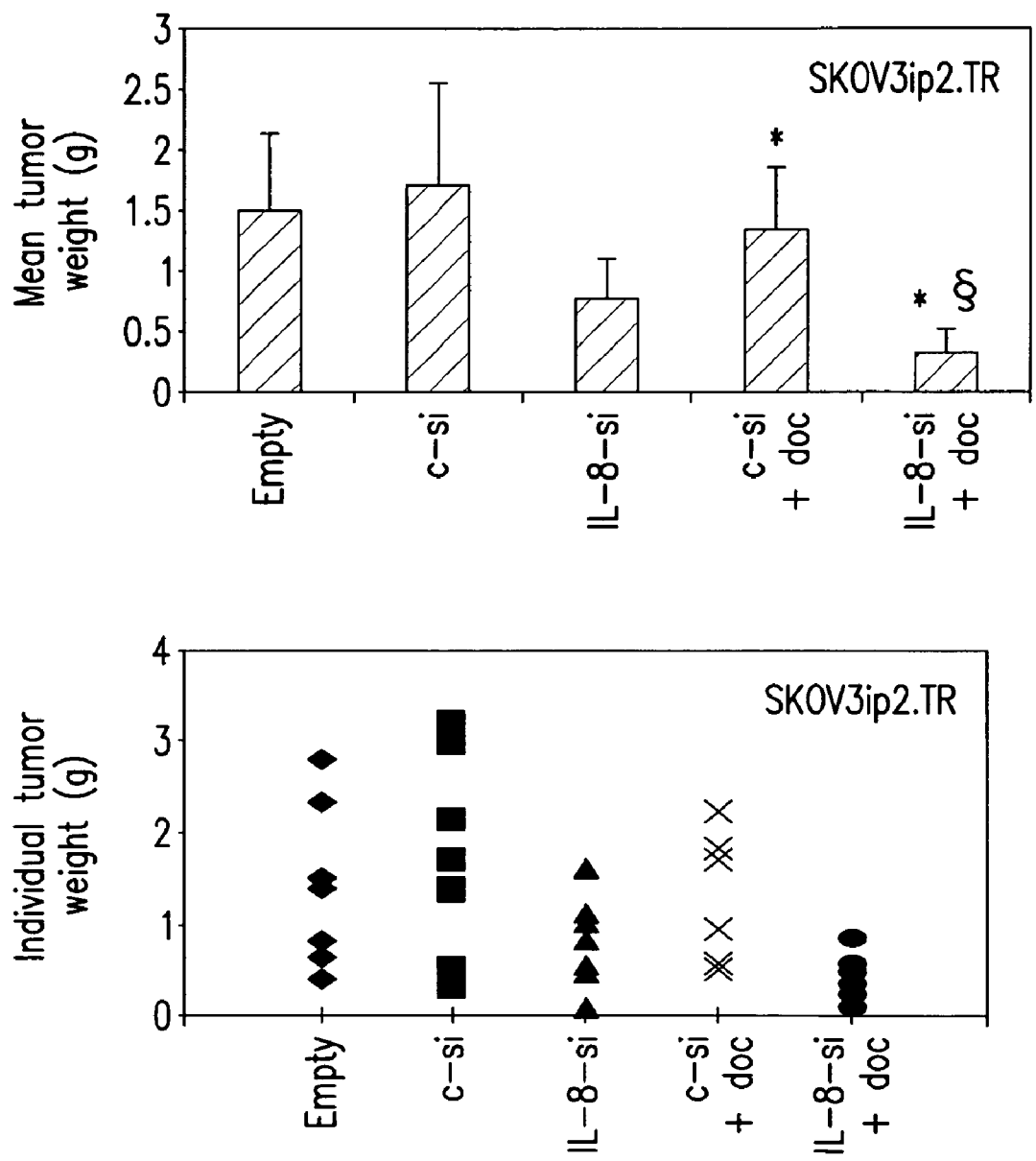
Figure 4A:
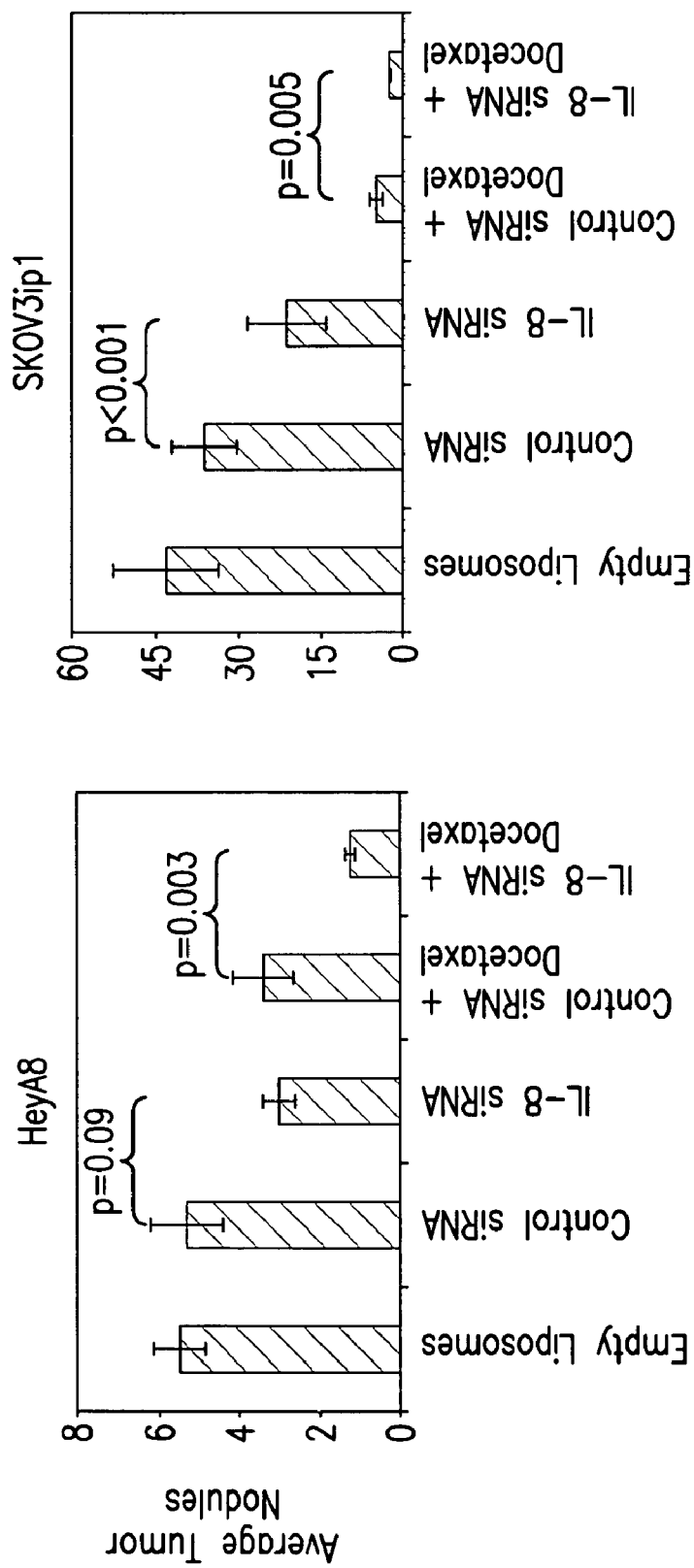
FIG. 4A, 4B. IL-8 downregulation decreased tumor burden in ovarian cancer model.
Figure 4B:
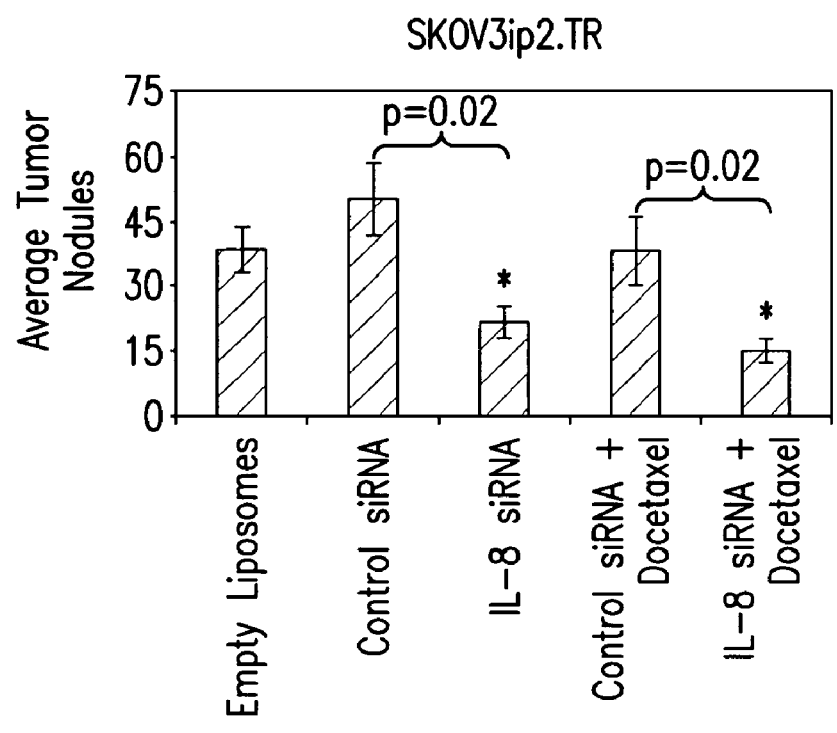
Figure 5:
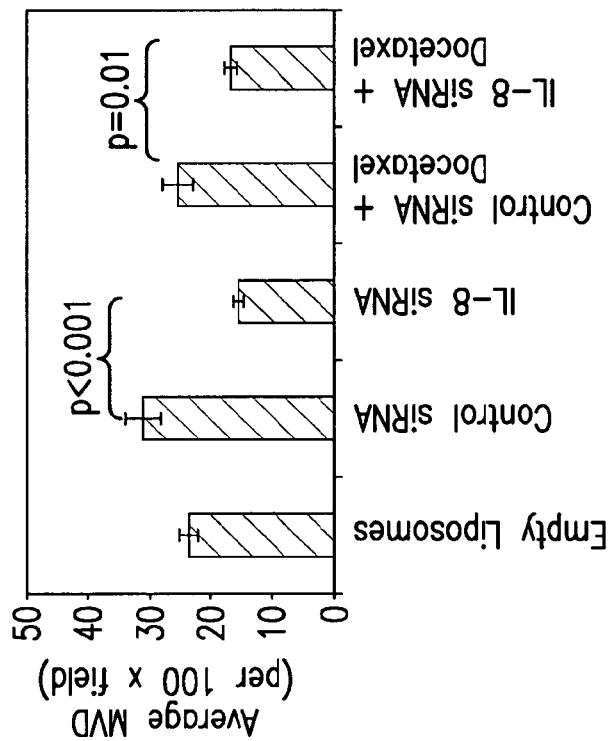
FIG. 5. siRNA-DOPC therapy reduced tumor angiogenesis. IL-8 siRNA-DOPC alone and in combination with docetaxel decreased tumor angiogenesis (represented by average MVD/mouse/treatment group) in HeyA8 model.
Figure 5:
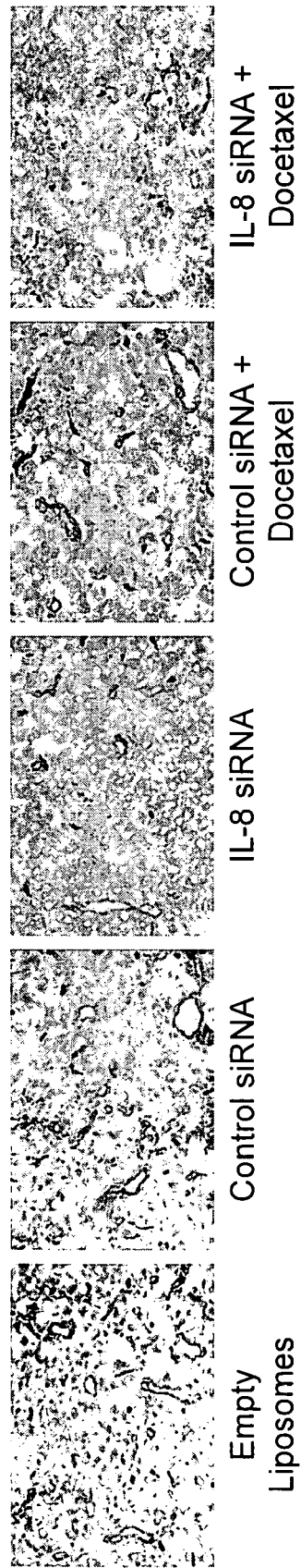
Figure 6:
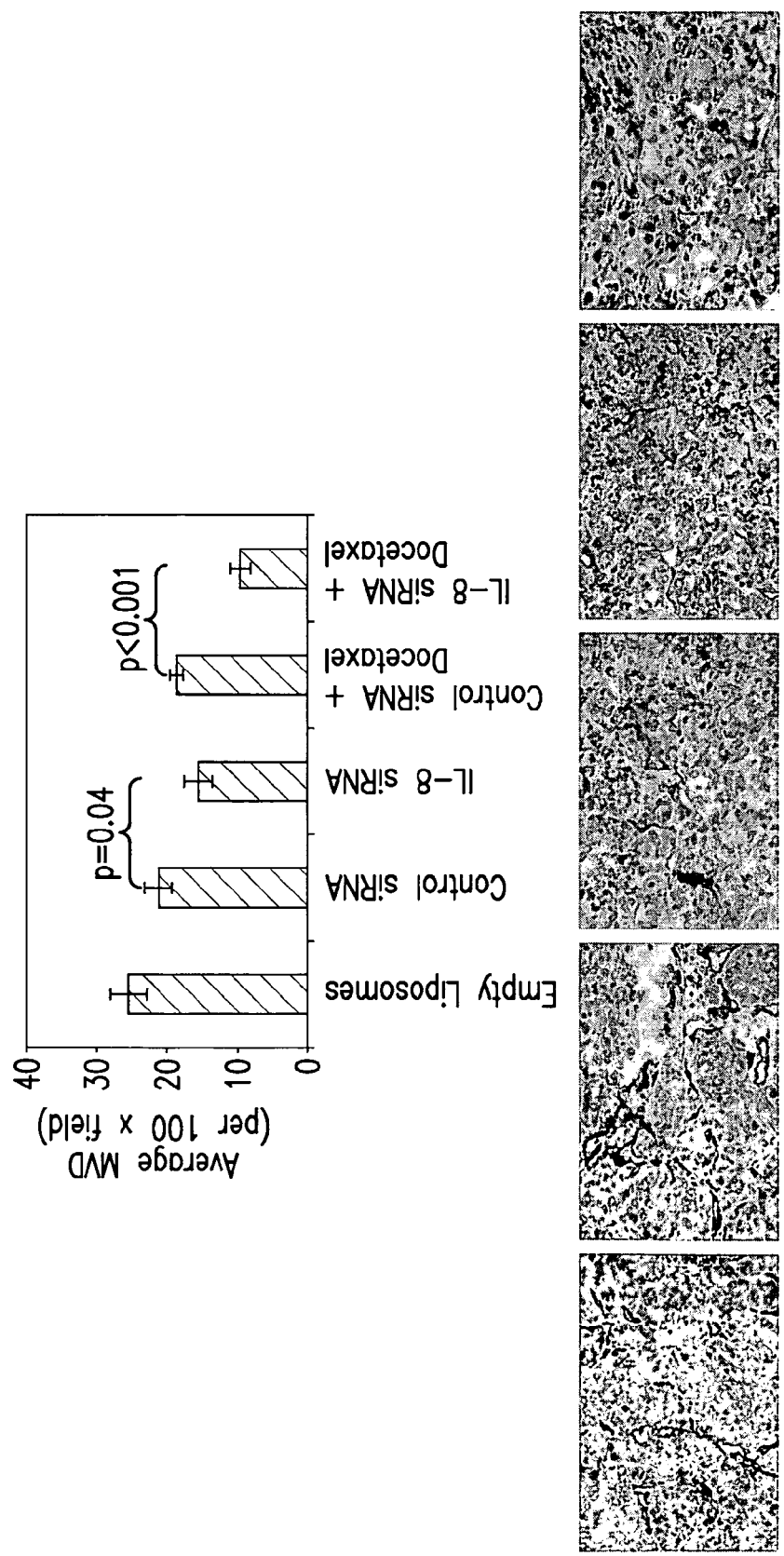
FIG. 6. IL-8 siRNA-DOPC therapy reduced MVD in SKOV31p1 cell line.
Figure 7:
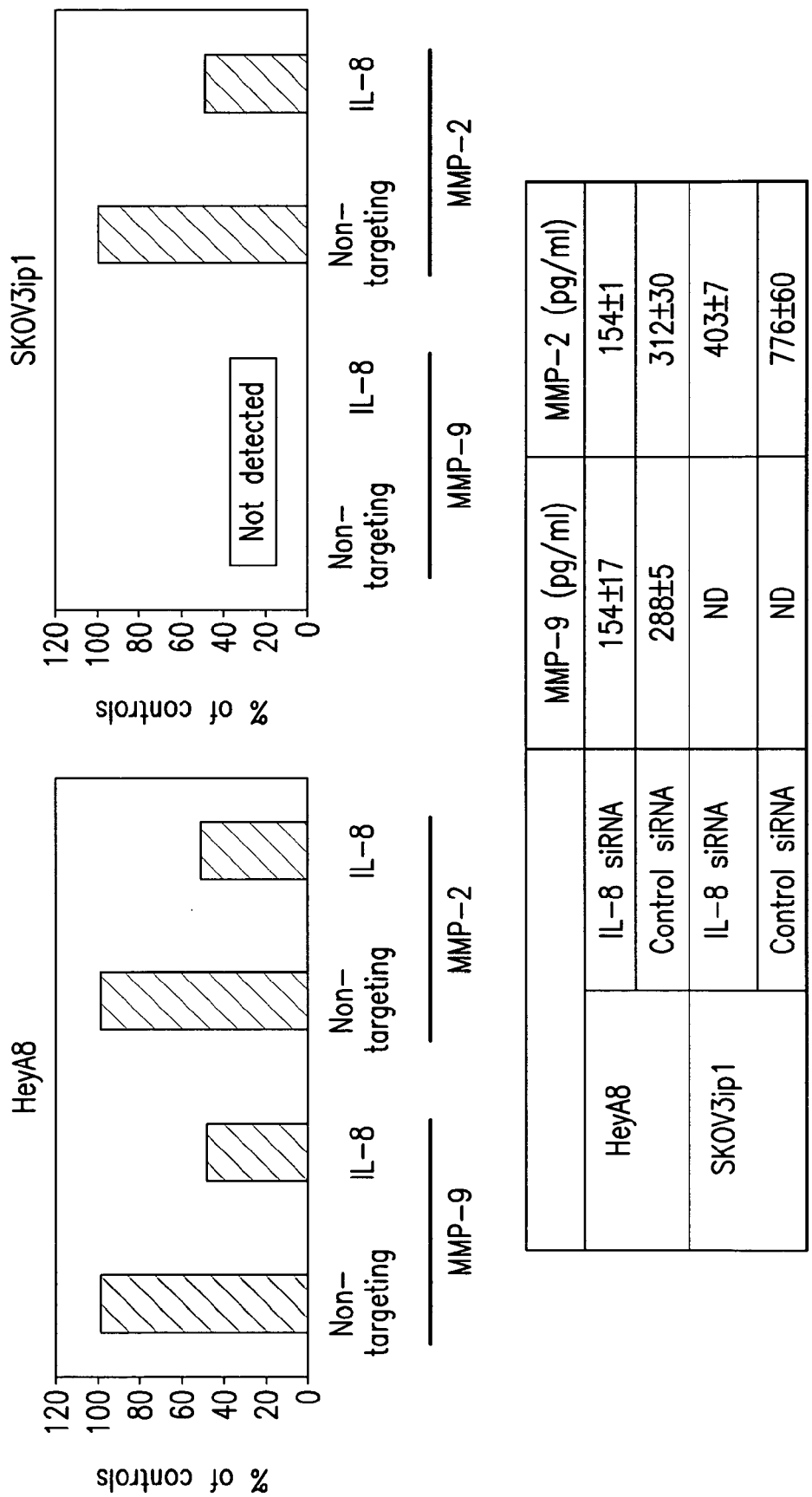
FIG. 7. IL-8 siRNA reduced MMP expression in HeyA8 & SKOV31p1 cell lines. Following IL-8 siRNA transfection in vitro, MMP2 and MMP9 expression were decreased in ovarian cancer cell lines.
Figure 8:
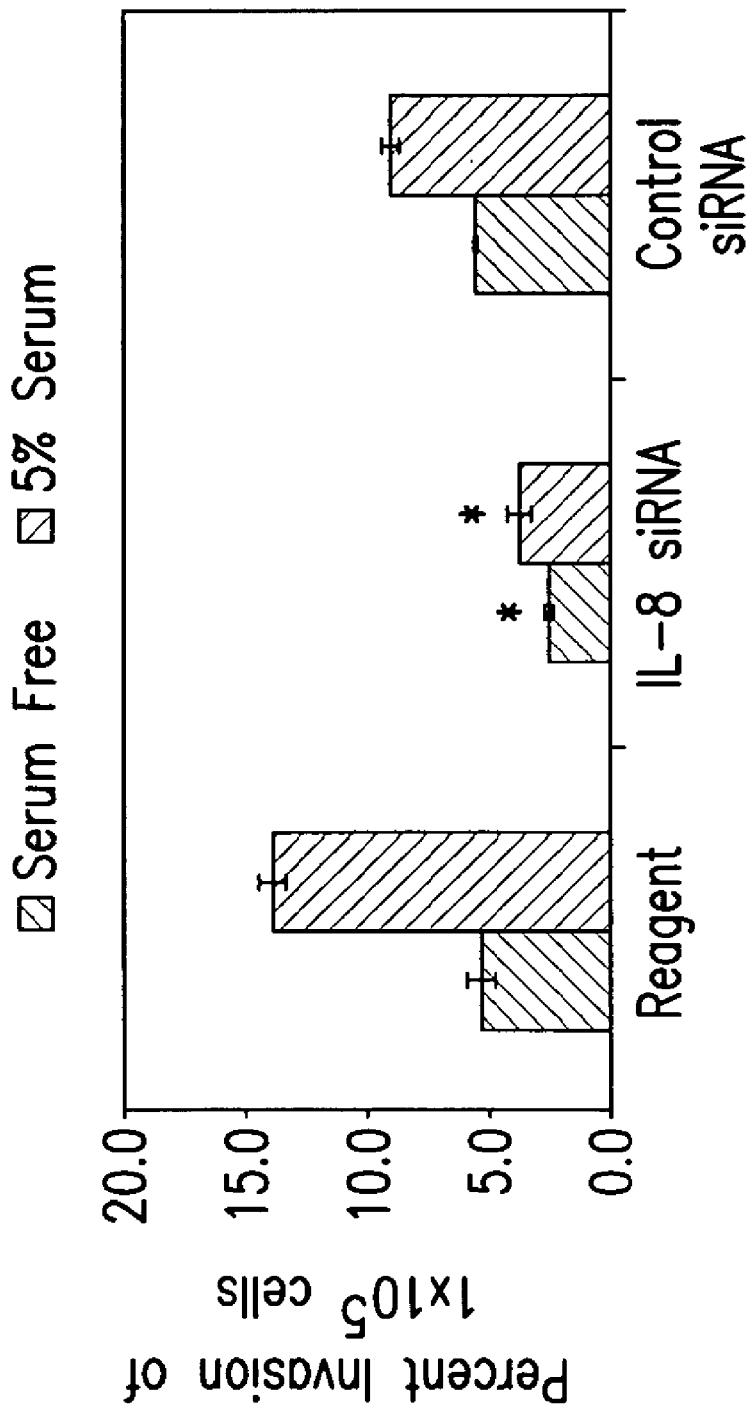
FIG. 8. IL-8 siRNA decreased tumor cell invasion in vitro in HeyA8 cell line.
Figure 9:
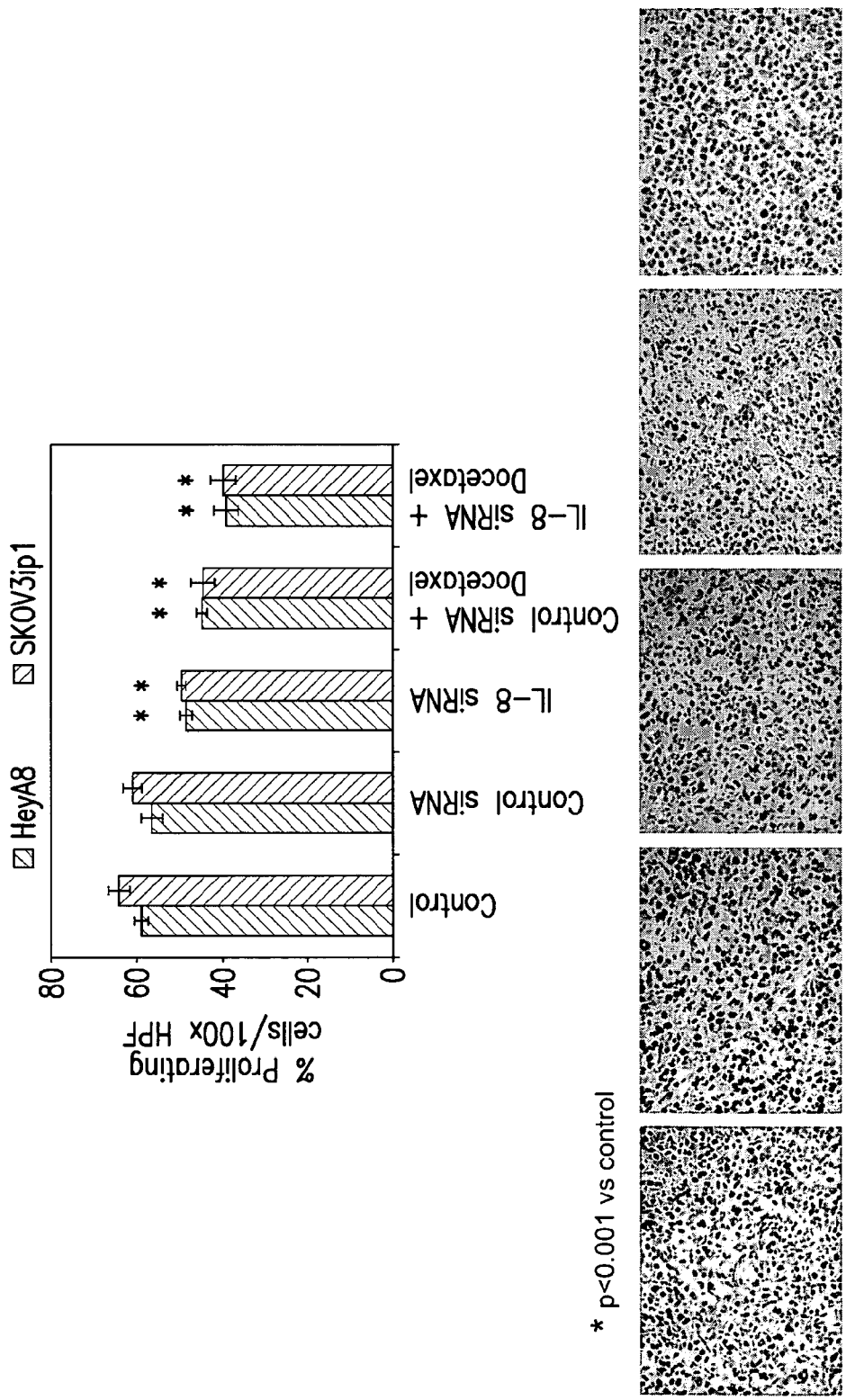
FIG. 9. IL-8 siRNA-DOPC therapy reduced tumor cell proliferation in HeyA8 and SKOV3ip1 cell lines. Compared to controls, IL-8 siRNA-DOPC and docetaxel individual treatments decreased tumor cell proliferation (assessed by PCNA staining of orthotopic tumors). Combination therapy including IL-8 siRNA-DOPC had the greatest reduction in proliferation compared to other groups.

IL-8 siRNA-DOPC effectively reduced ovarian cancer growth in murine ovarian cancer model. The effects of reducing IL-8 expression on ovarian cancer growth were determined using an orthotopic murine ovarian cancer model with HeyA8, SKOV3ip1, and the taxane-resistant SKOV3ip2.TR cell lines. Study design allowed comparison of IL-8 siRNA-DOPC alone and in combination with the chemotherapeutic agent docetaxel. After 3-5 weeks of therapy (dependent on cell line), mice were sacrificed and necropsies were performed. The average tumor weights and tumor weight distribution from each therapy experiment are illustrated in FIG. 3A-C, respectively. Compared to controls (mice treated with empty liposomes), control siRNA-DOPC did not demonstrate significant effects on tumor growth. However, compared to controls, IL-8 siRNA-DOPC demonstrated effective tumor growth inhibition in HeyA8 (32% reduction; p=0.03) and SKOV3ip1 (52%; p=0.07) cell lines. The greatest effect on reducing tumor growth was observed with IL-8 siRNA-DOPC and docetaxel combination treatment in HeyA8 and SKOV3ip1 cell lines (90-98% reduction versus controls; p<0.001 for both groups). Furthermore, compared to all other groups, IL-8 siRNA-DOPC plus docetaxel was significantly more effective in tumor growth inhibition (p<0.01 for both cell lines).

Chemotherapy resistance is a major challenge in treating ovarian cancer patients. The benefit of inhibiting of IL-8 in the setting of chemoresistance in not known. Therefore, we performed a therapy experiment with IL-8 siRNA-DOPC alone and in combination with docetaxel using a taxane-resistant cell line, SKOV3ip2.TR. Compared to controls, single agent IL-8 siRNA-DOPC and docetaxel alone reduced tumor growth by 47% (p=0.12) and 11% (p=0.72), respectively. The greatest effect in tumor growth inhibition was observed with combination therapy (77% reduction; p=0.004).

Data from other measured variables of these therapy experiments are shown in Table 3.

TABLE 3

Characteristics of tumors after IL-8 siRNA-DOPC ± docetaxel

| Cell Line | Group | Tumor incidence (%) | No. nodules (mean ± SE) | P for no. nodules |
|---|---|---|---|---|
| HeyA8 | Empty liposomes | 100 | 5.5 ± 0.6 | |
| | Control siRNA | 70 | 5.3 ± 0.8 | 0.91 |
| | IL-8 siRNA | 100 | 3.4 ± 0.8 | 0.04 |
| | Control siRNA + docetaxel | 100 | 3.0 ± 0.4 | 0.009 |
| | IL-8 siRNA + docetaxel | 90 | 1.2 ± 0.2 | <0.001 |
| SKOV3ip1 | Empty liposomes | 70 | 43.3 ± 9.1 | |
| | Control siRNA | 80 | 36.3 ± 5.5 | 0.45 |
| | IL-8 siRNA | 70 | 21.0 ± 7.3 | 0.07 |
| | Control siRNA + docetaxel | 80 | 5.3 ± 0.7 | 0.004 |
| | IL-8 siRNA + docetaxel | 90 | 2.2 ± 0.3 | <0.001 |
| SKOV3ip2.TR | Empty liposomes | 80 | 38.0 ± 5.5 | |
| | Control siRNA | 70 | 49.7 ± 8.9 | 0.3 |
| | IL-8 siRNA | 90 | 21.9 ± 3.4 | 0.02 |
| | Control siRNA + docetaxel | 70 | 38 ± 7.8 | 0.99 |
| | IL-8 siRNA + docetaxel | 90 | 14.9 ± 3.0 | 0.002 |

The incidence of tumor formation was not significant among all groups in each cell line model. Compared to controls, tumor burden, represented by average number of tumor nodules, was reduced with IL-8 siRNA-DOPC in all three cell lines. Individual docetaxel treatment also reduced tumor burden in HeyA8 and SKOV3ip1 cell lines. However, the greatest reduction was observed with combination IL-8 siRNA-DOPC and docetaxel treatment (p<0.01 for all cell lines). No obvious toxicities were observed in the animals during therapy experiments as determined by behavioral changes, eating and drinking habits, and mobility. Furthermore, mouse weights among treatment groups were not statistically different suggesting eating and drinking habits were not affected by respective treatments.

Effects of IL-8 siRNA-DOPC on tumor angiogenesis (MVD) and proliferation (PCNA). To determine the effects of silencing IL-8 expression with IL-8 siRNA-DOPC alone and in combination with chemotherapy, MVD and tumor cell proliferation indexes were compared among treatment groups. MVD analysis was performed using CD31 staining of orthotopic tumors. Compared to controls, IL-8 siRNA-DOPC therapy significantly reduced MVD by 34% and 39% in HeyA8 and SKOV3ip1 cell lines, respectively (p<0.01 for both cell lines). Minimal effects on MVD were observed in both cell lines with docetaxel alone; however, when compared to combination IL-8 siRNA-DOPC and docetaxel therapy, MVD was significantly decreased (p≦00.01 for HeyA8 and SKOV3ip1).

Next, studies were conducted to determine whether silencing IL-8 expression affected tumor cell proliferation with PCNA staining Both single agent regimens, IL-8 siRNA-DOPC and docetaxel, were effective in reducing proliferation. However, the greatest effect was observed with combination treatment in both cell line models (p<0.001 vs. controls).

The key findings of the present study are that targeted therapy with IL-8 siRNA-DOPC in combination with chemotherapy was effective in reducing tumor growth in both chemotherapy-sensitive and chemotherapy-resistant ovarian cancer models. These effects are likely due to changes in the tumor microenvironment that favor a reduction in angiogenesis and tumor cell proliferation secondary to decreased IL-8 expression. These findings indicate that IL-8 is an attractive therapeutic target in ovarian cancer.

Example 2

Clinical Relevance of IL-8 in Ovarian Carcinoma

Methods

Human ovarian cancer specimens. The use of clinical specimens and clinical data was approved by the Institutional Review Board for the Protection of Human Subjects at U.T.M.D. Anderson Cancer Center (MDACC). For expression analysis, 102 paraffin embedded epithelial ovarian cancer specimens were obtained from MDACC's Department of Gynecologic Oncology Tumor Bank and the University of Iowa Gynecologic Oncology Tumor Bank. Clinical outcome data were obtained by chart review of corresponding ovarian cancer patients. Confirmation of diagnosis was performed by a board certified gynecologic oncologic pathologist. Clinical variables obtained for correlative analysis included: age, stage (staging based on criteria set forth by the International Federation of Gynecology and Obstetrics staging system [FIGO]), tumor grade, presence of ascites, likelihood of surgical cytoreduction (optimal- <1 cm at the completion of primary tumor cytoreduction), and survival outcome at the time of chart review.

Immunohistochemistry. Formalin-fixed paraffin embedded epithelial ovarian cancer specimens were used for IL-8 IHC analysis. The details used for staining IL-8 in human specimens were similar to that described above for orthotopic tumors.

All samples were scored in a blinded fashion by a board-certified pathologist with expertise in gynecologic oncology. IL-8 expression was scored based on proportion of tumor cells with positive staining and staining intensity (Table 4).

An overall score was calculated using the sum of both variables: 0-2 (low) and 3-4 (high).

TABLE 4

Immunohistochemical scoring system for IL-8 expression in human epithelial ovarian cancer specimens. Samples scored in a blinded fashion by gynecologic pathologist based on staining intensity and percentage of positive staining cells, with an overall score assigned to each patient.

| IL-8 intensity | Proportion positive cells | Score |
|---|---|---|
| Low | <5% | 0 |
| Moderate | 6-50% | 1 |
| High | >50% | 2 |

Statistics. The Fisher's exact test was used to determine differences among IL-8 expression and clinical variables. Kaplan-Meier survival curves and log-rank test were used to determine relationship of IL-8 and patient survival. Multivariate analysis was performed using the Cox proportional hazard model. A p-value of less than 0.05 was considered statistically significant.

Results

IL-8 expression in human epithelial ovarian carcinoma. IL-8 expression was measured in 102 human ovarian epithelial cancer specimens using IHC staining. The samples were dichotomized based on an overall score derived from IL-8 staining intensity and percentage of positive staining cells. Overall, 42% of cancer specimens had high IL-8 expression and 58% low expression.

IL-8 expression is associated with clinical outcome. Patient outcome data was obtained from chart review to determine whether IL-8 expression related to clinical outcome (FIG. 10). High IL-8 expression was associated with advanced stage (p=0.019), high-grade histology (p=0.031), and approached significance for likelihood of suboptimal primary surgical cytoreduction (p=0.054).

Figure 11A:
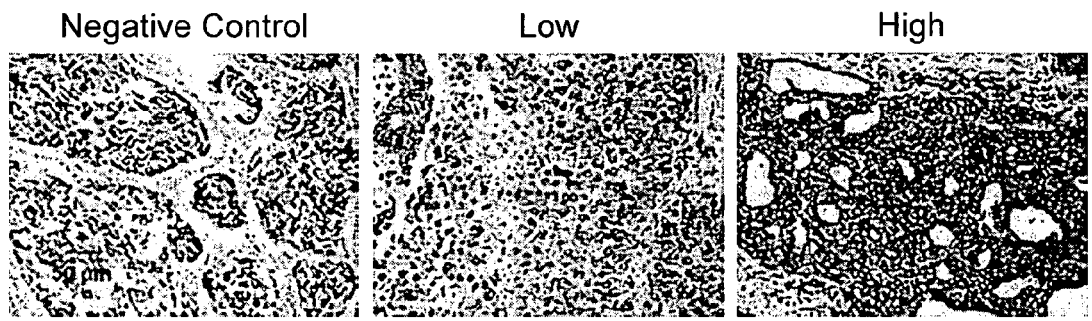
FIG. 11A, 11B. IL-8 expression in human ovarian carcinoma.
Figure 11B:
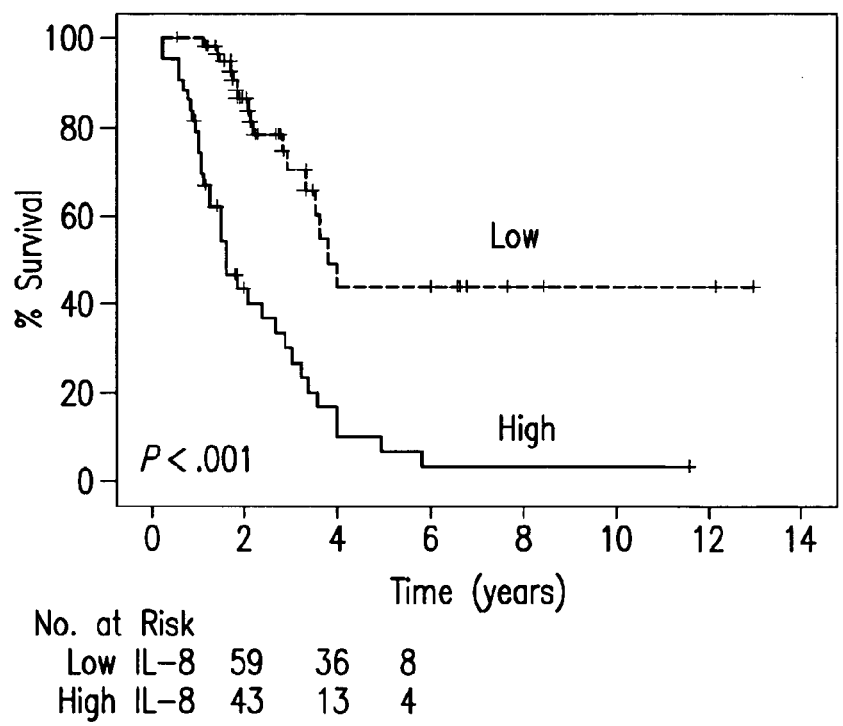

IL-8 expression relates to patient survival in ovarian cancer. Based on the association of high IL-8 expression with some poor prognostic factors, studies were conducted to evaluate whether IL-8 was related to patient survival. Kaplan-Meier analysis demonstrated that high IL-8 expression correlated with decreased median patient survival of 1.62 versus 3.79 years (p<0.001; FIG. 11A, 11B). In addition, multivariate analysis was used to examine whether the significance of IL-8 expression remained after controlling for other factors (FIG. 12). Variables in this analysis included stage, grade, histology, ascites, cytoreduction, and IL-8 expression. As expected, advanced stage disease and the presence of ascites were predictors of poor survival with hazard ratios of 2.35 (p=0.009) and 2.32 (p=0.02), respectively. Furthermore, high IL-8 expression was also a significant prognostic indicator for poor outcome (HR: 3.7 [95% CI: 2-6.8]; p<0.001).

All of the methods disclosed and claimed herein can be made and executed without undue experimentation in light of the present disclosure. While the methods of this invention have been described in terms of preferred embodiments, it will be apparent to those of skill in the art that variations may be applied to the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claim.

REFERENCES

The following references, to the extent that they provide exemplary procedural or other details supplementary to those set forth herein, are specifically incorporated herein by reference.

U.S. Pat. No. 4,659,774
U.S. Pat. No. 4,682,195
U.S. Pat. No. 4,683,202
U.S. Pat. No. 4,816,571
U.S. Pat. No. 4,870,287
U.S. Pat. No. 4,959,463
U.S. Pat. No. 5,030,453
U.S. Pat. No. 5,141,813
U.S. Pat. No. 5,214,136
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,466,786
U.S. Pat. No. 5,470,967
U.S. Pat. No. 5,539,082
U.S. Pat. No. 5,554,744
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,645,897
U.S. Pat. No. 5,652,099
U.S. Pat. No. 5,670,663
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,331
U.S. Pat. No. 5,714,606
U.S. Pat. No. 5,719,262
U.S. Pat. No. 5,736,336
U.S. Pat. No. 5,739,169
U.S. Pat. No. 5,760,395
U.S. Pat. No. 5,763,167
U.S. Pat. No. 5,766,855
U.S. Pat. No. 5,773,571
U.S. Pat. No. 5,777,092
U.S. Pat. No. 5,786,461
U.S. Pat. No. 5,792,847
U.S. Pat. No. 5,801,005
U.S. Pat. No. 5,824,311
U.S. Pat. No. 5,830,880
U.S. Pat. No. 5,846,945
U.S. Pat. No. 5,858,988
U.S. Pat. No. 5,859,221
U.S. Pat. No. 5,872,232
U.S. Pat. No. 5,886,165
U.S. Pat. No. 5,891,625
U.S. Pat. No. 5,908,845
U.S. Pat. No. 5,962,016
U.S. Pat. No. 6,506,559
U.S. Pat. No. 6,573,099
U.S. Pat. No. 6,673,611
U.S. Pat. No. 6,680,068
U.S. Appln. 2002/0168707
U.S. Appln. 2003/0012812

U.S. Appln. 2003/0051263
U.S. Appln. 2003/0055020
U.S. Appln. 2003/0159161
U.S. Appln. 2004/0064842
U.S. Appln. 2004/0204377
U.S. Appln. 2004/0208921
U.S. Appln. 2004/0265839
U.S. Appln. 20040019001
U.S. application Ser. No. 117,363
Austin-Ward and Villaseca, *Revista Medica de Chile*, 126(7): 838-845, 1998.
Bailey and Sullivan, *Biochimica. Biophys. Acts.*, 239-252, 2000.
Bangham et al., *J. Mol. Biol.*, 13(1):253-259, 1965.
Bukowski et al., *Clinical Cancer Res.*, 4(10):2337-2347, 1998.
Christodoulides et al., *Microbiology*, 144(Pt 11):3027-3037, 1998.
Davidson et al., *J. Immunother.*, 21(5):389-398, 1998.
Deamer and Uster, In: Liposome Preparation: Methods and Mechanisms, Ostro (Ed.), Liposomes, 1983.
Dokka et al., Pharm Res, 17: 521-25, 2000.
Donze and Picard, *Nucleic Acids Res,* 30(10):e46, 2002.
Duxbury et al., *Oncogene,* 23:1448-1456, 2004.
Egholm et al., *Nature*, 365(6446):566-568, 1993.
Elbashir et al., *Nature,* 411(6836):494-498, 2001.
Elmen et al., *Nucleic Acids Res.*, 33(1):439-447, 2005.
European Appln. 01219
European Appln. 266,032
Farhood et al., *Biochim. Biophys. Act,* 289-295, 1995.
Fire et al., *Nature,* 391(6669):806-811, 1998.
Froehler et al., *Nucleic Acids Res.,* 14(13):5399-5407, 1986.
Ghosh and Bachhawat, In: Liver Diseases, Targeted Diagnosis and Therapy Using Specific Receptors and Ligands, Wu et al. (Eds.), Marcel Dekker, NY, 87-104, 1991.
Gregoriadis, In: *Drug Carriers in Biology and Medicine*, Gregoriadis (Ed.), 287-341, 1979.
Gutierrez-Puente et al., *J. Pharmacol. Exp. Ther.,* 291:865-869, 1999.
Halder et al., *Clin. Cancer Res.,* 12(16):4916-4924, 2006.
Hanibuchi et al., *Int. J. Cancer,* 78(4):480-485, 1998.
Hannon and Rossi, *Nature,* 431:371-378, 2004.
Hellstrand et al., *Acta Oncologica,* 37(4):347-353, 1998.
Huang et al., *Chem. Res. Toxicol.,* 15:118-126, 2002.
Hui and Hashimoto, *Infection Immun.,* 66(11):5329-5336, 1998.
Ju et al., *Gene Ther.,* 7(19):1672-1679, 2000.
Kaneda et al., *Science,* 243:375-378, 1989.
Karashima et al., *Clin. Cancer Res.,* 9:7:2786-2797, 2003.
Kassim et al., *Clin. Biochem.,* 37:5:363-369, 2004.
Kato et al, *J. Biol. Chem.,* 266:3361-3364, 1991.
Kim et al., *Neoplasia,* 3:1:33-42, 2001.
Koch et al., *Science,* 258(5089):1798-1801, 1992.
Kornberg and Baker, *DNA Replication,* 2nd Ed., Freeman, San Francisco, 1992.
Kostarelos et al., Int J. Cancer, 112: 713-21, 2004.
Krasnici et al., *Int. J. Cancer,* 105(4):561-567, 2003.
Landen et al., *Cancer Res.,* 65:15:6910-6918, 2005.
Landen, Cancer Res, 65: 6910-18, 2005.
Lee et al., *Cancer Res.,* 56:6:1303-1308, 1996.
Leung and Whittaker, *Pharmacol. Ther.,* 107(2):222-239, 2005.
Li et al., *Angiogenesis,* 8:1:63-71, 2005.
Lokshin et al., *Gynecol. Oncol.,* 102(2):244-251, 2006.
Luca et al., *Am. J. Pathol.,* 151:4:1105-1113, 1997.
Matsushima and Oppenheim, *Cytokine,* 1:1:2-13, 1989.
Mian et al., *Clin. Cancer Res.,* 9:8:3167-3175, 2003.
Miller et al., *Biochemistry,* 37(37):12875-83, 1998.
Mitchell et al., *Ann. NY Acad. Sci.,* 690:153-166, 1993.
Mitchell et al., *J. Clin. Oncol.,* 8(5):856-869, 1990.
Morton et al., *Arch. Surg.,* 127:392-399, 1992.
Murdoch et al., *Cytokine,* 11:9:704-712, 1999.
Nicolau et al., *Methods Enzymol.,* 149:157-176, 1987.
PCT Appln. WO 2006/113679
PCT Appln. WO 92/20702
PCT Appln. WO02/100435A1
PCT Appln. WO03/015757A1
PCT Appln. WO04/002453A1
PCT Appln. WO04029213A2
Pietras et al., *Oncogene,* 17(17):2235-2249, 1998.
Qin et al., *Proc. Natl. Acad. Sci. USA,* 95(24):14411-14416, 1998.
Ravindranath and Morton, *Intern. Rev. Immunol.,* 7: 303-329, 1991.
Remington: The Science and Practice of Pharmacy, 21st Ed., 2005.
Roebuck, *J. Interferon Cytokine Res.,* 19:5:429-438, 1999.
Rosenberg et al., *Ann. Surg.* 210(4):474-548, 1989.
Rosenberg et al., *N. Engl. J. Med.,* 319:1676, 1988.
Sambrook et al., *In: Molecular cloning,* Cold Spring Harbor Laboratory Press, Cold Spring Harbor, N.Y., 2001.
Scheit, *In: Synthesis and Biological Function*, Wiley-Interscience, NY, 171-172, 1980.
Schroder and Christophers, *J. Invest. Dermatol.,* 87:1:53-58, 1986.
Sioud and Sorensen, *Biochem. Biophys. Res. Comm.,* 312: 1220-1225, 2003.
Siwak et al., Clin Cancer Res, 8: 955-56, 2002.
Song et al., *Nature Med.* 9:347-351, 2003.
Soutschek et al., *Nature,* 432:173-178, 2004.
Szoka and Papahadjopoulos, *Proc. Natl. Acad. Sci. USA,* 75:4194-4198, 1978.
Thurston et al., *J. Clin. Invest.,* 101(7):1401-1413, 1998.
Trevino et al., *Angiogenesis,* 9:2:101-110, 2006.
Wadhwa et al., *Curr. Opin. Mol. Ther.,* 6(4):367-372, 2004.
Walz et al., *Biochem. Biophys. Res. Commun.,* 149:2:755-761, 1987.
Xie et al., *J. Biol. Chem.,* 276(17):14187-14194, 2001.
Xu and Fidler, *Oncol. Res.,* 12:2:97-106, 2000.
Xu et al., *Cancer Res.,* 59(22):5822-5829, 1999.

The invention claimed is:

1. A method of treating a human subject with cancer comprising administering to the subject a pharmaceutically effective amount of an IL-8 antagonist, wherein the IL-8 antagonist is a siRNA targeted to a gene that encodes an IL-8 polypeptide, further wherein the sense strand of the siRNA is SEQ ID NO:39, 41, 43, or 45.

2. The method of claim 1, wherein the cancer is breast cancer, lung cancer, prostate cancer, ovarian cancer, brain cancer, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia.

3. The method of claim 2, wherein the cancer is ovarian cancer.

4. The method of claim 1, wherein the IL-8 antagonist is comprised in a composition comprising:
 (a) a short inhibitory ribonucleic acid (siRNA) component comprising a siRNA targeted to a gene that encodes an IL-8 polypeptide, further wherein the sense strand of the siRNA is SEQ ID NOs: 39, 41, 43, or 45 or a nucleic acid encoding such siRNA, wherein the siRNA inhibits the expression of a gene that encodes interleukin 8; and
 (b) a lipid component comprising one or more phospholipids, wherein the lipid component has an essentially neutral charge.

5. The method of claim 1, further comprising administering an additional anticancer therapy to the subject.

6. The method of claim 5, wherein the additional anticancer therapy is chemotherapy.

7. The method of claim 6, wherein the chemotherapy comprises administration of docetaxel, paclitaxel, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl- protein tansferase inhibitors, transplatinum, 5-fluorouracil, vincristine, vinblastin, methotrexate, or a combination thereof.

8. The method of claim 1, wherein the IL-8 antagonist is administered to the patient intravenously, intraperitoneally, intratracheally, intratumorally, intramuscularly, endoscopically, intralesionally, percutaneously, subcutaneously, regionally, or by direct injection or perfusion.

9. The method of claim 4, wherein the siRNA component is encapsulated in the lipid component.

10. The method of claim 4, wherein the composition further comprises a pharmaceutically acceptable carrier.

11. The method of claim 4, wherein the lipid component comprises a neutral phospholipid.

12. The method of claim 11, wherein the neutral phospholipid is a phosphatidylcholine or phosphatidylethanolamine.

13. The method of claim 12, wherein the neutral phospholipid is egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, dilinoleoylphosphatidylcholine distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), or lysophosphatidylethanolamine.

14. The method of claim 12, wherein the phosphatidylcholine is DOPC.

15. The method of claim 12, wherein the phosphatidylethanolamine is dioleoylphosphatidylethanolamine ("DOPE").

16. The method of claim 4, wherein the lipid component comprises a positively charged lipid or phospholipid, and a negatively charged lipid or phospholipid.

17. The method of claim 16, wherein the negatively charged phospholipid is a phosphatidylserine or a phosphatidylglycerol.

18. The method of claim 17, wherein the negatively charged phospholipid is dimyristoyl phosphatidylserine ("DMPS"), dipalmitoyl phosphatidylserine ("DPPS"), brain phosphatidylserine ("BPS"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), or dioleoylphosphatidylglycerol ("DOPG").

19. The method of claim 4, wherein the composition further comprises cholesterol or polyethyleneglycol (PEG).

20. The method of claim 4, wherein the siRNA is a double stranded nucleic acid of 21 to 100 nucleobases.

\* \* \* \* \*

SEQUENCE LISTING

<160> NUMBER OF SEQ ID NOS: 46

<210> SEQ ID NO 1
<211> LENGTH: 19
<212> TYPE: RNA
<213> ORGANISM: Artificial

-continued

```
<220> FEATURE:
<223> OTHER INFORMATION: Synthetic primer

<400> SEQUENCE: 1
gccaaggagu gcuaaagaa                                                   19

<210> SEQ ID NO 2
<211> LENGTH: 2943
<212> TYPE: DNA
<213> ORGANISM: Homo sapiens

<400> SEQUENCE: 2
accaggcaac accattgaag gctcatatgt aaaaatccat gccttccttt ctcccaatct       60
ccattcccaa acttagccac tggcttctgg ctgaggcctt acgcataccct cccggggctt     120 gcacacacct tcttctacag aagacacacc ttgggcatat cctacagaag accaggcttc     180
tctctggtcc ttggtagagg gctactttac tgtaacaggg ccagggtgga gagttctctc     240
ctgaagctcc atcccctcta taggaaatgt gttgacaata ttcagaagag taagaggatc     300
aagacttctt tgtgctcaaa taccactgtt ctcttctcta ccctgcccta accaggagct     360 tgtcaccca aactctgagg tgatttatgc cttaatcaag caaacttccc tcttcagaaa      420
agatggctca ttttccctca aaagttgcca ggagctgcca agtattctgc caattcaccc     480
tggagcacaa tcaacaaatt cagccagaac acaactacag ctactattag aactattatt     540
attaataaat tcctctccaa atctagcccc ttgacttcgg atttcacgat ttctcccttc     600
ctcctagaaa cttgataagt ttcccgcgct tccctttttc taagactaca tgtttgtcat     660
cttataaagc aaaggggtga ataaatgaac caaatcaata acttctggaa tatctgcaaa     720
caacaataat atcagctatg ccatctttca ctattttagc cagtatcgag ttgaatgaac     780
atagaaaaat acaaaactga attcttccct gtaaattccc cgttttgacg acgcacttgt     840
agccacgtag ccacgcctac ttaagacaat tacaaaaggc gaagaagact gactcaggct     900
taagctgcca gccagagagg gagtcatttc attggcgttt gagtcagcaa agaagtcaag     960
atggccaaag ttccagacat gtttgaagac ctgaagaact gttacagtga aaatgaagaa    1020
gacagttcct ccattgatca tctgtctctg aatcagaaat ccttctatca tgtaagctat    1080 ggccactcc atgaaggctg catggatcaa tctgtgtctc tgagtatctc tgaaacctct    1140
aaaacatcca agcttacctt caaggagagc atggtggtag tagcaaccaa cgggaaggtt    1200
ctgaagaaga gacggttgag tttaagccaa tccatcactg atgatgacct ggaggccatc    1260
gccaatgact cagaggaaga aatcatcaag cctaggtcag caccttttag cttcctgagc    1320
aatgtgaaat acaactttat gaggatcatc aaatacgaat tcatcctgaa tgacgccctc    1380
aatcaaagta taattcgagc caatgatcag tacctcacgg ctgctgcatt acataatctg    1440
gatgaagcag tgaaatttga catgggtgct tataagtcat caaggatga tgctaaaatt    1500 accgtgattc taagaatctc aaaaactcaa ttgtatgtga ctgcccaaga tgaagaccaa    1560
ccagtgctgc tgaaggagat gcctgagata cccaaaacca tcacaggtag tgagaccaac    1620
ctcctcttct tctgggaaac tcacggcact aagaactatt tcacatcagt tgcccatcca    1680
aacttgttta ttgccacaaa gcaagactac tgggtgtgct tggcagggg gccaccctct    1740 atcactgact ttcagatact ggaaaaccag gcgtaggtct ggagtctcac ttgtctcact    1800
tgtgcagtgt tgacagttca tatgtaccat gtacatgaag aagctaaatc ctttactgtt    1860
agtcatttgc tgagcatgta ctgagccttg taattctaaa tgaatgttta cactctttgt    1920
aagagtggaa ccaacactaa catataatgt tgttatttaa agaacaccct atattttgca    1980
```

```
tagtaccaat cattttaatt attattcttc ataacaattt taggaggacc agagctactg    2040
actatggcta ccaaaaagac tctacccata ttacagatgg gcaaattaag gcataagaaa    2100
actaagaaat atgcacaata gcagttgaaa caagaagcca cagacctagg atttcatgat    2160
ttcatttcaa ctgtttgcct tctacttta agttgctgat gaactcttaa tcaaatagca    2220
taagtttctg ggacctcagt tttatcattt tcaaaatgga gggaataata cctaagcctt    2280
cctgccgcaa cagttttta tgctaatcag ggaggtcatt ttggtaaaat acttcttgaa    2340
gccgagcctc aagatgaagg caaagcacga aatgttattt tttaattatt atttatatat    2400
gtatttataa atatatttaa gataattata atatactata tttatgggaa cccccttcatc   2460 ctctgagtgt gaccaggcat cctccacaat agcagacagt gttttctggg ataagtaagt    2520
ttgatttcat taatacaggg catttggtc caagttgtgc ttatcccata gccaggaaac    2580
tctgcattct agtacttggg agacctgtaa tcatataata aatgtacatt aattaccttg    2640
agccagtaat tggtccgatc tttgactctt ttgccattaa acttacctgg gcattcttgt    2700
ttcaattcca cctgcaatca agtcctacaa gctaaaatta gatgaactca actttgacaa    2760
ccatgagacc actgttatca aactttctt ttctggaatg taatcaatgt ttcttctagg     2820
ttctaaaaat tgtgatcaga ccataatgtt acattattat caacaatagt gattgataga    2880
gtgttatcag tcataactaa ataaagcttg caacaaaatt ctctgacaaa aaaaaaaaa     2940 aaa                                                                  2943

<210> SEQ ID NO 3
<211> LENGTH: 1498
<212> TYPE: DNA
<213> ORGANISM: Homo sapiens

<400> SEQUENCE: 3
accaaacctc ttcgaggcac aaggcacaac aggctgctct gggattctct tcagccaatc      60
ttcattgctc aagtgtctga agcagccatg gcagaagtac ctgagctcgc cagtgaaatg     120
atggcttatt acagtggcaa tgaggatgac ttgttctttg aagctgatgg ccctaaacag     180
atgaagtgct ccttccagga cctggacctc tgccctctgg atggcggcat ccagctacga     240
atctccgacc accactacag caagggcttc aggcaggccg cgtcagttgt tgtggccatg     300
gacaagctga ggaagatgct ggttccctgc ccacagacct tccaggagaa tgacctgagc     360
accttctttc ccttcatctt tgaagaagaa cctatcttct tcgacacatg ggataacgag     420
gcttatgtgc acgatgcacc tgtacgatca ctgaactgca cgctccggga ctcacagcaa     480
aaaagcttgg tgatgtctgg tccatatgaa ctgaaagctc tccacctcca gggacaggat     540
atggagcaac aagtggtgtt ctccatgtcc tttgtacaag gagaagaaag taatgacaaa     600
atacctgtgg ccttgggcct caaggaaaag aatctgtacc tgtcctgcgt gttgaaagat     660
gataagccca ctctacagct ggagagtgta gatcccaaaa attacccaaa gaagaagatg     720
gaaaagcgat tgtcttcaa caagatagaa atcaataaca gctggaattt gagtctgcc     780 cagttcccca actggtacat cagcacctct caagcagaaa acatgccgt cttcctggga    840 gggaccaaag gcggccagga tataactgac ttcaccatgc aatttgtgtc ttcctaaaga    900
gagctgtacc cagagagtcc tgtgctgaat gtggactcaa tccctagggc tggcagaaag    960
ggaacagaaa ggttttgag tacggctata gcctggactt tcctgttgtc tacaccaatg    1020
cccaactgcc tgcctaggg tagtgctaag aggatctcct gtccatcagc caggacagtc    1080
agctctctcc tttcagggcc aatccccagc ccttttgttg agccaggcct ctctcacctc    1140
```

| | |
|---|---|
| tcctactcac ttaaagcccg cctgacagaa accacggcca catttggttc taagaaaccc | 1200 |
| tctgtcattc gctcccacat tctgatgagc aaccgcttcc ctatttattt atttatttgt | 1260 |
| ttgtttgttt tattcattgg tctaatttat tcaaggggg caagaagtag cagtgtctgt | 1320 |
| aaaagagcct agttttaat agctatgaa tcaattcaat ttggactggt gtgctctctt | 1380 |
| taaatcaagt cctttaatta agactgaaaa tatataagct cagattattt aaatgggaat | 1440 |
| atttataaat gagcaaatat catactgttc aatggttctg aaataaactt cactgaag | 1498 |

<210> SEQ ID NO 4
<211> LENGTH: 1666
<212> TYPE: DNA
<213> ORGANISM: Homo sapiens

<400> SEQUENCE: 4

| | |
|---|---|
| ctccataagg cacaaacttt cagagacagc agagcacaca agcttctagg acaagagcca | 60 |
| ggaagaaacc accggaagga accatctcac tgtgtgtaaa catgacttcc aagctggccg | 120 |
| tggctctctt ggcagccttc ctgatttctg cagctctgtg tgaaggtgca gttttgccaa | 180 |
| ggagtgctaa agaacttaga tgtcagtgca taaagacata ctccaaacct ttccacccca | 240 |
| aatttatcaa agaactgaga gtgattgaga gtggaccaca ctgcgccaac acagaaatta | 300 |
| ttgtaaagct ttctgatgga agagagctct gtctggaccc caaggaaaac tgggtgcaga | 360 |
| gggttgtgga agttttttg aagagggctg agaattcata aaaaaattca ttctctgtgg | 420 |
| tatccaagaa tcagtgaaga tgccagtgaa acttcaagca atctacttc aacacttcat | 480 |
| gtattgtgtg ggtctgttgt agggttgcca gatgcaatac aagattcctg gttaaatttg | 540 |
| aatttcagta acaatgaat agtttttcat tgtaccatga aatatccaga acatacttat | 600 |
| atgtaaagta ttatttattt gaatctacaa aaaacaacaa ataattttta aatataagga | 660 |
| ttttcctaga tattgcacgg gagaaatatac aaatagcaaa attgaggcca agggccaaga | 720 |
| gaatatccga actttaattt caggaattga atgggtttgc tagaatgtga tatttgaagc | 780 |
| atcacataaa aatgatggga caataaattt tgccataaag tcaaatttag ctggaaatcc | 840 |
| tggatttttt tctgttaaat ctggcaaccc tagtctgcta gccaggatcc acaagtcctt | 900 |
| gttccactgt gccttggttt ctcctttatt tctaagtgga aaaagtatta gccaccatct | 960 |
| tacctcacag tgatgttgtg aggacatgtg gaagcacttt aagttttttc atcataacat | 1020 |
| aaattatttt caagtgtaac ttattaacct atttattatt tatgtattta tttaagcatc | 1080 |
| aaatatttgt gcaagaattt ggaaaaatag aagatgaatc attgattgaa tagttataaa | 1140 |
| gatgttatag taaatttatt ttattttaga tattaaatga tgttttatta gataaatttc | 1200 |
| aatcagggtt tttagattaa acaaacaaac aattgggtac ccagttaaat tttcatttca | 1260 |
| gataaacaac aaataatttt ttagtataag tacattattg tttatctgaa attttaattg | 1320 |
| aactaacaat cctagtttga tactcccagt cttgtcattg ccagctgtgt tggtagtgct | 1380 |
| gtgttgaatt acggaataat gagttagaac tattaaaaca gccaaaactc cacagtcaat | 1440 |
| attagtaatt tcttgctggt tgaaacttgt ttattatgta caaatagatt cttataatat | 1500 |
| tatttaaatg actgcatttt taaatacaag gctttatatt tttaacttta agatgttttt | 1560 |
| atgtgctctc caaattttt ttactgtttc tgattgtatg gaaatataaa agtaaatatg | 1620 |
| aaacatttaa aatataattt gttgtcaaag taaaaaaaaa aaaaa | 1666 |

<210> SEQ ID NO 5
<211> LENGTH: 924
<212> TYPE: DNA

<213> ORGANISM: Homo sapiens

<400> SEQUENCE: 5

| | | | | | |
|---|---|---|---|---|---|
| cagagcccca | cgaaggacca | gaacaagaca | gagtgcctcc | tgccgatcca | aacatgagcc | 60
| gcctgcccgt | cctgctcctg | ctccaactcc | tggtccgccc | cggactccaa | gctcccatga | 120
| cccagacaac | gcccttgaag | acaagctggg | ttaactgctc | taacatgatc | gatgaaatta | 180
| taacacactt | aaagcagcca | cctttgcctt | tgctggactt | caacaacctc | aatggggaag | 240
| accaagacat | tctgatggaa | ataaccttc | gaaggccaaa | cctggaggca | ttcaacaggg | 300
| ctgtcaagag | tttacagaac | gcatcagcaa | ttgagagcat | tcttaaaaat | ctcctgccat | 360
| gtctgcccct | ggccacggcc | gcacccacgc | gacatccaat | ccatatcaag | gacggtgact | 420
| ggaatgaatt | ccgaggaaaa | ctgacgttct | atctgaaaac | ccttgagaat | gcgcaggctc | 480
| aacagacgac | tttgagcctc | gcgatctttt | gagtccaacg | tccagctcgt | tctctgggcc | 540
| ttctcaccac | agagcctcgg | gacatcaaaa | acagcagaaa | ttctgaaacc | tctgggtcat | 600
| ctctcacaca | ttccaggacc | agaagcattt | caccttttcc | tgcggcatca | gatgaattgt | 660
| taattatcta | atttctgaaa | tgtgcagctc | ccatttggcc | ttgtgcggtt | gtgttctcat | 720
| ttttatccca | ttgagactat | ttatttatgt | atgtatgtat | ttatttattt | attgcctgga | 780
| gtgtgaactg | tatttatttt | agcagaggag | ccatgtcctg | ctgcttctgc | aaaaaactca | 840
| gagtggggtg | gggagcatgt | tcatttgtac | ctcgagtttt | aaactggttc | ctagggatgt | 900
| gtgagaataa | actagactct | gaac | | | 924

<210> SEQ ID NO 6
<211> LENGTH: 528
<212> TYPE: DNA
<213> ORGANISM: Homo sapiens

<400> SEQUENCE: 6

| | | | | | |
|---|---|---|---|---|---|
| tgcatcgtta | gcttctcctg | ataaactaat | tgtctcacat | tgtcactgca | aatcgacacc | 60
| tattaatagg | tctcaccctcc | caactacttc | cccctctgtt | cttcctgcta | gcatgtgccg | 120
| gcaactttgt | ccacggacac | aagtgcgata | tcaccttaca | ggagatcatc | aaaactttga | 180
| acagcctcac | agagcagaag | actctgtgca | ccgagttgac | cgtaacagac | atctttgctg | 240
| cctccaagaa | cacaactgag | aaggaaacct | tctgcagggc | tgcgactgtg | ctccggcagt | 300
| tctacagcca | ccatgagaag | gacactcgct | gcctgggtgc | gactgcacag | cagttccaca | 360
| ggcacaagca | gctgatccga | ttcctgaaac | ggctcgacag | gaacctctgg | ggcctggcgg | 420
| gcttgaattc | ctgtcctgtg | aaggaagcca | ccagagtac | gttggaaaac | ttcttggaaa | 480
| ggctaaagac | gatcatgaga | gagaaatatt | caaagtgttc | gagctgaa | | 528

<210> SEQ ID NO 7
<211> LENGTH: 816
<212> TYPE: DNA
<213> ORGANISM: Homo sapiens

<400> SEQUENCE: 7

| | | | | | |
|---|---|---|---|---|---|
| atgcactttc | tttgccaaag | gcaaacgcag | aacgtttcag | agccatgagg | atgcttctgc | 60
| atttgagttt | gctagctctt | ggagctgcct | acgtgtatgc | catccccaca | gaaattccca | 120
| caagtgcatt | ggtgaaagag | accttggcac | tgctttctac | tcatcgaact | ctgctgatag | 180
| ccaatgagac | tctgaggatt | cctgttcctg | tacataaaaa | tcaccaactg | tgcactgaag | 240
| aaatctttca | ggggataggc | acactggaga | gtcaaactgt | gcaggggggt | actgtggaaa | 300

| | |
|---|---|
| gactattcaa aaacttgtcc ttaataaaga aatacattga cggccaaaaa aaaaagtgtg | 360 |
| gagaagaaag acgagagta aaccaattcc tagactacct gcaagagttt cttggtgtaa | 420 |
| tgaacaccga gtggataata gaaagttgag actaaactgg tttgttgcag ccaaagattt | 480 |
| tggaggagaa ggacatttta ctgcagtgag aatgagggcc aagaaagagt caggccttaa | 540 |
| ttttcagtat aatttaactt cagagggaaa gtaaatattt caggcatact gacactttgc | 600 |
| cagaaagcat aaaattctta aaatatattt cagatatcag aatcattgaa gtattttcct | 660 |
| ccaggcaaaa ttgatatact tttttcttat taacttaac attctgtaaa atgtctgtta | 720 |
| acttaatagt atttatgaaa tggttaagaa tttggtaaat tagtatttat ttaatgttat | 780 |
| gttgtgttct aataaaacaa aaatagacaa ctgttc | 816 |

<210> SEQ ID NO 8
<211> LENGTH: 1125
<212> TYPE: DNA
<213> ORGANISM: Homo sapiens

<400> SEQUENCE: 8

| | |
|---|---|
| ttctgccctc gagcccaccg ggaacgaaag agaagctcta tctcgcctcc aggagcccag | 60 |
| ctatgaactc cttctccaca agcgccttcg gtccagttgc cttctccctg gggctgctcc | 120 |
| tggtgttgcc tgctgccttc cctgcccag taccccagg agaagattcc aaagatgtag | 180 |
| ccgccccaca cagacagcca ctcacctctt cagaacgaat tgacaaacaa attcggtaca | 240 |
| tcctcgacgg catctcagcc ctgagaaagg agacatgtaa caagagtaac atgtgtgaaa | 300 |
| gcagcaaaga ggcactggca gaaaacaacc tgaaccttcc aaagatggct gaaaaagatg | 360 |
| gatgcttcca atctggattc aatgaggaga cttgcctggt gaaaatcatc actggtcttt | 420 |
| tggagtttga ggtatacta gagtacctcc agaacagatt tgagagtagt gaggaacaag | 480 |
| ccagagctgt gcagatgagt acaaaagtcc tgatccagtt cctgcagaaa aaggcaaaga | 540 |
| atctagatgc aataaccacc cctgacccaa ccacaaatgc cagcctgctg acgaagctgc | 600 |
| aggcacagaa ccagtggctg caggacatga caactcatct cattctgcgc agctttaagg | 660 |
| agttcctgca gtccagcctg agggctcttc ggcaaatgta gcatgggcac ctcagattgt | 720 |
| tgttgttaat gggcattcct tcttctggtc agaaacctgt ccactgggca cagaacttat | 780 |
| gttgttctct atggagaact aaaagtgatga gcgttaggac actatttaa ttatttttaa | 840 |
| tttattaata tttaaatatg tgaagctgag ttaatttatg taagtcatat ttatattttt | 900 |
| aagaagtacc acttgaaaca ttttatgtat tagtttgaa ataataatgg aaagtggcta | 960 |
| tgcagtttga atatcctttg tttcagagcc agatcatttc ttggaaagtg taggcttacc | 1020 |
| tcaaataaat ggctaactta tacatatttt taaagaaata tttatattgt atttatataa | 1080 |
| tgtataaatg gtttttatac caataaatgg catttaaaaa aattc | 1125 |

<210> SEQ ID NO 9
<211> LENGTH: 1809
<212> TYPE: DNA
<213> ORGANISM: Homo sapiens

<400> SEQUENCE: 9

| | |
|---|---|
| gtcttcctcc ctccctccct tcctcttact ctcattcatt tcatacacac tggctcacac | 60 |
| atctactctc tctctctatc tctctcagaa tgacaattct aggtacaact tttggcatgg | 120 |
| ttttttcttt acttcaagtc gtttctggag aaagtggcta tgctcaaaat ggagacttgg | 180 |
| aagatgcaga actggatgac tactcattct catgctatag ccagttggaa gtgaatggat | 240 |

-continued

```
cgcagcactc actgacctgt gcttttgagg acccagatgt caacatcacc aatctggaat    300
ttgaaatatg tggggccctc gtggaggtaa agtgcctgaa tttcaggaaa ctacaagaga    360
tatatttcat cgagacaaag aaattcttac tgattggaaa gagcaatata tgtgtgaagg    420
ttggagaaaa gagtctaacc tgcaaaaaaa tagacctaac cactatagtt aaacctgagg    480
ctccttttga cctgagtgtc gtctatcggg aaggagccaa tgactttgtg gtgacattta    540
atacatcaca cttgcaaaag aagtatgtaa agtttttaat gcacgatgta gcttaccgcc    600
aggaaaagga tgaaaacaaa tggacgcatg tgaatttatc cagcacaaag ctgacactcc    660
tgcagagaaa gctccaaccg gcagcaatgt atgagattaa agttcgatcc atccctgatc    720 actatttaa aggcttctgg agtgaatgga gtccaagtta ttacttcaga actccagaga    780
tcaataatag ctcaggggag atggatccta tcttactaac catcagcatt ttgagttttt    840
tctctgtcgc tctgttggtc atcttggcct gtgtgttatg gaaaaaaagg attaagccta    900
tcgtatggcc cagtctcccc gatcataaga agactctgga acatctttgt aagaaaccaa    960
gaaaaatttt aaatgtgagt ttcaatcctg aaagtttcct ggactgccag attcataggg   1020
tggatgacat tcaagctaga gatgaagtgg aaggttttct gcaagatacg tttcctcagc   1080
aactagaaga atctgagaag cagaggcttg gaggggatgt gcagagcccc aactgcccat   1140
ctgaggatgt agtcatcact ccagaaagct ttggaagaga ttcatccctc acatgcctgg   1200
ctgggaatgt cagtgcatgt gacgccccta ttctctcctc ttccaggtcc ctagactgca   1260
gggagagtgg caagaatggg cctcatgtgt accaggacct cctgcttagc cttgggacta   1320
caaacagcac gctgccccct ccattttctc tccaatctgg aatcctgaca ttgaacccag   1380
ttgctcaggg tcagcccatt cttacttccc tgggatcaaa tcaagaagaa gcatatgtca   1440
ccatgtccag cttctaccaa aaccagtgaa gtgtaagaaa cccagactga acttaccgtg   1500
agcgacaaag atgatttaaa agggaagtct agagttccta gtctccctca cagcacagag   1560
aagacaaaat tagcaaaacc ccactacaca gtctgcaaga ttctgaaaca ttgctttgac   1620
cactcttcct gagttcagtg gcactcaaca tgagtcaaga gcatcctgct tctaccatgt   1680
ggatttggtc acaaggttta aggtgaccca atgattcagc tatttaaaaa aaaaagagga   1740
aagaatgaaa gagtaaagga aatgattgag gagtgaggaa ggcaggaaga gagcatgaga   1800
ggaaaaaaa                                                           1809
```

<210> SEQ ID NO 10
<211> LENGTH: 1666
<212> TYPE: DNA
<213> ORGANISM: Homo sapiens

<400> SEQUENCE: 10

```
ctccataagg cacaaacttt cagagacagc agagcacaca agcttctagg acaagagcca     60
ggaagaaacc accggaagga accatctcac tgtgtgtaaa catgacttcc aagctggccg    120
tggctctctt ggcagccttc ctgatttctg cagctctgtg tgaaggtgca gttttgccaa    180
ggagtgctaa agaacttaga tgtcagtgca taaagacata ctccaaacct ttccacccca    240
aatttatcaa agaactgaga gtgattgaga gtggaccaca ctgcgccaac acagaaatta    300
ttgtaaagct ttctgatgga agagagctct gtctggaccc caaggaaaac tgggtgcaga    360
gggttgtgga agttttttg aagagggctg agaattcata aaaaaattca ttctctgtgg    420
tatccaagaa tcagtgaaga tgccagtgaa acttcaagca aatctacttc aacacttcat    480
gtattgtgtg ggtctgttgt agggttgcca gatgcaatac aagattcctg gttaaatttg    540
```

```
aatttcagta acaatgaat agttttcat tgtaccatga aatatccaga acatacttat      600
atgtaaagta ttatttattt gaatctacaa aaaacaacaa ataattttta aatataagga    660
ttttcctaga tattgcacgg gagaatatac aaatagcaaa attgaggcca agggccaaga    720
gaatatccga actttaattt caggaattga atgggtttgc tagaatgtga tatttgaagc    780
atcacataaa aatgatggga caataaattt tgccataaag tcaaatttag ctggaaatcc    840
tggatttttt tctgttaaat ctggcaaccc tagtctgcta gccaggatcc acaagtcctt    900
gttccactgt gccttggttt ctcctttatt tctaagtgga aaaagtatta gccaccatct    960
tacctcacag tgatgttgtg aggacatgtg aagcactttt aagttttttc atcataacat   1020
aaattatttt caagtgtaac ttattaacct atttattatt tatgtattta tttaagcatc   1080
aaatatttgt gcaagaattt ggaaaaatag aagatgaatc attgattgaa tagttataaa   1140
gatgttatag taaatttatt ttattttaga tattaaatga tgttttatta gataaatttc   1200 aatcaggggtt tttagattaa acaaacaaac aattgggtac ccagttaaat tttcatttca   1260
gataaacaac aaataatttt ttagtataag tacattattg tttatctgaa atttaattg     1320 aactaacaat cctagtttga tactcccagt cttgtcattg ccagctgtgt tggtagtgct   1380
gtgttgaatt acggaataat gagttagaac tattaaaaca gccaaaactc cacagtcaat   1440
attagtaatt tcttgctggt tgaaacttgt ttattatgta caaatagatt cttataatat   1500
tatttaaatg actgcatttt taaatacaag gctttatatt tttaacttta agatgttttt   1560
atgtgctctc caaatttttt ttactgtttc tgattgtatg gaaatataaa agtaaatatg   1620
aaacatttaa aatataattt gttgtcaaag taaaaaaaaa aaaaaa                  1666

<210> SEQ ID NO 11
<211> LENGTH: 591
<212> TYPE: DNA
<213> ORGANISM: Homo sapiens

<400> SEQUENCE: 11
ccgctgtcaa gatgcttctg gccatggtcc ttacctctgc cctgctcctg tgctccgtgg    60
caggccaggg gtgtccaacc ttggcgggga tcctggacat caacttcctc atcaacaaga   120
tgcaggaaga tccagcttcc aagtgccact gcagtgctaa tgtgaccagt tgtctctgtt   180
tgggcattcc ctctgacaac tgcaccagac catgcttcag tgagactg tctcagatga     240 ccaataccac catgcaaaca agatacccac tgattttcag tcgggtgaaa aaatcagttg   300
aagtactaaa gaacaacaag tgtccatatt tttcctgtga acagccatgc aaccaaacca   360
cggcaggcaa cgcgctgaca tttctgaaga gtcttctgga aattttccag aaagaaaaga   420
tgagagggat gagaggcaag atatgaagat gaaatattat ttatcctatt tattaaattt   480
aaaaagcttt ctctttaagt tgctacaatt taaaaatcaa gtaagctact ctaaatcagt   540
atcagttgtg attatttgtt taacattgta tgtctttatt ttgaaataaa t            591

<210> SEQ ID NO 12
<211> LENGTH: 1629
<212> TYPE: DNA
<213> ORGANISM: Homo sapiens

<400> SEQUENCE: 12
acacatcagg ggcttgctct tgcaaaacca aaccacaaga cagacttgca aaagaaggca    60
tgcacagctc agcactgctc tgttgcctgg tcctcctgac tggggtgagg gccagcccag   120
gccagggcac ccagtctgag aacagctgca ccccacttcccc aggcaacctg cctaacatgc  180
```

-continued

| | |
|---|---|
| ttcgagatct ccgagatgcc ttcagcagag tgaagacttt ctttcaaatg aaggatcagc | 240 |
| tggacaactt gttgttaaag gagtccttgc tggaggactt aagggttac ctgggttgcc | 300 |
| aagccttgtc tgagatgatc cagttttacc tggaggaggt gatgccccaa gctgagaacc | 360 |
| aagacccaga catcaaggcg catgtgaact ccctggggga gaacctgaag accctcaggc | 420 |
| tgaggctacg cgcgtgtcat cgatttcttc cctgtgaaaa caagagcaag gccgtggagc | 480 |
| aggtgaagaa tgcctttaat aagctccaag agaaaggcat ctacaaagcc atgagtgagt | 540 |
| ttgacatctt catcaactac atagaagcct acatgacaat gaagatacga aactgagaca | 600 |
| tcagggtggc gactctatag actctaggac ataaattaga ggtctccaaa atcggatctg | 660 |
| gggctctggg atagctgacc cagccccttg agaaacctta ttgtacctct cttatagaat | 720 |
| atttattacc tctgatacct caaccccat ttctatttat ttactgagct tctctgtgaa | 780 |
| cgatttagaa agaagcccaa tattataatt tttttcaata tttattattt tcacctgttt | 840 |
| ttaagctgtt tccatagggt gacacactat ggtatttgag tgttttaaga taaattataa | 900 |
| gttacataag ggaggaaaaa aaatgttctt tggggagcca acagaagctt ccattccaag | 960 |
| cctgaccacg ctttctagct gttgagctgt tttccctgac ctccctctaa tttatcttgt | 1020 |
| ctctgggctt ggggcttcct aactgctaca aatactctta ggaagagaaa ccagggagcc | 1080 |
| cctttgatga ttaattcacc ttccagtgtc tcggagggat tcccctaacc tcattcccca | 1140 |
| accacttcat tcttgaaagc tgtggccagc ttgttattta taacaaccta aatttggttc | 1200 |
| taggccgggc gcggtggctc acgcctgtaa tcccagcact ttgggaggct gaggcgggtg | 1260 |
| gatcacttga ggtcaggagt tcctaaccag cctggtcaac atggtgaaac cccgtctcta | 1320 |
| ctaaaaatac aaaaattagc cgggcatggt ggcgcgcacc tgtaatccca gctacttggg | 1380 |
| aggctgaggc aagagaattg cttgaaccca ggagatggaa gttgcagtga gctgatatca | 1440 |
| tgcccctgta ctccagcctg ggtgacagag caagactctg tctcaaaaaa taaaaataaa | 1500 |
| aataaatttg gttctaatag aactcagttt taactagaat ttattcaatt cctctgggaa | 1560 |
| tgttacattg tttgtctgtc ttcatagcag attttaattt tgaataaata aatgtatctt | 1620 |
| attcacatc | 1629 |

<210> SEQ ID NO 13
<211> LENGTH: 2354
<212> TYPE: DNA
<213> ORGANISM: Homo sapiens

<400> SEQUENCE: 13

| | |
|---|---|
| gctcagggca catgcctccc ctccccaggc cgcggcccag ctgaccctcg ggctccccc | 60 |
| ggcagcggac agggaagggt taaaggcccc cggctccctg cccctgccc tgggaaccc | 120 |
| ctggccctgt ggggacatga actgtgtttg ccgcctggtc ctggtcgtgc tgagcctgtg | 180 |
| gccagataca gctgtcgccc ctgggccacc acctggcccc cctcgagttt ccccagaccc | 240 |
| tcgggccgag ctggacagca ccgtgctcct gacccgctct ctcctggcgg acacgcggca | 300 |
| gctggctgca cagctgaggg acaaattccc agctgacggg gaccacaacc tggattccct | 360 |
| gcccaccctg ccatgagtg cggggggcact gggagctcta cagctcccag gtgtgctgac | 420 |
| aaggctgcga gcgacctac tgtcctacct cggcacgtg cagtggctgc ccgggcagg | 480 |
| tggctcttcc ctgaagaccc tggagcccga gctgggcacc ctgcaggccc gactggaccg | 540 |
| gctgctgcgc cggctgcagc tcctgatgtc ccgcctggcc ctgccccagc cacccccgga | 600 |
| cccgccggcg ccccgctgg cgccccccctc ctcagcctgg gggggcatca gggccgccca | 660 |

```
cgccatcctg gggggggctgc acctgacact tgactgggcc gtgagggggac tgctgctgct      720 gaagactcgg ctgtgacccg ggcccaaag ccaccaccgt ccttccaaag ccagatctta        780
tttatttatt tatttcagta ctgggggcga acagccagg tgatccccccc gccattatct       840 ccccctagtt agagacagtc cttccgtgag gcctgggggg catctgtgcc ttatttatac        900
ttatttattt caggagcagg ggtgggaggc aggtggactc ctgggtcccc gaggaggagg       960
ggactggggt cccggattct tgggtctcca agaagtctgt ccacagactt ctgccctggc      1020
tcttccccat ctaggcctgg gcaggaacat atattattta tttaagcaat tacttttcat       1080 gttgggggtgg ggacggaggg gaaagggaag cctgggttttt tgtacaaaaa tgtgagaaac    1140
ctttgtgaga cagagaacag ggaattaaat gtgtcataca tatccacttg agggcgattt      1200
gtctgagagc tggggctgga tgcttgggta actgggggcag ggcaggtgga ggggagacct    1260
ccattcaggt ggaggtcccg agtgggcggg gcagcgactg ggagatgggt cggtcaccca      1320
gacagctctg tggaggcagg gtctgagcct tgcctggggc cccgcactgc atagggcctt    1380
ttgtttgttt tttgagatgg agtctcgctc tgttgcctag gctggagtgc agtgaggcaa      1440
tctgaggtca ctgcaacctc cacctccccgg gttcaagcaa ttctcctgcc tcagcctccc    1500
gattagctgg gatcacaggt gtgcaccacc atgcccagct aattatttat ttcttttgta     1560 ttttttagtag agacagggtt tcaccatgtt ggccaggctg gtttcgaact cctgacctca   1620
ggtgatcctc ctgcctcggc ctcccaaagt gctgggatta caggtgtgag ccaccacacc   1680
tgacccatag gtcttcaata aatatttaat ggaaggttcc acaagtcacc ctgtgatcaa     1740
cagtacccgt atgggacaaa gctgcaaggt caagatggtt cattatggct gtgttcacca     1800
tagcaaactg gaaacaatct agatatccaa cagtgagggt taagcaacat ggtgcatctg    1860
tggatagaac gccacccagc cgcccggagc agggactgtc attcagggag gctaaggaga   1920
gaggcttgct tgggatatag aaagatatcc tgacattggc caggcatggt ggctcacgcc     1980
tgtaatcctg gcactttggg aggacgaagc gagtggatca ctgaagtcca agagttcgag    2040
accggcctgc gagacatggc aaaaccctgt ctcaaaaaag aaagaatgat gtcctgacat    2100
gaaacagcag gctacaaaac cactgcatgc tgtgatccca ttttgtgtt tttcttcta        2160 tatatggatt aaaacaaaaa tcctaaaggg aaatacgcca aaatgttgac aatgactgtc     2220
tccaggtcaa aggagagagg tgggattgtg ggtgactttt aatgtgtatg attgtctgta    2280
ttttacagaa tttctgccat gactgtgtat tttgcatgac acattttaaa aataataaac     2340 actatttta gaat                                                          2354

<210> SEQ ID NO 14
<211> LENGTH: 203
<212> TYPE: DNA
<213> ORGANISM: Homo sapiens

<400> SEQUENCE: 14
ttccctggtt tttctggcat ctcccctcgt ggccatatgg gaactgaaga aagatgttta       60
tgtcgtagaa ttggattggt atccggatgc ccctggagaa atggtggtcc tcacctgtga    120 caccccctgaa gaagatggta tcacctggac cttggaccag agcagtgagg tcttaggctc    180
tggcaaaacc ctgaccatcc aag                                               203

<210> SEQ ID NO 15
<211> LENGTH: 1282
<212> TYPE: DNA
<213> ORGANISM: Homo sapiens
```

<400> SEQUENCE: 15

```
aagccaccca gcctatgcat ccgctcctca atcctctcct gttggcactg ggcctcatgg      60
cgcttttgtt gaccacggtc attgctctca cttgccttgg cggctttgcc tccccaggcc     120
ctgtgcctcc ctctacagcc ctcagggagc tcattgagga gctggtcaac atcacccaga     180
accagaaggc tccgctctgc aatggcagca tggtatggag catcaacctg acagctggca     240
tgtactgtgc agccctggaa tccctgatca acgtgtcagg ctgcagtgcc atcgagaaga     300
cccagaggat gctgagcgga ttctgcccgc acaaggtctc agctgggcag ttttccagct     360
tgcatgtccg agacaccaaa atcgaggtgg cccagtttgt aaaggacctg ctcttacatt     420
taaagaaact ttttcgcgag ggacagttca actgaaactt cgaaagcatc attatttgca     480
gagacaggac ctgactattg aagttgcaga ttcattttc tttctgatgt caaaaatgtc     540
ttgggtaggc gggaaggagg gttagggagg ggtaaaattc cttagcttag acctcagcct     600
gtgctgcccg tcttcagcct agccgacctc agccttcccc ttgcccaggg ctcagcctgg     660
tgggcctcct ctgtccaggg ccctgagctc ggtggaccca gggatgacat gtccctacac     720
ccctcccctg ccctagagca cactgtagca ttacagtggg tgcccccctt gccagacatg     780
tggtgggaca gggacccact tcacacacag gcaactgagg cagacagcag ctcaggcaca     840
cttcttcttg gtcttattta ttattgtgtg ttatttaaat gagtgtgttt gtcaccgttg     900
gggattgggg aagactgtgg ctgctagcac ttggagccaa gggttcagag actcagggcc     960
ccagcactaa agcagtggac accaggagtc cctggtaata agtactgtgt acagaattct    1020
gctacctcac tggggtcctg ggcctcgga gcctcatccg aggcagggtc aggagagggg    1080
cagaacagcc gctcctgtct gccagccagc agccagctct cagccaacga gtaatttatt    1140
gttttcctt gtatttaaat attaaatatg ttagcaaaga gttaatatat agaagggtac    1200
cttgaacact gggggagggg acattgaaca agttgtttca ttgactatca aactgaagcc    1260
agaaataaag ttggtgacag at                                             1282
```

<210> SEQ ID NO 16
<211> LENGTH: 4843
<212> TYPE: DNA
<213> ORGANISM: Homo sapiens

<400> SEQUENCE: 16

```
gaggtgggga agccatcgga cgtcggcggt gaggatcttc tcctgaccca gcatcgctca      60
tcacaatgaa gaaccaagac aaaaagaacg gggctgccaa acaatccaat ccaaaaagca     120
gcccaggaca accggaagca ggacccgagg agcccaggag gcggcccagc caggcggctc     180
ctgcagtaga agcagaaggt cccggcagca gccaggctcc tcggaagccg aggggggctc     240
aagccagaac ggctcagtct ggggcccttc gtgatgtctc tgaggagctg agccgccaac     300
tggaagacat actgagcaca tactgtgtgg acaataacca gggggccccc ggcgaggatg     360
ggcacagggt gagccggct gaacccgaag atgcagagaa gtcccggacc tatgtggcaa     420
ggaatgggga gcctgaacca actccagtag tcaatggaga aaggaaccc tccaaggggg     480
atccaaacac agaagagatc cggcagagtg acgaggtcgg agaccgagac catcgaaggc     540
cacaggagaa gaaaaagcc aagggttttgg ggaaggagat cacgttgctg atgcagacat     600
tgaatactct gagtaccca gaggagaagc tggctgctct gtgcaagaag tatgctgaac     660
tgctggagga gcaccggaat tcacagaagc agatgaagct cctacagaaa agcagagcc     720
agctggtgca agagaaggac cacctgcgcg gtgagcacag caaggccgtc ctggccccgca     780
```

```
gcaagcttga gagcctatgc cgtgagctgc agcggcacaa ccgctccctc aaggaagaag    840
gtgtgcagcg ggcccgggag gaggaggaga agcgcaagga ggtgacctcg cacttccagg    900
tgacactgaa tgacattcag ctgcagatgg aacagcacaa tgagcgcaac tccaagctgc    960
gccaagagaa catggagctg gctgagaggc tcaagaagct gattgagcag tatgagctgc   1020
gcgaggagca tatcgacaaa gtcttcaaac acaaggacct acaacagcag ctggtggatg   1080
ccaagctcca gcaggcccag gagatgctaa aggaggcaga gagcggcac cagcgggaga   1140 aggattttct cctgaaagag gcagtagagt cccagaggat gtgtgagctg atgaagcagc   1200
aagagaccca cctgaagcaa cagcttgccc tatacacaga gaagtttgag gagttccaga   1260
acacactttc caaaagcagc gaggtattca ccacattcaa gcaggagatg gaaaagatga   1320
ctaagaagat caagaagctg gagaaagaaa ccaccatgta ccggtcccgg tgggagagca   1380
gcaacaaggc cctgcttgag atggctgagg agaaaacagt ccgggataaa gaactggagg   1440
gcctgcaggt aaaaatccaa cggctggaga agctgtgccg ggcactgcag acagagcgca   1500
atgacctgaa caagagggta caggacctga gtgctggtgg ccagggctcc ctcactgaca   1560
gtggccctga gaggaggcca gaggggcctg gggctcaagc acccagctcc cccagggtca   1620
cagaagcgcc ttgctaccca ggagcaccga gcacagaagc atcaggccag actgggcctc   1680
aagagcccac ctccgccagg gcctagagag cctggtgttg ggtcatgctg ggaagggagc   1740
ggcagcccag ccaggcctgg cccataaaag gctcccatgc tgagcagccc attgctgaag   1800
ccaggatgtt ctgacctggc tggcatctgg cacttgcaat tttggatttt gtgggtcagt   1860
tttacgtaca tagggcattt tgcaaggcct tgcaaatgca tttatacctg taagtgtaca   1920
gtgggcttgc attggggatg ggggtgtgta cagatgaagt cagtggcttg tctgtgagct   1980
gaagagtctt gagaggggct gtcatctgta gctgccatca cagtgagttg gcagaagtga   2040
cttgagcatt tctctgtctg atttgaggct cagaccctc cctgccttc agagctcaag   2100 acaagtaata cacccaggtc ttgactgcat ttgtcttgtg agcagggctt gcttggtcag   2160
ctcaggccct cctagctgct ctggaggctc ctttgattct ctagacctgg aaaaggtgtc   2220
cctaggcaga gccctggcag ggcgctcaga gctggggatt tcctgcctgg aacaagggac   2280
ctggagaatg tttttgcgtg ggatgatgtg ctggtcagga gcccttggg catcgcttcc   2340 cctgcccttt ggtagtgcca ggaccaggcc aatgatgctt tcagtagcc ttatcattca   2400 caggtgcctc tctagcctgc acaaatgatt gacaagagat cacccaaagg attatttctg   2460
aaggtgtttt tttctttatt tctttttctt ttttttttt tttcttttc tttttttt     2520 gcacatgaca gtgtttgtat tgaggacctt ccaaggaaga gggatgctgt agcagtggtg   2580
cctgggtgcc tggcctccag tgtcccacct ccttcaccac cccacttggc tcctttgcca   2640
tcttgatgct gaggtttcct gtttggtgag atcaggttgt tgtggtaaa agaaaggaaa    2700 gggcttctga tggcttgcc acaagcttac ctgtgggttt cagtcctgag aggccaccac   2760
cagttcccat cagcactgtc tccatgcagc agttgctggg tcccatgtcc agctgcctct   2820
ttggcttcat gggttttct gcttcctgcc cccaccccca catgtgcaat cctcaagatt   2880
tgtcctgatt ctatttcctg gcacctccct gcctgtcctt ggggattcta cttcttcctg   2940
tgtgggagcc catagctgtt gtctaacagg taagaaatga aattgaacta ttgactgggc   3000
cccagaaatc cataaaatgg ctgcagacag ttgtttctgt gtcctgttct acccccactc   3060
cagtacataa ctactatgta ctgtgtagag ccattctata tgctgaatgt tctgctgttg   3120
caaacttgcc agggtattag ccagtgtttg tgccaagcag ttttctggga caacagaatg   3180
```

| | | |
|---|---|---|
| actcagacca agatggatag gatggttagg gctttgcttc ttgctgtttt tctttgaagc | 3240 |
| tagttcattg tcctgcaggt cccttcatct tccatcccta gcccactctt ttagcccctta | 3300 |
| ccttaaatct ctcagataag ttggttcaca aagaatgtta agtactgaat catgtgtgac | 3360 |
| tgagaccaga gatggcaaat gaatggcaca ccatttctcc ttctcctgcc ccagggcagg | 3420 |
| taccactgat ctgcatcaga gttgcctgct attctctggt gtatccttca catctaggtg | 3480 |
| ccctcaagca gctgtgtgag tgttgagatc tctgccatct ctggctgaga tactgctgtc | 3540 |
| ctgtgaagtg tttcccatga ccttttttctt cccctttgaa tccctctgtc tggagtagtc | 3600 |
| cttgcctctt cctgctccag tagggccttt tccctacccc agcccctgtg ccaggctaag | 3660 |
| ctggtacaag agctgccaac ctcacagagt gtttgctagg cgagagaggt gcagggaaga | 3720 |
| ggcagaggta tgcaccttcc cccttgaaga gagggaaag gcctacagtg gcccacataa | 3780 |
| ttgcctgact cacacttcag ctacctctta atgcctgtgg agggactgga gctgctggat | 3840 |
| cccagtgtgg tggtgtagga ggccacagtg agcaggtggc cccagctggg tttcccaggt | 3900 |
| caggaatgtg ggcccaggc aaggtgcagc ctttgctcac agctccatcc atgtctagac | 3960 |
| cttcaggcca gtctgcagat gaggttccct acctttttct tctcttcatt gaccaaatca | 4020 |
| accaatcact acagctgctc tgcttctgct ttccaaagta gcccaggtcc tgggccagat | 4080 |
| gcaggggagg tgcctatcca tgagtgaagg ccagtgtctt cctcacctgg gtgggtccca | 4140 |
| cacttgtgac ctcagtttta ggaccaagat ctgtgttggt ttcttagatt gctagctttt | 4200 |
| cctccagggg accacagcag gtgaagctca agagcgcatg gctctgctaa tagtaaattg | 4260 |
| ttttcagggc cttgtccagc tgagagcttc atgtccacca gattctgaga ggtgtcagca | 4320 |
| gcacttttt ttttatttg ttgtttgttt tccatgaggt tatcggacca tgggctgagc | 4380 |
| tcaggcactt tctgtaggag actgttattt ctgtaaagat ggttatttaa ccctcctcca | 4440 |
| ccccatcacg gtggccctga gggctgaccc ggaggccagt ggagctgcct ggtgtccacg | 4500 |
| ggggagggcc aaggcctgct gagctgattc tccagctgct gccccagcct ttccgccttg | 4560 |
| cacagcacag aggtggtcac cccagggaca gccaggcacc tgctcctctt gcccttcctg | 4620 |
| ggggaaggga gctgccttct gtccctgtaa ctgctttcct tatggcccag cccggccact | 4680 |
| cagacttgtt tgaagctgca ctggcagctt ttttgtctcc tttgggtatt cacaacagcc | 4740 |
| agggacttga ttttgatgta ttttaaacca cattaaataa agagtctgtt gccttaaaaa | 4800 |
| aaaaaaaaa aaaaaaaaa aaaaaaaaa aaaaaaaaa aaa | 4843 |

<210> SEQ ID NO 17
<211> LENGTH: 1969
<212> TYPE: DNA
<213> ORGANISM: Homo sapiens

<400> SEQUENCE: 17

| | | |
|---|---|---|
| gactccgggt ggcaggcgcc cggggggaatc ccagctgact cgctcactgc cttcgaagtc | 60 |
| cggcgccccc cgggagggaa ctgggtggcc gcaccctccc ggctgcggtg gctgtcgccc | 120 |
| cccaccctgc agccaggact cgatggaggt acagagctcg gcttctttgc cttgggaggg | 180 |
| gagtggtggt ggttgaaagg gcgatggaat tttccccgaa agcctacgcc cagggcccct | 240 |
| cccagctcca gcgttaccct ccggtctatc ctactggccg agctgccccg ccttctcatg | 300 |
| gggaaaactt agccgcaact tcaatttttg gttttttcctt taatgacact tctgaggctc | 360 |
| tcctagccat cctcccgctt ccggaggagc gcagatcgca ggtccctttg ccctggcgt | 420 |
| gcgactccct actgcgctgc gctcttacgg cgttccaggc tgctggctag cgcaaggcgg | 480 |

| | |
|---|---|
| gccgggcacc ccgcgctccg ctgggagggt gagggacgcg cgtctggcgg ccccagccaa | 540 |
| gctgcgggtt tctgagaaga cgctgtcccg cagccctgag ggctgagttc tgcacccagt | 600 |
| caagctcagg aaggccaaga aaagaatcca ttccaatata tggccatgtg gctctttgga | 660 |
| gcaatgttcc atcatgttcc atgctgctga cgtcacatgg agcacagaaa tcaatgttag | 720 |
| cagatagcca gcccatacaa gatcgtattg tattgtagga ggcatcgtgg atggatggct | 780 |
| gctgaaaacc ccttgccata gccagctctt cttcaatact taaggattta ccgtggcttt | 840 |
| gagtaatgag aatttcgaaa ccacatttga gaagtatttc catccagtgc tacttgtgtt | 900 |
| tacttctaaa cagtcatttt ctaactgaag ctggcattca tgtcttcatt ttgggctgtt | 960 |
| tcagtgcagg gcttcctaaa acagaagcca actgggtgaa tgtaataagt gatttgaaaa | 1020 |
| aaattgaaga tcttattcaa tctatgcata ttgatgctac tttatatacg aaagtgatg | 1080 |
| ttcaccccag ttgcaaagta acagcaatga agtgctttct cttggagtta caagttattt | 1140 |
| cacttgagtc cggagatgca agtattcatg atacagtaga aaatctgatc atcctagcaa | 1200 |
| acaacagttt gtcttctaat gggaatgtaa cagaatctgg atgcaaagaa tgtgaggaac | 1260 |
| tggaggaaaa aaatattaaa gaattttttgc agagttttgt acatattgtc caaatgttca | 1320 |
| tcaacacttc ttgattgcaa ttgattcttt ttaaagtgtt tctgttatta acaaacatca | 1380 |
| ctctgctgct tagacataac aaaacactcg gcatttcaaa tgtgctgtca aaacaagttt | 1440 |
| ttctgtcaag aagatgatca gaccttggat cagatgaact cttagaaatg aaggcagaaa | 1500 |
| aatgtcattg agtaatatag tgactatgaa cttctctcag acttacttta ctcattttt | 1560 |
| taatttatta ttgaaattgt acatatttgt ggaataatgt aaaatgttga ataaaaatat | 1620 |
| gtacaagtgt tgttttttaa gttgcactga tatttaccct cttattgcaa aatagcatt | 1680 |
| gtttaagggt gatagtcaaa ttatgtattg gtggggctgg gtaccaatgc tgcaggtcaa | 1740 |
| cagctatgct ggtaggctcc tgccagtgtg gaaccactga ctactggctc tcattgactt | 1800 |
| ccttactaag catagcaaac agaggaagaa tttgttatca gtaagaaaaa gaagaactat | 1860 |
| atgtgaatcc tcttctttat actgtaattt agttattgat gtataaagca actgttatga | 1920 |
| aataaagaaa ttgcaataac tggcaaaaaa aaaaaaaaa aaaaaaaa | 1969 |

<210> SEQ ID NO 18
<211> LENGTH: 1496
<212> TYPE: DNA
<213> ORGANISM: Homo sapiens

<400> SEQUENCE: 18

| | |
|---|---|
| gactccgggt ggcaggcgcc cggggaatc ccagctgact cgctcactgc cttcgaagtc | 60 |
| cggcgccccc cgggagggaa ctgggtggcc gcaccctccc ggctgcggtg gctgtcgccc | 120 |
| cccacccctgc agccaggact cgatggagaa tccattccaa tatatggcca tgtggctctt | 180 |
| tggagcaatg ttccatcatg ttccatgctg ctgctgacgt cacatggagc acagaaatca | 240 |
| atgttagcag atagccagcc catacaagat cgtattgtat tgtaggaggc atcgtggatg | 300 |
| gatggctgct ggaaaccct tgccatagcc agctcttctt caatacttaa ggatttaccg | 360 |
| tggctttgag taatgagaat tcgaaaacca catttgagaa gtatttccat ccagtgctac | 420 |
| ttgtgtttac ttctaaacag tcattttcta actgaagctg gcattcatgt cttcattttg | 480 |
| ggctgtttca gtgcagggct tcctaaaaca gaagccaact gggtgaatgt aataagtgat | 540 |
| ttgaaaaaaa ttgaagatct tattcaatct atgcatattg atgctacttt atatacggaa | 600 |
| agtgatgttc accccagttg caaagtaaca gcaatgaagt gctttctctt ggagttacaa | 660 |

-continued

| | |
|---|---|
| gttatttcac ttgagtccgg agatgcaagt attcatgata cagtagaaaa tctgatcatc | 720 |
| ctagcaaaca acagtttgtc ttctaatggg aatgtaacag aatctggatg caaagaatgt | 780 |
| gaggaactgg aggaaaaaaa tattaaagaa ttttttgcaga gttttgtaca tattgtccaa | 840 |
| atgttcatca acacttcttg attgcaattg attcttttta aagtgtttct gttattaaca | 900 |
| aacatcactc tgctgcttag acataacaaa acactcggca tttcaaatgt gctgtcaaaa | 960 |
| caagtttttc tgtcaagaag atgatcagac cttggatcag atgaactctt agaaatgaag | 1020 |
| gcagaaaaat gtcattgagt aatatagtga ctatgaactt ctctcagact tactttactc | 1080 |
| attttttttaa tttattattg aaattgtaca tatttgtgga ataatgtaaa atgttgaata | 1140 |
| aaaatatgta caagtgttgt tttttaagtt gcactgatat tttacctctt attgcaaaat | 1200 |
| agcatttgtt taagggtgat agtcaaatta tgtattggtg gggctgggta ccaatgctgc | 1260 |
| aggtcaacag ctatgctggt aggctcctgc cagtgtggaa ccactgacta ctggctctca | 1320 |
| ttgacttcct tactaagcat agcaaacaga ggaagaattt gttatcagta agaaaaagaa | 1380 |
| gaactatatg tgaatcctct tctttatact gtaatttagt tattgatgta taaagcaact | 1440 |
| gttatgaaat aaagaaattg caataactgg caaaaaaaaa aaaaaaaaaa aaaaaa | 1496 |

<210> SEQ ID NO 19
<211> LENGTH: 1843
<212> TYPE: DNA
<213> ORGANISM: Homo sapiens

<400> SEQUENCE: 19

| | |
|---|---|
| caggaattcg gcgaagtggc ggagctgggg ccccagcggg cgccgggggc cgcgggagcc | 60 |
| agcaggtggc gggggctgcg ctccgcccgg gccagcgcgc accaggcagg tgcccgcgcc | 120 |
| tccgcaccgc ggcgacacct ccgcgggcac tcacccaggc cggccgctca caaccgagcg | 180 |
| cagggccgcg gagggagacc aggaaagccg aaggcggagc agctggaggc gaccagcgcc | 240 |
| gggcgaggtc aagtggatcc gagccgcaga gagggctgga gagagtctgc tctccgatga | 300 |
| ctttgcccac tctcttcgca gtggggacac cggaccgagt gcacactgga ggtcccagag | 360 |
| cacgacgagc gcggaggacc gggaggctcc cgggcttgcg tgggcatcac gtgccctccc | 420 |
| cccatgtccg tggaacacgc agacatctgg gtcaagagct acagcttgta ctccagggag | 480 |
| cggtacattt gtaactctgg tttcaagcgt aaagccggca cgtccagcct gacggagtgc | 540 |
| gtgttgaaca aggccacgaa tgtcgcccac tggacaaccc ccagtctcaa atgcattaga | 600 |
| gaccctgccc tggttcacca aaggccagcg ccacccctcca cagtaacgac ggcagggtg | 660 |
| acccccacagc cagagagcct ctccccttct ggaaaagagc ccgcagcttc atctcccagc | 720 |
| tcaaacaaca cagcggccac aacagcagct attgtcccgg gctcccagct gatgccttca | 780 |
| aaatcaccctt ccacaggaac cacagagata agcagtcatg agtcctccca cggcaccccc | 840 |
| tctcagacaa cagccaagaa ctgggaactc acagcatccg cctcccacca gccgccaggt | 900 |
| gtgtatccac agggccacag cgacaccact gtggctatct ccacgtccac tgtcctgctg | 960 |
| tgtgggctga cgctgtgtc tctcctggca tgctacctca gtcaaggca aactcccccg | 1020 |
| ctggccagcg ttgaaatgga agccatggag gctctgccgg tgacttgggg gaccagcagc | 1080 |
| agagatgaag acttggaaaa ctgctctcac cacctatgaa actcggggaa accagcccag | 1140 |
| ctaagtccgg agtgaaggag cctctctgct ttagctaaag acgactgaga agaggtgcaa | 1200 |
| ggaagcgggc tccaggagca agctcaccag gcctctcaga agtcccagca ggatctcacg | 1260 |
| gactgccggg tcggcgcctc ctgcgcgagg gagcaggttc tccgcattcc catgggcacc | 1320 |

-continued

| | | |
|---|---|---|
| acctgcctgc ctgtcgtgcc ttggacccag ggcccagctt cccaggagag accaaaggct | 1380 |
| tctgagcagg atttttattt cattacagtg tgagctgcct ggaatacatg tggtaatgaa | 1440 |
| ataaaaaccc tgccccgaat cttccgtccc tcatcctaac tttcagttca cagagaaaag | 1500 |
| tgacatacccc aaagctctct gtcaattaca aggcttctcc tggcgtggga gacgtctaca | 1560 |
| gggaagacac cagcgtttgg gcttctaacc accctgtctc cagctgctct gcacacatgg | 1620 |
| acagggacct gggaaaggtg ggagagatgc tgagcccagc gaatcctctc cattgaagga | 1680 |
| ttcaggaaga agaaaactca actcagtgcc attttacgaa tatatgcgtt tatatttata | 1740 |
| cttccttgtc tattatatct atacattata tattatttgt attttgacat tgtaccttgt | 1800 |
| ataaacaaaa taaaacatct attttcaata tttttaaaat gca | 1843 |

<210> SEQ ID NO 20
<211> LENGTH: 6193
<212> TYPE: DNA
<213> ORGANISM: Homo sapiens

<400> SEQUENCE: 20

| | | |
|---|---|---|
| tgcttaaaaa aacacaacag gattttcgaa gaatcctttc ttagaaaaca aacaaaaaaa | 60 |
| ccaaacaaaa acgtactttc tccccactag tttacaccac aggaagcgag agagctgctg | 120 |
| ccactgctgc taccacagga agacacagca gggagaagcc ctagtgcctc tgccggctgc | 180 |
| ccaggacctg gtatcggccc acagaccaag tcctccacag agggcgagcc agggtggaga | 240 |
| agagccagcc cagtgaccca aacatccccg ataaaacacc cactgcttaa gaggcaggct | 300 |
| cggatggact atagctttga taccacagcc gaagaccctt gggttaggat ttctgactgc | 360 |
| atcaaaaact tatttagccc catcatgagt gagaaccatg ccacatgcc tctacagccc | 420 |
| aatgccagcc tgaatgaaga agaagggaca cagggccacc cagatgggac cccaccaaag | 480 |
| ctggacaccg ccaatggcac tcccaaagtt tacaagtcag cagacagcag cactgtgaag | 540 |
| aaaggtcctc ctgtggctcc caagccagcc tggtttcgcc aaagcttgaa aggtttgagg | 600 |
| aatcgtgctt cagacccaag agggctcccc gatcctgcct tgtccaccca gccagcacct | 660 |
| gcttccaggg agcacctagg atcacacatc cgggcctcct cctcctcctc ctccatcagg | 720 |
| cagagaatca gctcctttga aacctttggc tcctctcaac tgcctgacaa aggagcccag | 780 |
| agactgagcc tccagccctc ctctggggag gcagcaaaac ctcttgggaa gcatgaggaa | 840 |
| ggacggtttt ctggactctt ggggcgaggg gctgcaccca ctcttgtgcc ccagcagcct | 900 |
| gagcaagtac tgtcctcggg gtcccctgca gcctccgagg ccagagaccc aggtgtgtct | 960 |
| gagtccccctc ccccagggcg gcagcccaat cagaaaaactc tcccccctgg cccggacccg | 1020 |
| ctcctaaggc tgctgtcaac acaggctgag gaatctcaag gcccagtgct caagatgcct | 1080 |
| agccagcgag cacggagctt ccccctgacc aggtcccagt cctgtgagac gaagctactt | 1140 |
| gacgaaaaga ccagcaaact ctattctatc agcagccaag tgtcatcggc tgtcatgaaa | 1200 |
| tccttgctgt gccttccatc ttctatctcc tgtgcccaga ctccctgcat ccccaaggaa | 1260 |
| ggggcatctc caacatcatc atccaacgaa gactcagctg caaatggttc tgctgaaaca | 1320 |
| tctgccttgg acacggggtt ctcgctcaac cttttcagagc tgagagaata tacagagggt | 1380 |
| ctcacgaag ccaaggaaga cgatgatggg gaccacagtt cccttcagtc tggtcagtcc | 1440 |
| gttatctccc tgctgagctc agaagaatta aaaaaactca tcgaggaggt gaaggttctg | 1500 |
| gatgaagcaa cattaaagca attagacggc atccatgtca ccatcttaca caaggaggaa | 1560 |
| ggtgctggtc ttgggttcag cttggcagga ggagcagatc tagaaaacaa ggtgattacg | 1620 |

```
gttcacagag tgtttccaaa tgggctggcc tcccaggaag ggactattca gaagggcaat     1680
gaggttcttt ccatcaacgg caagtctctc aaggggacca cgcaccatga tgccttggcc     1740
atcctccgcc aagctcgaga gcccaggcaa gctgtgattg tcacaaggaa gctgactcca     1800
gaggccatgc ccgacctcaa ctcctccact gactctgcag cctcagcctc tgcagccagt     1860
gatgtttctg tagaatctac agcagaggcc acagtctgca cggtgacact ggagaagatg     1920
tcggcagggc tgggcttcag cctggaagga gggaagggct ccctacacgg agacaagcct     1980
ctcaccatta acaggatttt caaggagca gcctcagaac aaagtgagac agtccagcct      2040
ggagatgaaa tcttgcagct gggtggcact gccatgcagg gcctcacacg gtttgaagcc     2100
tggaacatca tcaaggcact gcctgatgga cctgtcacga ttgtcatcag gagaaaaagc     2160
ctccagtcca aggaaaccac agctgctgga gactcctagg caggacatgc tgaagccaaa     2220
gccaataaca cacagctaac acacagctcc cataaccgct gattctcagg gtctctgctg     2280
ccgccccacc cagatggggg aaagcacagg tgggcttccc agtggctgct gcccaggccc     2340
agaccttcta ggacgccacc cagcaaaagg ttgttcctaa aataagggca gagtcacacg     2400
ggggcagctg atacaaattg cagactgtgt aaaaagagag cttaatgata atattgtggt     2460
gccacaaata aaatggattt attagaattt catatgacat tcatgcctgg cttcgcaaaa     2520
tgtttcaagt actgtaactg tgtcatgatt cacccccaaa cagtgacatt tatttttctc     2580
atgaatctgc aatgtgggca gagattggaa tgggcagctc atctctgtcc cacttggcat     2640
cagctggcgt catgcaaagt catgcaaagg ctgggaccac gtgagatcat tcactcatac     2700
atctggccgt tgatgttggc tgggaactca cctggggctg ctggcctgaa tgcttatagg     2760
tggcctctcc ttgtgcctg ggcctcctca caacatggtg tctggattcc caggatgagc      2820
atcccaggat cgcaagagcc atgtagaagc tgcatcttgt ttatacccttt gccttggaag    2880 ttgcatggca tcacctccac catactccat cagttagagc tgacacaaac ctgcctgggt     2940
ttaaggggag aggaaatatt gctggggtca tttatgaaaa atacagtttg tcacatgaaa     3000
catttgcaaa attgttttg gttggattgg agaagtaatc ctagggaagg gtggtggagc      3060
cagtaaacag aggagtacag gtgaagcacc aagctcaaag cgtggacagg tgtgccgaca     3120
gaaggaacca gcgtgtatat gagggtatca aataaaattg ctactactta cctaccacat     3180
gccaagcact gtgctcaggg ctaaacgggc attgccttta gtgatcacag cagcttctac     3240
ggtgtatggt tctgtgccaa tgtattgata agagggcaca cactgtgtac agtaaatggc     3300
ttatccagct ggtgagtgat gcggcagatt gagttttctt ctgtgattcg gtggagacta     3360
tcagcccaag atgctttaag tgcacaacat tacagggaat gcctgagtgc ctggccaaag     3420
ggatatttgg tttggccatc tctggatgcc tgattgccaa gctcaggacc aggcaatgtg     3480
actttgcatc agcaacaacc agcatccctt gaccaggcct gggccagagt attggtctcc     3540
tctcagcccc tgatcctgtg aagtaaggat gtggggaag acctggcaag gacacagatg      3600
aaacacaaac aatagtaatt ctcaggccat catcagtgga gccatgttaa tgtaatctga     3660
tggcttctcc agggtccaca ggaagtgaag aatctgtttc ccagcagtgg actcaaaacc     3720
catctgggct cctaaccttc ctgtaaaccc ctttagtggc ttcattagag caggcgttca     3780
gctcactgtt ctattcatct caaggaataa tgggcttaga gcagtttctg tcctgctggt     3840
taacttgttt ggcctattcc attctggatt ttgtcaagca gtagacaagc aattagacaa     3900
gaacttggag gcaccatttg tatccacttt ttagacttaa tagaaacatt gaagatgaac     3960
ataatctacc aacgaaagac gtgattcaat tcaacactcc cttcccatga cccaggctgg     4020
```

```
gcaaggaggc cacgtgatgt ggagggcaca ttccttgcct gcacaaactc accatctgtg   4080
cacgcagtgg ccttccctaa aatcagggaa ttgttttaag tcttatcaag cagccaaggg   4140
atgaaagaga aggtgggttt tcatcaagac tggaaggtgg ggacagggat gagcatggag   4200
ctggccgtgg gcctggggta ccaagagact ccttgagaga ccaggcaaag caagtgattg   4260
ggacagaggt tatctgtccc aggttatctg ggcatagatg caggtgagcc catggccctc   4320
ccagtacctc ctgtctctgg cctgttttag aaggttctct cctccccaag gagacacaac   4380
aactcctagg gccactgaag atataactat tgcccaggtt tctggtctct aggctgggga   4440
agtcctctgg gtaggaatca gcaagaagat cctaaaacaa aagctcatcc atttgcgttc   4500
catgatgctg ggatttacac ttgaggctta gctttgctct gccaacttct tcagagctga   4560
cacaggatga aggcaatgcc atcctcaaac actgcaggca tcacagctaa caattgtgaa   4620
gtcgtcttaa ctcaccataa aaaggaatcc actcccaggc agccctactt ctttgctttg   4680
cccagcattt tactgattca tacattatct cacttgtgcc aacactcaag aagcaggcta   4740
cactgacact ggtattcctg cctccatatt ttctttaaaa gacaaatcaa agcagatata   4800
ttaagtgact gttcaagagc acacttggcc caagtggcag agcttggact ggatgcatgt   4860
tttccagctc ctcatccagg gctctgacca gtttaacctg atgcagtcac gtggaggagc   4920
agtgcaggca cagtatgtcc cataggccca gtgagatgca ttcttggttg gctggccttc   4980
cacttggcta cacagggatg tacaaggcga tcccatcttg ataagaccac cacctcagag   5040
tatggagctc agagagggca ggcatgaagt ttccttggct ggtgcaccta gaattggctg   5100
aactcatgag aagttgatat agaacagtgc ttgccacaga gcggggactc ggtaagcact   5160
taatgaatga atgaattcta agtcaatcca agagtctgat gatttcttga aaagggtgtt   5220
agctaaagga tcttaggcat gactgtagaa tttgtagttg caatagaaca gagaaagagg   5280 aagcttctg tctccttaac actgagctgt catgttttaa agcttgctca catcttggca   5340
catttaagag acagtcaccc caggactcaa aaatagggaa gtaacagtaa cgcagggaa   5400 acgttttctg tttggaggag caaaggctga gaacactgtg aaaacatttt gcgcgcacaa   5460
tagtaacctg ggtaaatgca gcgtgaaggg attttagtca cacgtggtct ttcttacaag   5520
gaaggtggtg ggggtgcaga tgaggttgct agagaatgtt agaggatccc tctctggatt   5580
ggagataggg aaagaaagtt gcacggctgc tgaggcccct tctaggtggc aaggctgtgc   5640
tccctggttc tgatgatgtg cctgggtgga catggcccct gtgagtttgt acagtcttgc   5700
agcaggatct agaggggga tttccagcca gggctgctag acggaggcct actcttccat   5760
ctttcctgat ggcaggatgg cctggccagg gcctggaaga cagagacctc ctgcctccgc   5820
ctcagtaaga cgacaaggaa aggcaaatgc ccaaggggaa gaaaaggaag gctcttctcc   5880
ccagagttcc ccatgcagac atgagtgcgt gctcagttca gaatcacttc tgagaactca   5940
tccctaatgc tgcagatttg ggctggaaca gattcacact gtctggtttc accgaggaca   6000
tgaaactcca ccttgcgggg ataaagagag aaaaacaaat tcatcaaatg gaagacacat   6060
tgaaagtgtt tttccttaat gcttatcctg tttttaaacc attatttcca agttgacacc   6120 tttttttaagg aaaaataaat attttgcggc attaaagcca taaaaaaaaa aaaaaaaaaa   6180
aaaaaaaaaa aaa                                                     6193

<210> SEQ ID NO 21
<211> LENGTH: 1859
<212> TYPE: DNA
<213> ORGANISM: Homo sapiens
```

<400> SEQUENCE: 21

```
gcaggcacaa actcatccat ccccagttga ttggaagaaa caacgatgac tcctgggaag      60
acctcattgg tgtcactgct actgctgctg agcctggagg ccatagtgaa ggcaggaatc     120
acaatcccac gaaatccagg atgcccaaat tctgaggaca agaacttccc ccggactgtg     180
atggtcaacc tgaacatcca taaccggaat accaatacca atcccaaaag gtcctcagat     240
tactacaacc gatccacctc accttggaat ctccaccgca atgaggaccc tgagagatat     300
ccctctgtga tctgggaggc aaagtgccgc cacttgggct gcatcaacgc tgatgggaac     360
gtggactacc acatgaactc tgtccccatc cagcaagaga tcctggtcct gcgcaggag      420
cctccacact gccccaactc cttccggctg gagaagatac tggtgtccgt gggctgcacc     480
tgtgtcaccc cgattgtcca ccatgtggcc taagagctct ggggagccca cactccccaa     540
agcagttaga ctatggagag ccgacccagc ccctcaggaa ccctcatcct tcaaagacag     600
cctcatttcg gactaaactc attagagttc ttaaggcagt ttgtccaatt aaagcttcag     660
aggtaacact tggccaagat atgagatctg aattaccttt ccctctttcc aagaaggaag     720
gtttgactga gtaccaattt gcttcttgtt tactttttta agggctttaa gttatttatg     780
tatttaatat gccctgagat aactttgggg tataagattc cattttaatg aattacctac     840
tttattttgt ttgtcttttt aaagaagata agattctggg cttgggaatt ttattattta     900
aaaggtaaaa cctgtattta tttgagctat ttaaggatct atttatgttt aagtatttag     960
aaaaaggtga aaagcacta ttatcagttc tgcctaggta aatgtaagat agaattaaat     1020
ggcagtgcaa aatttctgag tctttacaac atacggatat agtatttcct cctctttgtt    1080
tttaaaagtt ataacatggc tgaaaagaaa gattaaacct actttcatat gtattaattt    1140
aaattttgca atttgttgag gttttacaag agatacagca agtctaactc tctgttccat    1200
taaacccta taataaaatc cttctgtaat aataaagttt caaaagaaaa tgtttatttg    1260
ttctcattaa atgtattta gcaaactcag ctcttcccta ttgggaagag ttatgcaaat    1320
tctcctataa gcaaaacaaa gcatgtcttt gagtaacaat gacctggaaa tacccaaaat    1380
tccaagttct cgatttcaca tgccttcaag actgaacacc gactaaggtt ttcatactat    1440
tagccaatgc tgtagacaga agcattttga taggaataga gcaaataaga taatggccct    1500
gaggaatggc atgtcattat taaagatcat atggggaaaa tgaaaccctc cccaaaatac    1560
aagaagttct gggaggagac attgtcttca gactacaatg tccagttttc ccctagact     1620
caggcttcct ttggagatta aggccctca gagatcaaca gaccaacatt tttctcttcc    1680
tcaagcaaca ctcctagggc ctggcttctg tctgatcaag gcaccacaca acccagaaag    1740
gagctgatgg ggcagaacga actttaagta tgagaaaagt tcagcccaag taaaataaaa    1800
actcaatcac attcaattcc agagtagttt caagtttcac atcgtaacca ttttcgccc      1859
```

<210> SEQ ID NO 22
<211> LENGTH: 711
<212> TYPE: DNA
<213> ORGANISM: Homo sapiens

<400> SEQUENCE: 22

```
tggggttcca gcgggcagc agctgcaggc tgaccttgca gcttggcgga atggactggc      60
ctcacaacct gctgtttctt cttaccattt ccatcttcct ggggctgggc cagcccagga    120
gccccaaaag caagaggaag gggcaagggc ggcctgggcc cctggcccct ggccctcacc    180
aggtgccact ggacctggtg tcacggatga aaccgtatgc ccgcatggag gagtatgaga    240
```

```
ggaacatcga ggagatggtg gcccagctga ggaacagctc agagctggcc cagagaaagt    300
gtgaggtcaa cttgcagctg tggatgtcca acaagaggag cctgtctccc tggggctaca    360
gcatcaacca cgaccccagc cgtatccccg tggacctgcc ggaggcacgg tgcctgtgtc    420
tgggctgtgt gaacccettc accatgcagg aggaccgcag catggtgagc gtgccggtgt    480
tcagccaggt tcctgtgcgc cgccgcctct gcccgccacc gccccgcaca gggccttgcc    540
gccagcgcgc agtcatggag accatcgctg tgggctgcac ctgcatcttc tgaatcacct    600
ggcccagaag ccaggccagc agcccgagac catcctcctt gcacctttgt gccaagaaag    660
gcctatgaaa agtaaacact gacttttgaa agcaaaaaaa aaaaaaaaa a              711

<210> SEQ ID NO 23
<211> LENGTH: 1145
<212> TYPE: DNA
<213> ORGANISM: Homo sapiens

<400> SEQUENCE: 23
attctctccc cagcttgctg agccctttgc tcccctggcg actgcctgga cagtcagcaa     60
ggaattgtct cccagtgcat tttgccctcc tggctgccaa ctctggctgc taaagcggct    120
gccacctgct gcagtctaca cagcttcggg aagaggaaag gaacctcaga ccttccagat    180
cgcttcctct cgcaacaaac tatttgtcgc aggaataaag atggctgctg aaccagtaga    240
agacaattgc atcaactttg tggcaatgaa atttattgac aatacgcttt actttatagc    300
tgaagatgat gaaaacctgg aatcagatta ctttggcaag cttgaatcta aattatcagt    360
cataagaaat ttgaatgacc aagttctctt cattgaccaa ggaaatcggc tctatttga    420 agatatgact gattctgact gtagagataa tgcaccccgg accatattta ttataagtat    480
gtataaagat agccagccta gaggtatggc tgtaactatc tctgtgaagt gtgagaaaat    540
ttcaactctc tcctgtgaga acaaaattat ttcctttaag gaaatgaatc ctcctgataa    600
catcaaggat acaaaaagtg acatcatatt ctttcagaga agtgtcccag acatgataaa    660
taagatgcaa tttgaatctt catcatacga aggatacttt ctagcttgtg aaaaagagag    720
agaccttttt aaactcattt tgaaaaaaga ggatgaattg ggggatagat ctataatgtt    780
cactgttcaa aacgaagact agctattaaa atttcatgcc gggcgcagtg gctcacgcct    840
gtaatcccag ccctttggga ggctgaggcg ggcagatcac cagaggtcag gtgttcaaga    900
ccagcctgac caacatggtg aaaccctcatc tctactaaaa atacaaaaaa ttagctgagt    960
gtagtgacgc atgccctcaa tcccagctac tcaagaggct gaggcaggag aatcacttgc   1020
actccggagg tagaggttgt ggtgagccga gattgcacca ttgcgctcta gcctgggcaa   1080
caacagcaaa actccatctc aaaaaataaa ataaataaat aaacaaataa aaaattcata   1140
atgtg                                                              1145

<210> SEQ ID NO 24
<211> LENGTH: 1030
<212> TYPE: DNA
<213> ORGANISM: Homo sapiens

<400> SEQUENCE: 24
tgcacacact gacaggagtc caagaatgtg cactgaggga gcgtttccgc acagatctgc     60
gtgttcctta ccactcacac atgtgcacac acatatccat gtgtgtgtgc cagtgctttg    120
gggctctgtt ccacggggca tgaagttaca gtgtgtttcc ctttggctcc tgggtacaat    180
actgatattg tgctcagtag acaaccacgg tctcaggaga tgtctgattt ccacagacat    240
```

```
gcaccatata gaagagagtt tccaagaaat caaaagagcc atccaagcta aggacacctt    300
cccaaatgtc actatcctgt ccacattgga gactctgcag atcattaagc ccttagatgt    360
gtgctgcgtg accaagaacc tcctggcgtt ctacgtggac agggtgttca aggatcatca    420
ggagccaaac cccaaaatct tgagaaaaat cagcagcatt gccaactctt tcctctacat    480
gcagaaaact ctgcggcaat gtcaggaaca gaggcagtgt cactgcaggc aggaagccac    540
caatgccacc agagtcatcc atgacaacta tgatcagctg gaggtccacg ctgctgccat    600
taaatccctg ggagagctcg acgtctttct agcctggatt aataagaatc atgaagtaat    660
gttctcagct tgatgacaag gaacctgtat agtgatccag ggatgaacac cccctgtgcg    720
gtttactgtg ggagacagcc caccttgaag gggaaggaga tggggaaggc cccttgcagc    780
tgaaagtccc actggctggc ctcaggctgt cttattccgc ttgaaaatag ccaaaaagtc    840
tactgtggta tttgtaataa actctatctg ctgaaagggc ctgcaggcca tcctgggagt    900
aaagggctgc cttcccatct aatttattgt aaagtcatat agtccatgtc tgtgatgtga    960
gccaagtgat atcctgtagt acacattgta ctgagtggtt tttctgaata aattccatat   1020
tttacctatg                                                          1030

<210> SEQ ID NO 25
<211> LENGTH: 1252
<212> TYPE: DNA
<213> ORGANISM: Homo sapiens

<400> SEQUENCE: 25
ctttgaattc ctagctcctg tggtctccag atttcaggcc taagatgaaa gcctctagtc     60
ttgccttcag ccttctctct gctgcgtttt atctcctatg gactccttcc actggactga    120
agacactcaa tttgggaagc tgtgtgatcg ccacaaacct tcaggaaata cgaaatggat    180
tttctgagat acggggcagt gtgcaagcca aagatgaaaa cattgacatc agaatcttaa    240
ggaggactga gtctttgcaa gacacaaagc ctgcgaatcg atgctgcctc ctgcgccatt    300
tgctaagact ctatctggac agggtattta aaaactacca gacccctgac cattatactc    360
tccggaagat cagcagcctc gccaattcct ttcttaccat caagaaggac ctccggctct    420
gtcatgccca catgacatgc cattgtgggg aggaagcaat gaagaaatac agccagattc    480
tgagtcactt tgaaaagctg gaacctcagg cagcagttgt gaaggctttg ggggaactag    540
acattcttct gcaatggatg gaggagacag aataggagga agtgatgctg ctgctaagaa    600
atattcgagg tcaagagctc cagtcttcaa tacctgcaga ggaggcatga ccccaaacca    660
ccatctcttt actgtactag tcttgtgctg gtcacagtgt atcttattta tgcattactt    720
gcttccttgc atgattgtct ttatgcatcc ccaatcttaa ttgagaccat acttgtataa    780
gattttgta atatctttct gctattggat atatttatta gttaatatat ttatttattt    840
tttgctattt aatgtatttta ttttttttact tggacatgaa actttaaaaa aattcacaga    900
ttatatttat aacctgacta gagcaggtga tgtatttta tacagtaaaa aaaaaaaacc    960
ttgtaaattc tagaagagtg ctagggggg ttattcattt gtattcaact aaggacatat   1020
ttactcatgc tgatgctctg tgagatattt gaaattgaac caatgactac ttaggatggg   1080
ttgtggaata agtttgatg tggaattgca catctacctt acaattactg accatcccca   1140
gtagactccc cagtcccata attgtgtatc ttccagccag gaatcctaca cggccagcat   1200
gtatttctac aaataaagtt ttctttgcat aacaaaaaaa aaaaaaaaaa aa           1252

<210> SEQ ID NO 26
```

<211> LENGTH: 611
<212> TYPE: DNA
<213> ORGANISM: Homo sapiens

<400> SEQUENCE: 26

```
gtgaaaacga gaccaaggtc tagctctact gttggtactt atgagatcca gtcctggcaa    60
catggagagg attgtcatct gtctgatggt catcttcttg gggacactgg tccacaaatc   120
aagctcccaa ggtcaagatc gccacatgat tagaatgcgt caacttatag atattgttga   180
tcagctgaaa aattatgtga atgacttggt ccctgaattt ctgccagctc cagaagatgt   240
agagacaaac tgtgagtggt cagcttttc  ctgctttcag aaggcccaac taaagtcagc   300
aaatacagga acaatgaaa  ggataatcaa tgtatcaatt aaaaagctga gaggaaacc    360
accttccaca aatgcaggga gaagacagaa acacagacta acatgccctt catgtgattc   420
ttatgagaaa aaaccaccca agaattcct  agaaagattc aaatcacttc tccaaaagat   480
gattcatcag catctgtcct ctagaacaca cggaagtgaa gattcctgag atctaactt    540
gcagttggac actatgttac atactctaat atagtagtga aagtcatttc tttgtattcc   600
aagtggagga g                                                        611
```

<210> SEQ ID NO 27
<211> LENGTH: 1147
<212> TYPE: DNA
<213> ORGANISM: Homo sapiens

<400> SEQUENCE: 27

```
cgaccaggtt ctccttcccc agtcaccagt tgctcgagtt agaattgtct gcaatggccg    60
ccctgcagaa atctgtgagc tctttcctta tggggaccct ggccaccagc tgcctccttc   120
tcttggccct cttggtacag ggaggagcag ctgcgcccat cagctcccac tgcaggcttg   180
acaagtccaa cttccagcag ccctatatca ccaaccgcac cttcatgctg gctaaggagg   240
ctagcttggc tgataacaac acagacgttc gtctcattgg ggagaaactg ttccacggag   300
tcagtatgag tgagcgctgc tatctgatga agcaggtgct gaacttcacc cttgaagaag   360
tgctgttccc tcaatctgat aggttccagc cttatatgca ggaggtggtg cccttcctgg   420
ccaggctcag caacaggcta agcacatgtc atattgaagg tgatgacctg catatccaga   480
ggaatgtgca aaagctgaag gacacagtga aaaagcttgg agagagtgga gagatcaaag   540
caattggaga actggatttg ctgtttatgt ctctgagaaa tgcctgcatt tgaccagagc   600
aaagctgaaa aatgaataac taccccctt  tccctgctag aaataacaat tagatgcccc   660
aaagcgattt ttttaacca  aaaggaagat gggaagccaa actccatcat gatgggtgga   720
ttccaaatga accctgcgt  tagttacaaa ggaaccaat  gccactttg  tttataagac   780
cagaaggtag actttctaag catagatatt tattgataac atttcattgt aactggtgtt   840
ctatacacag aaaacaattt attttttaaa taattgtctt tttccataaa aaagattact   900
ttccattcct ttaggggaaa aaaccctaa  atagcttcat gtttccataa tcagtacttt   960
atatttataa atgtatttat tattattata agactgcatt ttatttatat cattttatta  1020
atatggattt atttatagaa acatcattcg atattgctac ttgagtgtaa ggctaatatt  1080
gatatttatg acaataatta tagagctata acatgtttat ttgacctcaa taaacacttg  1140
gatatcc                                                            1147
```

<210> SEQ ID NO 28
<211> LENGTH: 1049
<212> TYPE: DNA

<213> ORGANISM: Homo sapiens

<400> SEQUENCE: 28

| | |
|---|---|
| aaaacaacag gaagcagctt acaaactcgg tgaacaactg agggaaccaa accagagacg | 60 |
| cgctgaacag agagaatcag gctcaaagca agtggaagtg ggcagagatt ccaccaggac | 120 |
| tggtgcaagg cgcagagcca gccagatttg agaagaaggc aaaaagatgc tggggagcag | 180 |
| agctgtaatg ctgctgttgc tgctgccctg gacagctcag ggcagagctg tgcctggggg | 240 |
| cagcagccct gcctggactc agtgccagca gctttcacag aagctctgca cactggcctg | 300 |
| gagtgcacat ccactagtgg gacacatgga tctaagagaa gagggagatg aagagactac | 360 |
| aaatgatgtt ccccatatcc agtgtggaga tggctgtgac ccccaaggac tcagggacaa | 420 |
| cagtcagttc tgcttgcaaa ggatccacca gggtctgatt ttttatgaga agctgctagg | 480 |
| atcggatatt ttcacagggg agccttctct gctccctgat agccctgtgg ccagcttca | 540 |
| tgcctcccta ctgggcctca gccaactcct gcagcctgag ggtcaccact gggagactca | 600 |
| gcagattcca agcctcagtc ccagccagcc atggcagcgt ctccttctcc gcttcaaaat | 660 |
| ccttcgcagc ctccaggcct tgtggctgt agccgcccgg tctttgccc atggagcagc | 720 |
| aaccctgagt ccctaaaggc agcagctcaa ggatggcact cagatctcca tggcccagca | 780 |
| aggccaagat aaatctacca ccccaggcac ctgtgagcca acaggttaat tagtccatta | 840 |
| attttagtgg gacctgcata tgttgaaaat taccaatact gactgacatg tgatgctgac | 900 |
| ctatgataag gttgagtatt tattagatgg gaagggaaat ttgggggatta tttatcctcc | 960 |
| tggggacagt ttggggagga ttatttattg tatttatatt gaattatgta ctttttttcaa | 1020 |
| taaagtctta tttttgtggc taaaaaaaa | 1049 |

<210> SEQ ID NO 29
<211> LENGTH: 1975
<212> TYPE: DNA
<213> ORGANISM: Homo sapiens

<400> SEQUENCE: 29

| | |
|---|---|
| cttgcctgca aacctttact tctgaaatga cttccacggc tgggacggga accttccacc | 60 |
| cacagctatg cctctgattg gtgaatggtg aaggtgcctg tctaactttt ctgtaaaaag | 120 |
| aaccagctgc ctccaggcag ccagccctca agcatcactt acaggaccag agggacaaga | 180 |
| catgactgtg atgaggagct gctttcgcca atttaacacc aagaagaatt gaggctgctt | 240 |
| gggaggaagg ccaggaggaa cacgagactg agagatgaat tttcaacaga ggctgcaaag | 300 |
| cctgtggact ttagccagac ccttctgccc tcctttgctg gcgacagcct ctcaaatgca | 360 |
| gatggttgtg ctcccttgcc tgggttttac cctgcttctc tggagccagg tatcaggggc | 420 |
| ccagggccaa gaattccact ttgggccctg ccaagtgaag ggggttgttc cccagaaact | 480 |
| gtgggaagcc ttctgggctg tgaaagacac tatgcaagct caggataaca tcacgagtgc | 540 |
| ccggctgctg cagcaggagg ttctgcagaa cgtctcggat gctgagagct gttaccttgt | 600 |
| ccacaccctg ctggagttct acttgaaaac tgttttcaaa aactaccaca atagaacagt | 660 |
| tgaagtcagg actctgaagt cattctctac tctggccaac aactttgttc tcatcgtgtc | 720 |
| acaactgcaa cccagtcaag aaaatgagat gttttccatc agagacagtg cacacaggcg | 780 |
| gtttctgcta ttccggagag cattcaaaca gttggacgta gaagcagctc tgaccaaagc | 840 |
| ccttgggggaa gtggacattc ttctgacctg gatgcagaaa ttctacaagc tctgaatgtc | 900 |
| tagaccagga cctccctccc cctggcactg gtttgttccc tgtgtcattt caaacagtct | 960 |

```
cccttcctat gctgttcact ggacacttca cgcccttggc catgggtccc attcttggcc    1020
caggattatt gtcaaagaag tcattcttta agcagcgcca gtgacagtca gggaaggtgc    1080
ctctggatgc tgtgaagagt ctacagagaa gattcttgta tttattacaa ctctatttaa    1140
ttaatgtcag tatttcaact gaagttctat ttatttgtga gactgtaagt tacatgaagg    1200
cagcagaata ttgtgcccca tgcttcttta cccctcacaa tccttgccac agtgtgggc    1260 agtggatggg tgcttagtaa gtacttaata aactgtggtg ctttttttgg cctgtctttg    1320
gattgttaaa aaacagagag ggatgcttgg atgtaaaact gaacttcaga gcatgaaaat    1380
cacactgtct tctgatatct gcagggacag agcattgggg tggggtaag gtgcatctgt     1440 ttgaaaagta aacgataaaa tgtggattaa agtgcccagc acaaagcaga tcctcaataa    1500
acatttcatt tcccacccac actcgccagc tcaccccatc atccctttcc cttggtgccc    1560 tcctttttt tttatcctag tcattcttcc ctaatcttcc acttgagtgt caagctgacc     1620
ttgctgatgg tgacattgca cctggatgta ctatccaatc tgtgatgaca ttccctgcta    1680
ataaaagaca acataactca agtctggcag actttcttct ctatttctgg atgaatgccc    1740
agtgagactg tgttgtacag ctagaaaagg ccttcttccc aatagcaagg ctgtgcatct    1800
agcctcaagc tctggctgaa ctttgtggtc gacatcaatc taaagataca gtgtctgact    1860
ataaccttgt tccaaaaacc taggcaaaga gtatatgtag gaggtgggat atcacttcca    1920
tgacataagt gctattgcag agccgtggcc acccaggaac tcctgactgc tttcc         1975

<210> SEQ ID NO 30
<211> LENGTH: 1187
<212> TYPE: DNA
<213> ORGANISM: Homo sapiens

<400> SEQUENCE: 30
ctcaagtcac tccctaaaaa gacagtggaa ataaatttga ataaacaaaa caggcttgct      60
gaaaataaaa tcaggactcc taacctgctc cagtcagcct gcttccacga ggcctgtcag    120
tcagtgcccc acttgtgact gagtgtgcag tgcccagcat gtaccaggtg gttgcattct    180
tggcaatggt catgggaacc cacacctaca gccactggcc cagctgctgc cccagcaaag    240
ggcaggacac ctctgaggag ctgctgaggt ggagcactgt gcctgtgcct cccctagagc    300
ctgctaggcc caaccgccac ccagagtcct gtagggccag tgaagatgga ccctcaaca    360 gcagggccat ctcccctgg agatatgagt tggacagaga cttgaaccgg ctcccccagg    420
acctgtacca cgcccgttgc ctgtgccgc actgcgtcag cctacagaca ggctcccaca    480 tggaccccg gggcaactcg gagctgctct accacaacca gactgtcttc taccggcggc    540
catgccatgg cgagaagggc acccacaagg ctactgcct ggagcgcagg ctgtaccgtg    600
tttccttagc ttgtgtgtgt gtgcggcccc gtgtgatggg ctagccggac tgctggagg    660 ctggtcccctt tttgggaaac ctggagccag gtgtacaacc acttgccatg aagggccagg    720
atgcccagat gcttggcccc tgtgaagtgc tgtctggagc agcaggatcc cgggacagga    780 tgggggctt tggggaaagc ctgcacttct gcacattttg aaaagagcag ctgctgctta    840
gggccgccgg aagctggtgt cctgtcattt tctctcagga aaggttttca agttctgcc     900 catttctgga ggccaccact cctgtctctt cctctttttcc catcccctgc taccctggcc    960
cagcacaggc actttctaga tatttccccc ttgctggaga agaaagagcc cctggtttta   1020
tttgtttgtt tactcatcac tcagtgagca tctactttgg gtgcattcta gtgtagttac   1080 tagtctttg acatggatga ttctgaggag gaagctgtta ttgaatgtat agagatttat     1140
```

```
ccaaataaat atctttattt aaaaatgaaa aaaaaaaaaa aaaaaaa            1187

<210> SEQ ID NO 31
<211> LENGTH: 1047
<212> TYPE: DNA
<213> ORGANISM: Homo sapiens

<400> SEQUENCE: 31
ctgtgagtga cacacgctga gtggggtgaa gggaaatgct ggtgaatttc attttgaggt    60
gtgggttgct gttagtcact ctgtctcttg ccattgccaa gcacaagcaa tcttccttca   120
ccaaaagttg ttacccaagg ggaacattgt cccaagctgt tgacgctctc tatatcaaag   180
cagcatggct caaagcaacg attccagaag accgcataaa aaatatacga ttattaaaaa   240
agaaaacaaa aaagcagttt atgaaaaact gtcaatttca agaacagctt ctgtccttct   300
tcatggaaga cgtttttggt caactgcaat tgcaaggctg caagaaaata cgctttgtgg   360
aggactttca tagccttagg cagaaattga gccactgtat ttcctgtgct tcatcagcta   420
gagagatgaa atccattacc aggatgaaaa gaatatttta taggattgga aacaaaggaa   480
tctacaaagc catcagtgaa ctggatattc ttctttcctg gattaaaaaa ttattggaaa   540
gcagtcagta aaccaaagcc aagtacattg attttacagt tattttgaaa tacaataaga   600
actgctagaa atatgtttat aacagtctat ttcttttaaa aacttttttaa cataatactg   660 acggcatgtt aggtgattca gaatagacaa gaaggattta gtaaattaac gttttggata   720
taagttgtca ctaatttgca cattttctgt gttttcaaat aatgtttcca ttctgaacat   780
gttttgtcat tcacaagtac attgtgtcaa cttaatttaa agtatgtaac ctgaattaac   840
tcgtgtaata tttgtgtgtg gagtgggatg tgggggtgg aggggaatg acagatttct   900 ggaatgcaat gtaatgttac tgagacttaa atagatgtta tgtatatgat tgtctgttta   960
agtgtttgaa aattgttaat tatgcccagt gtgaacttag tacttaacac attttgattt  1020
taattaaata aattgggttt ccttctc                                      1047

<210> SEQ ID NO 32
<211> LENGTH: 1044
<212> TYPE: DNA
<213> ORGANISM: Homo sapiens

<400> SEQUENCE: 32
gaccaaagag gctgggcccc gccatgggcc agacggcagg cgaccttggc tggcggctca    60
gcctgttgct gcttcccttg ctcctggttc aagctggtgt ctggggattc caaggcccc   120 cagggaggcc ccagctgagc ctgcaggagc tgcggaggga gttcacagtc agcctgcatc   180
tcgccaggaa gctgctctcc gaggttcggg gccaggccca ccgctttgcg gaatctcacc   240
tgccaggagt gaacctgtac ctcctgcccc tgggagagca gctccctgat gtttccctga   300
ccttccaggc ctggcgccgc ctctctgacc cggagcgtct ctgcttcatc tccaccacgc   360 ttcagcccctt ccatgccctg ctgggagggc tggggaccca gggccgctgg accaacatgg   420
agaggatgca gctgtgggcc atgaggctgg acctccgcga tctgcagcgg cacctccgct   480
tccaggtgct ggctgcagga ttcaacctcc cggaggagga ggaggaggaa gaggaggagg   540
aggaggagga gaggaagggg ctgctcccag gggcactggg cagcgcctta cagggcccgg   600
cccaggtgtc ctggccccag ctcctctcca cctaccgcct gctgcactcc ttggagctcg   660
tcttatctcg ggccgtgcgg gagttgctgc tgctgtccaa ggctgggcac tcagtctggc   720
ccttggggtt cccaacattg agccccccagc cctgatcggt ggcttcttag cccctgccc   780
```

| | |
|---|---|
| cccacccttt agaactttag gactggagtc ttggcatcag ggcagccttc gcatcatcag | 840 |
| ccttggacaa gggagggctc ttccagcccc ctgcccagg ctctacccag taactgaaag | 900 |
| cccctctggt cctcgccagc tatttatttc ttggatattt atttattgtt tagggagatg | 960 |
| atggtttatt tattgtcttg gggcccgatg gtcctcctcg ggccaagccc ccatgctggg | 1020 |
| tgcccaataa agcactctca tcca | 1044 |

<210> SEQ ID NO 33
<211> LENGTH: 734
<212> TYPE: DNA
<213> ORGANISM: Homo sapiens

<400> SEQUENCE: 33

| | |
|---|---|
| tgggtgacag cctcagagtg tttcttctgc tgacaaagac cagagatcag gaatgaaact | 60 |
| agacatgact ggggactgca cgccagtgct ggtgctgatg gccgcagtgc tgaccgtgac | 120 |
| tggagcagtt cctgtcgcca ggctccacgg ggctctcccg gatgcaaggg gctgccacat | 180 |
| agcccagttc aagtccctgt ctccacagga gctgcaggcc tttaagaggg ccaaagatgc | 240 |
| cttagaagag tcgcttctgc tgaaggactg caggtgccac tcccgcctct tcccaggac | 300 |
| ctgggacctg aggcagctgc aggtgaggga gcgccccatg gctttggagg ctgagctggc | 360 |
| cctgacgctg aaggttctgg aggccaccgc tgacactgac ccagccctgg tggacgtctt | 420 |
| ggaccagccc cttcacaccc tgcaccatat cctctcccag ttcgggcct gtatccagcc | 480 |
| tcagcccacg gcagggccca ggacccgggg ccgcctccac cattggctgt accggctcca | 540 |
| ggaggcccca aaaaggagt cccctggctg cctcgaggcc tctgtcacct tcaacctctt | 600 |
| ccgcctcctc acgcgagacc tgaattgtgt tgccagtggg gacctgtgtg tctgacccc | 660 |
| ccaccagtca tgcaacctga gattttattt ataaattagc cacttgtctt aatttattgc | 720 |
| cacccagtcg ctat | 734 |

<210> SEQ ID NO 34
<211> LENGTH: 595
<212> TYPE: DNA
<213> ORGANISM: Homo sapiens

<400> SEQUENCE: 34

| | |
|---|---|
| agacatgacc ggggactgca tgccagtgct ggtgctgatg gccgcagtgc tgaccgtgac | 60 |
| tggagcagtt cctgtcgcca ggctccgcgg ggctctcccg gatgcaaggg gctgccacat | 120 |
| agcccagttc aagtccctgt ctccacagga gctgcaggcc tttaagaggg ccaaagatgc | 180 |
| cttagaagag tcgcttctgc tgaaggactg caagtgccgc tcccgcctct tccccaggac | 240 |
| ctgggacctg aggcagctgc aggtgaggga gcgccccgtg gctttggagg ctgagctggc | 300 |
| cctgacgctg aaggttctgg aggccaccgc tgacactgac ccagccctgg gggatgtctt | 360 |
| ggaccagccc cttcacaccc tgcaccatat cctctcccag ctccgggcct gtatccagcc | 420 |
| tcagcccacg gcagggccca ggacccgggg ccgcctccac cattggctgc accggctcca | 480 |
| ggaggcccca aaaaggagt cccctggctg cctcgaggcc tctgtcacct tcaacctctt | 540 |
| ccgcctcctc acgcgagacc tgaattgtgt tgccagcggg gacctgtgtg tctga | 595 |

<210> SEQ ID NO 35
<211> LENGTH: 856
<212> TYPE: DNA
<213> ORGANISM: Homo sapiens

<400> SEQUENCE: 35

```
aattaccttt tcactttaca cacatcatct tggattgccc attttgcgtg gctaaaaagc      60
agagccatgc cgctggggaa gcagttgcga tttagccatg gctgcagctt ggaccgtggt     120
gctggtgact ttggtgctag gcttggccgt ggcaggccct gtccccactt ccaagcccac     180
cacaactggg aagggctgcc acattggcag gttcaaatct ctgtcaccac aggagctagc     240
gagcttcaag aaggccaggg acgccttgga agagtcactc aagctgaaaa actggagttg     300
cagctctcct gtcttccccg ggaattggga cctgaggctt ctccaggtga gggagcgccc     360
tgtggccttg gaggctgagc tggccctgac gctgaaggtc ctggaggccg ctgctggccc     420
agccctggag gacgtcctag accagcccct cacaccctg caccatcc tctcccagct     480 ccaggcctgt atccagcctc agcccacagc agggcccagg ccccggggcc gcctccacca     540
ctggctgcac cggctccagg aggcccccaa aaaggagtcc gctggctgcc tggaggcatc     600
tgtcaccttc aacctcttcc gcctcctcac gcgagacctc aaatatgtgg ccgatgggaa     660
cctgtgtctg agaacgtcaa cccacccctga gtccacctga caccccacac cttatttatg     720
cgctgagccc tactccttcc ttaatttatt tcctctcacc ctttatttat gaagctgcag     780
ccctgactga gacatagggc tgagtttatt gttttacttt tatacattat gcacaaataa     840
acaacaagga attgga                                                     856

<210> SEQ ID NO 36
<211> LENGTH: 547
<212> TYPE: DNA
<213> ORGANISM: Homo sapiens

<400> SEQUENCE: 36
ctggccttgc tctctctcgc catggcctct cactcaggcc cctcgacgtc tgtgctcttt      60
ctgttctgct gcctgggagg ctggctggcc tcccacacgt tgcccgtccg tttactacga     120
ccaagtgatg atgtacagaa aatagtcgag gaattacagt ccctctcgaa gatgcttttg     180
aaagatgtgg aggaagagaa gggcgtgctc gtgtcccaga attacacgct gccgtgtctc     240
agccctgacg cccagccgcc aaacaacatc cacagcccag ccatccgggc atatctcaag     300
acaatcagac agctagacaa caaatctgtt attgatgaga tcatagagca cctcgacaaa     360
ctcatatttc aagatgcacc agaaacaaac atttctgtgc caacagacac ccatgaatgt     420
aaacgcttca tcctgactat ttctcaacag ttttcagagt gcatggacct cgcactaaaa     480
tcattgacct ctggagcccca acaggccacc acttaaggcc atctcttcct ttcggattgg     540
caggaac                                                               547

<210> SEQ ID NO 37
<211> LENGTH: 1093
<212> TYPE: DNA
<213> ORGANISM: Homo sapiens

<400> SEQUENCE: 37
ccccagccag ctgtcccgag tctggacttt ccctctgccc ctccccactc tcaggctggt      60
ggggtgggga aagcagccca ttcctgggct cagagactcc cacccagct cagagggagc     120 aggggcccag ccagggacgg accctcattc ctcccaggga ccccagacct ctgtctctct     180
cggcaggcct tggctccttg aacttttggc cgccatgtgc ttcccgaagg tcctctctga     240
tgacatgaag aagctgaagg cccgaatgca ccaggccata gaaagatttt atgataaaat     300
gcaaaatgca gaatcaggac gtggacaggt gatgtcgagc ctggcagagc tggaggacga     360
cttcaaagag ggctacctgg agacagtggc ggcttattat gaggagcagc acccagagct     420
```

```
cactcctcta cttgaaaaag aaagagatgg attacggtgc cgaggcaaca gatcccctgt    480
cccggatgtt gaggatcccg caaccgagga gcctggggag agcttttgtg acaaggtcat    540
gagatggttc caggccatgc tgcagcggct gcagacctgg tggcacgggg ttctggcctg    600
ggtgaaggag aaggtggtgg ccctggtcca tgcagtgcag gccctctgga acagttcca    660 gagtttctgc tgctctctgt cagagctctt catgtcctct ttccagtcct acggagcccc    720 acgggggac aaggaggagc tgacaccca gaagtgctct gaaccccaat cctcaaaatg    780
aagatactga caccaccttt gccctccccg tcaccgcgca cccaccctga cccctccctc    840
agctgtcctg tgccccgccc tctcccgcac actcagtccc cctgcctggc gttcctgccg    900
cagctctgac ctggtgctgt cgccctggca tcttaataaa acctgcttat acttccctgg    960
caggggagat accatgatcg cggaggtggg tttcccaggg caaggctgat ctgttgccgt   1020
attagtccgt tttcacacag ctataaagaa tgcctgagac tgggtgatgt ataaagaaaa   1080
gaagtttaac tga                                                      1093

<210> SEQ ID NO 38
<211> LENGTH: 2644
<212> TYPE: DNA
<213> ORGANISM: Homo sapiens

<400> SEQUENCE: 38
caacagaata ctgaaaaatg aagcctaaaa tgaagtattc aaccaacaaa atttccacag     60
caaagtggaa gaacacagca agcaaagcct tgtgtttcaa gctgggaaaa tcccaacaga    120
aggccaaaga agtttgcccc atgtacttta tgaagctccg ctctggcctt atgataaaaa    180
aggaggcctg ttactttagg agagaaacca ccaaaaggcc ttcactgaaa acaggtagaa    240
agcacaaaag acatctggta ctcgctgcct gtcaacagca gtctactgtg gagtgctttg    300
cctttggtat atcaggggtc cagaaatata ctagagcact tcatgattca agtatcacag    360
gaatttcacc tattacagag tatcttgctt ctctaagcac atacaatgat caatccatta    420
cttttgcttt ggaggatgaa agttatgaga tatatgttga agacttgaaa aaagatgaaa    480
agaaagataa ggtgttactg agttactatg agtctcaaca cccctcaaat gaatcaggtg    540
acggtgttga tggtaagatg ttaatggtaa ccctgagtcc tacaaaagac ttctggttgc    600
atgccaacaa caaggaacac tctgtggagc tccataagtg tgaaaaacca ctgccagacc    660
aggccttctt tgtccttcat aatatgcact ccaactgtgt ttcatttgaa tgcaagactg    720
atcctggagt gtttataggt gtaaaggata tcatcttgc tctgattaaa gtagactctt    780
ctgagaattt gtgtactgaa aatatcttgt ttaagctctc tgaaacttag ttgatggaaa    840
cctgtgagtc ttgggttgag tacccaaatg ctaccactgg agaaggaatg agagataaag    900
aaagagacag gtgacatcta agggaaatga agagtgctta gcatgtgtgg aatgttttcc    960
atattatgta taaaaatatt ttttctaatc ctccagttat tctttatttt ccctctgtat   1020
aactgcatct tcaatacaag tatcagtata ttaaataggg tattggtaaa gaacggtca    1080 acattctaaa gagatacagt ctgaccttta cttttctcta gtttcagtcc agaaagaact   1140
tcatatttag agctaaggcc actgaggaaa gagccatagc ttaagtctct atgtagacag   1200
ggatccattt taaagagcta cttagagaaa taatttttcca cagttccaaa cgataggctc   1260
aaacactaga gctgctagta aaaagaagac cagatgcttc acagaattat cattttttca   1320
actggaataa aacaccaggt tgtttgtag atgtcttagg caacactcag agcagatctc   1380
```

```
ccttactgtc aggggatatg gaacttcaaa ggcccacatg gcaagccagg taacataaat    1440
gtgtgaaaaa gtaaagataa ctaaaaaatt tagaaaaata aatccagtat ttgtaaagtg    1500
aataacttca tttctaattg tttaattttt aaaattctga ttttatatata ttgagtttaa   1560 gcaaggcatt cttacacgag gaagtgaagt aaatttagt tcagacataa aatttcactt     1620
attaggaata tgtaacatgc taaaactttt ttttttttaa agagtactga gtcacaacat    1680
gttttagagc atccaagtac catataatcc aactatcatg gtaaggccag aaatcttcta    1740
acctaccaga gcctagatga gacaccgaat taacattaaa atttcagtaa ctgactgtcc    1800
ctcatgtcca tggcctacca tcccttctga ccctggcttc cagggaccta tgtcttttaa    1860
tactcactgt cacattgggc aaagttgctt ctaatcctta tttcccatgt gcacaagtct    1920
ttttgtattc cagcttcctg ataacactgc ttactgtgga atattcattt gacatctgtc    1980
tcttttcatt tcttttaact accatgccct tgatatatct tttgcacctg ctgaacttca    2040
tttctgtatc acctgacctc tggatgccaa aacgtttatt ctgctttgtc tgttgtagaa    2100
ttttagataa agctattaat ggcaatattt ttttgctaaa cgttttttgtt ttttactgtc   2160 actagggcaa taaaatttat actcaaccat ataataacat ttttaacta ctaaaggagt     2220 agttttatt ttaaagtctt agcaatttct attacaactt ttcttagact taacacttat     2280
gataaatgac taacatagta acagaatctt tatgaaatat gaccttttct gaaaatacat    2340 actttacat ttctactta ttgagaccta ttagatgtaa gtgctagtag aatataagat      2400
aaaagaggct gagaattacc atacaagggt attacaactg taaaacaatt tatctttgtt    2460
tcattgttct gtcaataatt gttaccaaag agataaaaat aaaagcagaa tgtatatcat    2520
cccatctgaa aaacactaat tattgacatg tgcatctgta caataaactt aaaatgatta    2580
ttaaataatc aaatatatct actacattgt ttatattatt gaataaagta tattttccaa    2640
atgt                                                                2644

<210> SEQ ID NO 39
<211> LENGTH: 21
<212> TYPE: RNA
<213> ORGANISM: Artificial
<220> FEATURE:
<223> OTHER INFORMATION: Synthetic primer

<400> SEQUENCE: 39
gccaaggagu gcuaaagaau u                                              21

<210> SEQ ID NO 40
<211> LENGTH: 21
<212> TYPE: RNA
<213> ORGANISM: Artificial
<220> FEATURE:
<223> OTHER INFORMATION: Synthetic primer

<400> SEQUENCE: 40
uucuuuagca cuccuuggcu u                                              21

<210> SEQ ID NO 41
<211> LENGTH: 21
<212> TYPE: RNA
<213> ORGANISM: Artificial
<220> FEATURE:
<223> OTHER INFORMATION: Synthetic primer

<400> SEQUENCE: 41
gaagagggcu gagaauucau u                                              21
```

```
<210> SEQ ID NO 42
<211> LENGTH: 21
<212> TYPE: RNA
<213> ORGANISM: Artificial
<220> FEATURE:
<223> OTHER INFORMATION: Synthetic primer

<400> SEQUENCE: 42
ugaauucuca gcccucuucu u                                              21

<210> SEQ ID NO 43
<211> LENGTH: 21
<212> TYPE: RNA
<213> ORGANISM: Artificial
<220> FEATURE:
<223> OTHER INFORMATION: Synthetic primer

<400> SEQUENCE: 43
gaacugagag ugauugagau u                                              21

<210> SEQ ID NO 44
<211> LENGTH: 21
<212> TYPE: RNA
<213> ORGANISM: Artificial
<220> FEATURE:
<223> OTHER INFORMATION: Synthetic primer

<400> SEQUENCE: 44
ucucaaucac ucucaguucu u                                              21

<210> SEQ ID NO 45
<211> LENGTH: 21
<212> TYPE: RNA
<213> ORGANISM: Artificial
<220> FEATURE:
<223> OTHER INFORMATION: Synthetic primer

<400> SEQUENCE: 45
ggaccacacu gcgccaacau u                                              21

<210> SEQ ID NO 46
<211> LENGTH: 20
<212> TYPE: RNA
<213> ORGANISM: Artificial
<220> FEATURE:
<223> OTHER INFORMATION: Synthetic primer

<400> SEQUENCE: 46
uguuggcgca gugugguccu                                                20
```